US012799165B2

(12) United States Patent
Pei

(10) Patent No.: US 12,799,165 B2
(45) Date of Patent: *Nov. 17, 2026

(54) CYCLIC CELL-PENETRATING PEPTIDE COMPOUNDS

(71) Applicant: Ohio State Innovation Foundation, Columbus, OH (US)

(72) Inventor: Dehua Pei, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/329,427

(22) Filed: Sep. 15, 2025

(65) Prior Publication Data

US 2026/0001916 A1 Jan. 1, 2026

Related U.S. Application Data

(63) Continuation of application No. 18/644,750, filed on Apr. 24, 2024, which is a continuation of application No. 17/053,684, filed as application No. PCT/US2019/031522 on May 9, 2019, now Pat. No. 11,987,647.

(60) Provisional application No. 62/669,146, filed on May 9, 2018.

(51) Int. Cl.
*C07K 7/64* (2006.01)

(52) U.S. Cl.
CPC .................................... *C07K 7/64* (2013.01)

(58) Field of Classification Search
None
See application file for complete search history.

(56) References Cited

U.S. PATENT DOCUMENTS 5,523,308 A 6/1996 Costanzo et al.
5,670,483 A 9/1997 Zhang et al.
5,804,558 A 9/1998 Lehrer et al.
5,965,536 A 10/1999 Cohen et al.
6,110,889 A 8/2000 Miller et al.
6,251,854 B1 6/2001 Montal et al.
6,355,619 B1 3/2002 Miller et al.
6,593,292 B1 7/2003 Rothbard et al.
6,605,115 B1 8/2003 Cooke et al.
6,649,587 B1 11/2003 Frydman et al.
6,669,951 B2 12/2003 Rothbard et al.
6,730,293 B1 5/2004 Rothbard et al.
6,759,387 B2 7/2004 Rothbard et al.
6,864,355 B1 3/2005 May et al.
6,960,648 B2 11/2005 Bonny
7,169,814 B2 1/2007 Rothbard et al.
7,229,961 B2 6/2007 Rothbard et al.
7,468,418 B2 12/2008 Iversen et al.
7,585,834 B2 9/2009 Wender et al.
7,816,490 B2 10/2010 Hogan et al.
7,850,949 B2 12/2010 Fang
8,623,833 B2 1/2014 Rothbard et al.
8,628,750 B2 1/2014 Wester et al.
8,901,071 B2 12/2014 O'Neil et al.
9,303,075 B2 4/2016 Brinkmann et al.
9,868,767 B2 1/2018 Pei et al.
10,501,496 B2 12/2019 Pei et al.
10,626,147 B2 * 4/2020 Pei .................... A61K 49/0041
10,738,093 B2 8/2020 Qian et al.
10,815,276 B2 * 10/2020 Pei .......................... C07K 7/64
10,913,773 B2 2/2021 Pei
11,168,310 B2 * 11/2021 Sethuraman ......... A61K 47/645
11,225,506 B2 1/2022 Pei et al.
11,339,192 B2 5/2022 Pei
11,351,222 B2 6/2022 Pei et al.
11,352,394 B2 6/2022 Pei et al.
11,576,946 B2 2/2023 Pei et al.
11,793,884 B2 10/2023 Pei et al.
11,878,046 B2 1/2024 Pei et al.
11,987,647 B2 5/2024 Pei
11,987,812 B2 5/2024 Yonemitsu et al.
11,987,821 B2 * 5/2024 Sethuraman ............. C07K 7/64
12,171,838 B2 12/2024 Pei et al.
12,454,552 B2 10/2025 Pei et al.
2002/0009491 A1 1/2002 Rothbard et al.
2002/0035243 A1 3/2002 Imfeld et al.
2002/0120100 A1 8/2002 Bonny
2002/0127198 A1 9/2002 Rothbard et al.
2003/0022831 A1 1/2003 Rothbard et al.
2003/0032593 A1 2/2003 Wender et al.
2003/0032594 A1 2/2003 Bonny
2003/0167129 A1 9/2003 Nestor et al.
2004/0014669 A1 1/2004 Selsted et al.
2004/0248783 A1 12/2004 Kawabe et al.

(Continued)

FOREIGN PATENT DOCUMENTS

CA 2417064 A1 2/2002
CA 2455951 A1 2/2003

(Continued)

OTHER PUBLICATIONS

Quian et al. (ACS Chem Biol. Feb. 15, 2013; 8(2): 423-431) (Year: 2013).*
U.S. Appl. No. 19/329,423, Dehua Pei, filed Sep. 15, 2025..
U.S. Appl. No. 19/329,431, Pei et al., filed Sep. 15, 2025.
U.S. Appl. No. 19/329,440, Pei et al., filed Sep. 15, 2025.
Alhakamy N.A., et al., "Noncovalently Associated Cell-penetrating Peptides for Gene Delivery Applications," Therapeutic Delivery, 2013, vol. 4, No. 6, pp. 741-757.
Ali S.A., et al., "A Review of Methods Available to Estimate Solvent-Accessible Surface Areas of Soluble Proteins in the Folded and Unfolded States," Current Protein and Peptide Science, 2014, vol. 15, No. 3, 21 Pages.

(Continued)

*Primary Examiner* — Sergio Coffa
(74) *Attorney, Agent, or Firm* — Knowles Intellectual Property Strategies, LLC

(57) ABSTRACT

Disclosed are cell penetrating peptides and compositions comprising such peptides that can be used to deliver agents to various cell types.

15 Claims, 4 Drawing Sheets

Specification includes a Sequence Listing.

(56) References Cited

U.S. PATENT DOCUMENTS

| | | | |
|---|---|---|---|
| 2005/0107289 | A1 | 5/2005 | Ghadiri et al. |
| 2005/0192210 | A1 | 9/2005 | Rothbard et al. |
| 2006/0128614 | A1 | 6/2006 | Cheng et al. |
| 2007/0041904 | A1 | 2/2007 | Jiang et al. |
| 2008/0234183 | A1 | 9/2008 | Hallbrink et al. |
| 2009/0186802 | A1 | 7/2009 | Alluis et al. |
| 2010/0168034 | A1 | 7/2010 | Lee et al. |
| 2010/0221235 | A1 | 9/2010 | Arranz |
| 2010/0292148 | A1 | 11/2010 | Krippner et al. |
| 2011/0269665 | A1 | 11/2011 | Kole |
| 2012/0016005 | A1 | 1/2012 | Samarsky et al. |
| 2012/0045393 | A1 | 2/2012 | Linder et al. |
| 2014/0235557 | A1 | 8/2014 | De Waard |
| 2014/0294942 | A1 | 10/2014 | French et al. |
| 2014/0303071 | A1 | 10/2014 | O'Neil |
| 2014/0342992 | A1 | 11/2014 | Gait et al. |
| 2015/0038671 | A1 | 2/2015 | Parang et al. |
| 2015/0297742 | A1 | 10/2015 | Strieker et al. |
| 2016/0031941 | A1 | 2/2016 | Eckert et al. |
| 2016/0115202 | A1 | 4/2016 | Pei et al. |
| 2016/0151512 | A1 | 6/2016 | Kim |
| 2016/0235807 | A1 | 8/2016 | Shailubhai |
| 2016/0271216 | A1 | 9/2016 | Kemper et al. |
| 2016/0317679 | A1 | 11/2016 | Baumhof et al. |
| 2017/0112896 | A1 | 4/2017 | Briesewitz |
| 2017/0190743 | A1 | 7/2017 | Pei et al. |
| 2017/0281723 | A1 | 10/2017 | Pei et al. |
| 2017/0304383 | A1 | 10/2017 | Briesewitz et al. |
| 2017/0355730 | A1 | 12/2017 | Pei et al. |
| 2018/0030094 | A1 | 2/2018 | Pei et al. |
| 2018/0030411 | A1 | 2/2018 | Kahvejian et al. |
| 2019/0282654 | A1 | 9/2019 | Pei et al. |
| 2019/0284239 | A1 | 9/2019 | Pei |
| 2019/0284240 | A1 | 9/2019 | Pei et al. |
| 2019/0309020 | A1 | 10/2019 | Pei et al. |
| 2019/0365911 | A1 | 12/2019 | Liu et al. |
| 2020/0291070 | A1 | 9/2020 | Pei |
| 2020/0354697 | A1 | 11/2020 | Sethuraman et al. |
| 2020/0385427 | A1 | 12/2020 | Pei et al. |
| 2022/0177523 | A1 | 6/2022 | Pei et al. |
| 2023/0020092 | A1 | 1/2023 | Qian et al. |
| 2023/0312653 | A1 | 10/2023 | Dougherty et al. |
| 2024/0158445 | A1 | 5/2024 | Pei et al. |
| 2024/0173423 | A1 | 5/2024 | Pei |
| 2024/0360174 | A1 | 10/2024 | Pei et al. |
| 2024/0368227 | A1 | 11/2024 | Pei |
| 2025/0011367 | A1 | 1/2025 | Pei et al. |
| 2025/0090675 | A1 | 3/2025 | Pei et al. |
| 2025/0324980 | A1 | 10/2025 | Wang et al. |
| 2026/0008812 | A1 | 1/2026 | Pei et al. |
| 2026/0008813 | A1 | 1/2026 | Pei et al. |
| 2026/0008816 | A1 | 1/2026 | Pei et al. |
| 2026/0070947 | A1 | 3/2026 | Pei |
| 2026/0070948 | A1 | 3/2026 | Pei et al. |
| 2026/0115301 | A1 | 4/2026 | Pei et al. |
| 2026/0146063 | A1 | 5/2026 | Pei et al. |

FOREIGN PATENT DOCUMENTS

| | | | | |
|---|---|---|---|---|
| CA | 2949705 | A1 | 11/2015 | |
| CA | 3092062 | A1 | 8/2019 | |
| CN | 105440105 | A | 3/2016 | |
| CN | 106852146 | B | 8/2021 | |
| CN | 113861268 | A | 12/2021 | |
| EP | 1185493 | A1 | 3/2002 | |
| EP | 1797901 | A1 | 6/2007 | |
| EP | 2420255 | A2 | 2/2012 | |
| EP | 2426203 | A2 | 3/2012 | |
| EP | 3149025 | B1 | 6/2019 | |
| EP | 3544623 | A1 | 10/2019 | |
| EP | 3613426 | A1 | 2/2020 | |
| HK | 40019383 | | 10/2020 | |
| JP | 3791981 | B2 | 6/2006 | |
| JP | 2009527251 | A | 7/2009 | |
| JP | 2010526091 | A | 7/2010 | |
| JP | 2012131743 | A | 7/2012 | |
| JP | 5909611 | B2 | 4/2016 | |
| JP | 2016065018 | A | 4/2016 | |
| JP | 2017519041 | A | 7/2017 | |
| JP | 2020169170 | A | 10/2020 | |
| JP | 6807831 | B2 | 1/2021 | |
| WO | WO-1999021877 | A1 | 5/1999 | |
| WO | WO-2000011022 | A1 | 3/2000 | |
| WO | WO-2001013957 | A2 | 3/2001 | |
| WO | WO-2001052875 | A1 | 7/2001 | |
| WO | WO-2002031109 | A2 | 4/2002 | |
| WO | WO-2002057313 | A2 | 7/2002 | |
| WO | WO-2002067917 | A1 | 9/2002 | |
| WO | WO-2002090503 | A2 | 11/2002 | |
| WO | WO-2002092617 | A1 | 11/2002 | |
| WO | WO-2003059942 | A2 | 7/2003 | |
| WO | WO-2003070755 | A2 | 8/2003 | |
| WO | WO-2003092631 | A2 | 11/2003 | |
| WO | WO-2003092632 | A2 | 11/2003 | |
| WO | WO-2004050685 | A2 | 6/2004 | |
| WO | WO-2006058436 | A1 | 6/2006 | |
| WO | WO-2007055578 | A1 | 5/2007 | |
| WO | WO-2007072037 | A1 | 6/2007 | |
| WO | WO-2007096662 | A2 | 8/2007 | |
| WO | WO-2007097561 | A1 | 8/2007 | |
| WO | WO-2007108749 | A1 | 9/2007 | |
| WO | WO-2007111993 | A2 | 10/2007 | |
| WO | WO-2008077194 | A1 | 7/2008 | |
| WO | WO-2008134761 | A2 | 11/2008 | |
| WO | WO-2009005793 | A2 | 1/2009 | |
| WO | WO-2009027706 | A2 | 3/2009 | |
| WO | WO-2009092062 | A2 | 7/2009 | |
| WO | WO-2009098450 | A2 | 8/2009 | |
| WO | WO-2010039088 | A1 | 4/2010 | |
| WO | WO-2010072406 | A1 | 7/2010 | |
| WO | WO-2010107832 | A1 | 9/2010 | |
| WO | WO-2011126010 | A1 | 10/2011 | |
| WO | WO-2014052276 | A1 | 4/2014 | |
| WO | WO-2014053629 | A1 | 4/2014 | |
| WO | WO-2014053882 | A1 | 4/2014 | |
| WO | WO-2014086835 | A1 | 6/2014 | |
| WO | WO-2014190257 | A2 | 11/2014 | |
| WO | WO-2014190313 | A2 | 11/2014 | |
| WO | WO-2015051030 | A2 | 4/2015 | |
| WO | WO-2015148620 | A2 | 10/2015 | |
| WO | WO-2015153761 | A2 | 10/2015 | |
| WO | WO-2015179434 | A1 | 11/2015 | |
| WO | WO-2015179691 | A2 * | 11/2015 | ............. A61P 13/00 |
| WO | WO-2015179741 | A1 | 11/2015 | |
| WO | WO-2016033368 | A1 | 3/2016 | |
| WO | WO-2016044683 | A1 | 3/2016 | |
| WO | WO-2016054510 | A1 | 4/2016 | |
| WO | WO-2016173214 | A1 | 11/2016 | |
| WO | WO-2017044855 | A2 | 3/2017 | |
| WO | WO-2017048466 | A1 | 3/2017 | |
| WO | WO-2017050836 | A1 | 3/2017 | |
| WO | WO-2017109076 | A1 | 6/2017 | |
| WO | WO-2018098231 | A1 | 5/2018 | |
| WO | WO-2019165183 | A1 | 8/2019 | |
| WO | WO-2020028254 | A1 | 2/2020 | |
| WO | WO-2020030927 | A1 | 2/2020 | |
| WO | WO-2020102630 | A1 | 5/2020 | |
| WO | WO-2020198151 | A1 | 10/2020 | |
| WO | WO-2020227194 | A1 | 11/2020 | |
| WO | WO-2021041895 | A1 | 3/2021 | |
| WO | WO-2021127650 | A1 | 6/2021 | |
| WO | WO-2022125987 | A1 | 6/2022 | |
| WO | WO-2022178379 | A1 | 8/2022 | |
| WO | WO-2022213118 | A1 | 10/2022 | |
| WO | WO-2022240757 | A1 | 11/2022 | |
| WO | WO-2022251415 | A1 | 12/2022 | |

OTHER PUBLICATIONS

U.S. Appl. No. 19/329,353, Pei et al., filed Sep. 15, 2025.
U.S. Appl. No. 19/329,358, Pei et al., filed Sep. 15, 2025.
U.S. Appl. No. 19/329,410, Pei et al., filed Sep. 15, 2025.
U.S. Appl. No. 19/329,417, Pei et al., filed Sep. 15, 2025.

(56) References Cited

OTHER PUBLICATIONS

Almarsson O., et al., "Crystal Engineering of the Composition of Pharmaceutical Phases. Do Pharmaceutical Co-Crystals Represent a New Path to Improved Medicines," Chemical Communications, 2004, vol. 17, pp. 1889-1896.
Alonso A., et al., "Protein Tyrosine Phosphates in the Human Genome," Cell, Jun. 11, 2004, vol. 117, No. 6, pp. 699-711.
Alzani R., et al., "Suramin Induces Deoligomerization of Human Tumor Necrosis Factor (Alpha)," Journal of Biological Chemistry, Jun. 15, 1993, vol. 268, No. 17, pp. 12526-12529.
Angelini A., et al., "Bicyclic Peptide Inhibitor Reveals Large Contact Interface with a Protease Target," ACS Chemical Biology, 2012, vol. 7, No. 5, pp. 817-821.
Appelbaum J.S., et al., "Arginine Topology Controls Escape of Minimally Cationic Proteins from Early Endosomes to the Cytoplasm," Chemistry and Biology, Jul. 27, 2012, vol. 19, No. 7, pp. 819-830.
Ardi V.C., et al., "Macrocycles that Inhibit the Binding between Heat Shock Protein 90 and TPR-Containing Proteins," ACS Chemical Biology Journal, Dec 16, 2011, vol. 6, No. 12, pp. 1357-1366 (18 Pages).
Baud V., et al., "Is NF-kB a Good Target for Cancer Therapy Hopes and Pitfalls," Nature Reviews Drug Discovery, Jan. 2009, vol. 8, No. 1, pp. 33-40 (18 Pages).
Bedewy W., et al., "Generation of a Cell-Permeable Cycloheptapeptidyl Inhibitor against Peptidyl-Prolyl Isomerase Pin1," Organic & Biomolecular Chemistry, May 31, 2017, vol. 15, No. 21, pp. 4540-4543 (9 Pages).
Beste G., et al., "Small Antibody-like Proteins With Prescribed Ligand Specificities Derived From the Lipocalin Fold," Proceedings of the National Academy of Sciences of the United States of America, Mar. 1999, vol. 96, pp. 1898-1903.
Beutler B., et al., "Purification of Cachectin, a Lipoprotein Lipase-suppressing Hormone Secreted by Endotoxin-Induced Raw 264.7 Cells," The Journal of Experimental Medicine, May 1, 1985, vol. 161, pp. 984-995.
Birts CN., et al., "A Cyclic Peptide Inhibitor of C-Terminal Binding Protein Dimerization Links Metabolism with Mitotic Fidelity in Breast Cancer Cells," Chemical Science, 2013, vol. 4, pp. 3046-3057 (13 Pages).
Borrelli A., et al., "Cell Penetrating Peptides as Molecular Carriers for Anti-Cancer Agents," Molecules, Jan. 31, 2018, vol. 23, No. 2 (295), pp. 1-28.
Buller F., et al., "Discovery of TNF Inhibitors from a DNA-Encoded Chemical Library Based on Diels-Alder Cycloaddition," Chemistry & Biology, Oct. 30, 2009, vol. 16, pp. 1075-1086.
Cascales L., et al., "Identification and Characterization of a New Family of Cell-Penetrating Peptides," Journal of Biological Chemistry, Oct. 21, 2011, vol. 286, No. 42, pp. 36932-36943 (13 Pages).
Cerrato C.P., et al., "Novel Cell-Penetrating Peptide Targeting Mitochondria," The FASEB Journal, Nov. 2015, vol. 29, No. 11, pp. 4589-4599 (11 Pages).
Chan D.S-H., et al., "Structure-Based Discovery of Natural-Product-Like TNF-(Alpha) Inhibitors," Angewandte Chemie International Edition in English, Apr. 6, 2010, vol. 49, No. 16, pp. 2860-2864 (09 Pages).
Chatterjee J., et al., "N-Methylation of Peptides: A New Perspective in Medicinal Chemistry," Accounts of Chemical Research, Oct. 2008, vol. 41, No. 10, pp. 1331-1342.
Chen G., et al., "TNF-R1 Signaling: A Beautiful Pathway," Science, May 31, 2002, vol. 296, pp. 1634-1635.
Chen K., et al., "Engineering Cell-permeable Proteins Through Insertion of Cell- Penetrating Motifs Into Surface Loops," ACS Chemical Biology, Aug. 3, 2020, vol. 15, No. 9, pp. 2568-2576 (10 Pages), DOI: 10.1021/acschembio.0c00593, XP055837925.
Chen S., et al., "Bicyclic Peptide Ligands Pulled out of Cysteine-Rich Peptide Libraries," Journal of the American Chemical Society, Apr. 5, 2013, vol. 135, No. 17, pp. 6562-6569.
Chen S., et al., "Dithiol Amino Acids can Structurally Shape and Enhance the Ligand-Binding Properties of Polypeptides," Nature Chemistry, 2014, vol. 6, No. 11, pp. 1009-1016.
Chen S., et al., "Structurally Diverse Cyclisation Linkers Impose Different Backbone Conformations in Bicyclic Peptides," ChemBioChem, 2012, vol. 13, pp. 1032-1038.
Chen X., et al., "Fusion Protein Linkers: Property, Design and Functionality," Advanced Drug Delivery Reviews, Oct. 15, 2013, vol. 65, No. 10, pp. 1357-1369 (32 Pages).
Chen X., et al., "On-Bead Screening of Combinatorial Libraries: Reduction of Nonspecific Binding by Decreasing Surface Ligand Density," Journal of Combinatorial Chemistry, 2009, vol. 11, No. 4, pp. 604-611, (English).
Cheng S.H., et al., "Defective Intracellular Transport and Processing of CFTR is the Molecular Basis of Most Cystic Fibrosis," Cell, Nov. 16, 1990, vol. 63, No. 4, pp. 827-834.
Choi H., et al., "Discovery of the Inhibitors of Tumor Necrosis Factor Alpha with Structure-Based Virtual Screening," Bioorganic & Medicinal Chemistry Letters, 2010, vol. 20, pp. 6195-6198.
Choi J-M., et al., "Cell Permeable NFAT Inhibitory Peptide Sim-2-VIVIT Inhibits T-Cell Activation and Alleviates Allergic Airway Inflammation and Hyper-Responsiveness," Immunology Letters, 2012, vol. 143, No. 2, pp. 170-176.
Cildir G., et al., "Noncanonical NF-kB Signaling in Health and Disease, " Trends in Molecular Medicine, May 2016, vol. 22, No. 5, pp. 414-429.
Cochran A.G., et al., "Tryptophan Zippers: Stable, Monomeric B-Hairpins," Proceedings of the National Academy of Sciences, May 8, 2001, vol. 98, No. 10, pp. 5578-5583 (8 Pages).
Cooley CB., et al., "Oligocarbonate Molecular Transporters: Oligomerization-Based Syntheses and Cell-Penetrating Studies," Journal of the American Chemical Society, 2009, vol. 131, No. 45, pp. 16401-16403.
Craik D.J., et al., "The Future of Peptide-Based Drugs," Chemical Biology and Drug Design, 2013, vol. 81, No. 1, pp. 136-147.
Cushing P.R., et al., "A Stabilizing Influence: CAL PDZ Inhibition Extends the Half-Life of (Delta)F508-CFTR," Angewandte Chemie International Edition, Dec. 2010, vol. 49, No. 51, pp. 9907-9911.
Dai S., et al., "The IkB Kinase (IKK) Inhibitor, NEMO-Binding Domain Peptide, Blocks Osteoclastogenesis and Bone Erosion in Inflammatory Arthritis," Journal of Biological Chemistry, Sep. 3, 2004, vol. 279, No. 36, pp. 37219-37222 (5 Pages).
Dastpeyman M., et al., "Endosomal Escape Cell-penetrating Peptides Significantly Enhance Pharmacological Effectiveness and CNS Activity of Systemically Administered Antisense Oligonucleotides," International Journal of Pharmaceutics, 2021, vol. 599, No. 120398, pp. 1-10.
Dave S.H., et al., "Amelioration of Chronic Murine Colitis by Peptide-Mediated Transduction of the IkB Kinase Inhibitor NEMO Binding Domain Peptide," The Journal of Immunology, 2007, vol. 179, No. 11, pp. 7852-7859 (9 Pages).
Delfin D.A., et al., "Improvement of Cardiac Contractile Function by Peptide-Based Inhibition of NF-kB in the Utrophin/Dystrophin-Deficient Murine Model of Muscular Dystrophy," Journal of Translational Medicine, May 17, 2011, vol. 9, No. 1, 68, 10 Pages.
Deshayes S., et al., "Cell-Penetrating Peptides: Tools for Intracellular Delivery of Therapeutics," Cellular and Molecular Life Sciences CMLS, 2005, vol. 62, No. 16, pp. 1839-1849.
Desimmie B.A., et al., "Phage Display-Directed Discovery of LEDGF/p75 Binding Cyclic Peptide Inhibitors of HIV Replication," Molecular Therapy, Nov. 2012, vol. 20, No. 11, pp. 2064-2075.
Dewan V., et al., "Cyclic Peptide Inhibitors of HIV-I Capsid-Human Lysyl-tRNA Synthetase Interaction," ACS Chemical Biology, 2012, vol. 7, pp. 761-769.
Do H., et al., "Difatty Acyl-Conjugated Linear and Cyclic Peptides for siRNA Delivery," ACS Omega, 2017, vol. 2, No. 10, pp. 6939-6957.
Dong S-L., et al., "A Photocontrolled (Beta)-Hairpin Peptide," Chemistry—A European Journal, 2006, vol. 12, No. 4, pp. 1114-1120.

(56) References Cited

OTHER PUBLICATIONS

Doran T.M., et al., "Role of Amino Acid Hydrophobicity, Aromaticity, and Molecular Volume on IAPP(20-29) Amyloid Self-assembly," Proteins: Structure, Function, and Bioinformatics, 2012, vol. 80, No. 4, pp. 1053-1065.
Dougherty P.G., et al., "Macrocycles as Protein-Protein Interaction Inhibitors," Biochemical Journal, Mar. 15, 2017, vol. 474, No. 7, pp. 1109-1125.
D'Souza C., et al., "Structural Parameters Modulating the Cellular Uptake of Disulfide-Rich Cyclic Cell-penetrating Peptides: MCoTI-II and SFTI-1," European Journal of Medicinal Chemistry, Elsevier Masson, Amsterdam, NL, Dec 1, 2014, vol. 88, No. 99, pp. 10-18 (9 Pages), ISSN: 0223-5234, XP055725965, Retrieved from URL: http://dx.doi.org/10.1016/j.ejmech.2014.06.047.
Driggers E.M., et al., "The Exploration of Macrocycles for Drug Discovery—an Underexploited Structural Class," Nature Reviews Drug Discovery, Jul. 2008, vol. 7, No. 7, pp. 608-624.
Drumm M.L., et al., "Genetic Variation and Clinical Heterogeneity in Cystic Fibrosis," Annual Review of Pathology, Mechanism Disease, 2012, vol. 7, pp. 267-282.
Duchardt F., et al., "A Cell-Penetrating Peptide Derived from Human Lactoferrin with Conformation-Dependent Uptake Efficiency," Journal of Biological Chemistry, Dec. 25, 2009, vol. 284, No. 52, pp. 36099-36108.
Duchardt F., et al., "A Comprehensive Model for the Cellular Uptake of Cationic Cell-Penetrating Peptides," Traffic, 2007, vol. 8, No. 7, pp. 848-866.
Eguchi A., et al., "Protein Transduction Domain of HIV-1 Tat Protein Promotes Efficient Delivery of DNA into Mammalian Cells," Journal of Biological Chemistry, Jul. 13, 2001, vol. 276, No. 28, pp. 26204-26210 (8 Pages).
Eichler J., et al., "Novel (Alpha)-Glucosidase Inhibitors Identified Using Multiple Cyclic Peptide Combinatorial Libraries," Molecular Diversity, Aug. 1996, vol. 1, No. 4, pp. 233-240, (1995).
Eisenberg D., et al., "The Hydrophobic Moment Detects Periodicity in Protein Hydrophobicity," Proceedings of the National Academy of Sciences, Jan. 1984, vol. 81, No. 1, pp. 140-144.
El Andaloussi S., et al., "Design of a Peptide-Based Vector, PepFect6, for Efficient Delivery of siRNA in Cell Culture and Systemically in Vivo," Nucleic Acids Research, May 2011, vol. 39, No. 9, pp. 3972-3987.
El-Sayed A., et al., "Delivery of Macromolecules using Arginine-Rich Cell-Penetrating Peptides: Ways to Overcome Endosomal Entrapment," The AAPS Journal, Mar. 2009, vol. 11, No. 1, pp. 13-22.
Engleman D.M., et al., "Identifying Nonpolar Transbilayer Helices in Amino Acid Sequences of Membrane Proteins," Annual Review of Biophysics and Biomolecular Structure, 1986, vol. 15, No. 1, pp. 321-353 (35 Pages).
Esposito E., et al., "TNF-Alpha as a Therapeutic Target in Inflammatory Diseases, Ischemia-Reperfusion Injury and Trauma," Current Medicinal Chemistry, 2009, vol. 16, No. 24, pp. 3152-3167.
Fadzen C.M., et al., "Chimeras of Cell-penetrating Peptides Demonstrate Synergistic Improvement in Antisense Efficacy," Biochemistry, Aug. 2019, vol. 58, No. 38, pp. 3980-3989, (30 Pages).
Ferrari A., et al., "Caveolae-Mediated Internalization of Extracellular HIV-1 Tat Fusion Proteins Visualized in Real Time," Molecular Therapy, Aug. 2003, vol. 8, No. 2, pp. 284-294.
Fittipaldi A., et al., "Cell Membrane Lipid Rafts Mediate Caveolar Endocytosis of HIV-1 Tat Fusion Proteins," Journal of Biological Chemistry, Sep. 5, 2003, vol. 278, No. 36, pp. 34141-34149 (10 Pages).
Fosgerau K., et al., "Peptide Therapeutics: Current Status and Future Directions," Drug Discovery Today, Jan. 2015, vol. 20, No. 1, pp. 122-128.
Frackenpohl J., et al., "The Outstanding Biological Stability of (Beta)- and (Gamma)-Peptides Toward Proteolytic Enzymes: An In Vitro Investigation with Fifteen Peptidases," Chembiochem, Jun. 2001, vol. 2, No. 6, pp. 445-455.
Frankel A.D., et al., "Cellular Uptake of the Tat Protein from Human Immunodeficiency Virus," Cell, Dec. 23, 1988, vol. 55, No. 6, pp. 1189-1193.
Furka A., et al., "General Method for Rapid Synthesis of Multicomponent Peptide Mixtures," Internal Journal of Peptide and Protein Research, 1991, vol. 37, pp. 487-493.
Futaki S., et al., "Arginine-Rich Peptides. An Abundant Source of Membrane-Permeable Peptides Having Potential as Carriers for Intracellular Protein Delivery," The Journal of Biological Chemistry, Feb. 23, 2001, vol. 276, No. 8, pp. 5836-5840 (6 Pages).
Futaki S., "Membrane-permeable Arginine-rich Peptides and the Translocation Mechanisms," Advanced Drug Delivery Reviews, 2005, vol. 57, No. 4, pp. 547-558.
Gaurnier-Hausser A., et al., "NEMO-Binding Domain Peptide Inhibits Constitutive NF-(Kappa)B Activity and Reduces Tumor Burden in a Canine Model of Relapsed, Refractory Diffuse Large B-Cell Lymphoma," Clinical Cancer Research, Jul. 15, 2011, vol. 17, No. 14, pp. 4661-4671 (12 Pages).
Giebel L.B., et al., "Screening of Cyclic Peptide Phage Libraries Identifies Ligands That Bind Streptavidin With High Affinities," Biochemistry, 1995, vol. 34, No. 47, pp. 15430-15435.
Gobbo M., et al., "Synthesis and Biological Activity of Some Linear and Cyclic Kinin Analogues," International Journal of Peptide & Protein Research, Jul. 1994, vol. 44, No. 1, pp. 1-9.
Goncalves E., et al., "Binding of Oligoarginine to Membrane Lipids and Heparan Sulfate: Structural and Thermodynamic Characterization of a Cell-Penetrating Peptide," Biochemistry, 2005, vol. 44, No. 7, pp. 2692-2702.
Gotoh Y., et al., "A Homogeneous Time-Resolved Fluorescence-Based High-Throughput Screening System for Discovery of Inhibitors of IKK(Beta)-NEMO Interaction," Analytical Biochemistry, 2010, vol. 405, No. 1, pp. 19-27.
Goun E.A., et al., "Molecular Transporters: Synthesis of Oligoguanidinium Transporters and Their Application to Drug Delivery and Real-time Imaging," ChemBioChem, Oct. 2006, vol. 7, No. 10, pp. 1497-1515.
Green M., et al., "Autonomous Functional Domains of Chemically Synthesized Human Immunodeficiency Virus Tat Trans-Activator Protein," Cell, Dec. 23, 1988, vol. 55, No. 6, pp. 1179-1188.
Gu, Shanshan, et al. "PROTACs: an emerging targeting technique for protein degradation in drug discovery." BioEssays 40.4 (2018): 1700247, 11 pages.
Guo B., et al., "Protein Engineering of the N-Terminus of NEMO: Structure Stabilization and Rescue of IKK(Beta) Binding," Biochemistry, Oct. 6, 2014, vol. 53, No. 43, pp. 6776-6785.
Gupta B., et al., "Intracellular Delivery of Large Molecules and Small Particles by Cell-Penetrating Proteins and Peptides," Advanced Drug Delivery Reviews, 2005, vol. 57, No. 4, pp. 637-651.
Gupta S.C., et al., "Inhibiting NF-(Kappa)B Activation by Small Molecules as a Therapeutic Strategy," Biochimica et Biophysica Acta (BBA)-Gene Regulatory Mechanisms, 2010, vol. 1799, No. 10-12, pp. 775-787 (32 Pages).
Hamill K.M., et al., "Polymyxins Facilitate Entry Into Mammalian Cells," Chemical Science, 2016, vol. 7, No. 8, pp. 5059-5068.
Hancock R., et al., "Peptide Inhibitors of the Keap1-Nrf2 Protein-Protein Interaction," Free Radical Biology and Medicine, 2012, vol. 52, pp. 444-451.
Hariton-Gazal E., et al., "Functional Analysis of Backbone Cyclic Peptides Bearing the Arm Domain of the HIV-1 Rev Protein: Characterization of the Karyophilic Properties and Inhibition of Rev-Induced Gene Expression," Biochemistry, 2005, vol. 44, No. 34, pp. 11555-11566.
He M.M., et al., "Small-molecule Inhibition of TNF-(Alpha)," Science, Nov. 11, 2005, vol. 310, pp. 1022-1025.
He R., et al., "Peptide Conjugates with Small Molecules Designed to Enhance Efficacy and Safety," Molecules, May 14, 2019, vol. 24, No. 10, Article No. 1855, pp. 1-34.
Heinis C, et al., "Phage-Encoded Combinatorial Chemical Libraries Based on Bicyclic Peptides," Nature Chemical Biology, Jul. 2009, vol. 5, No. 7, pp. 502-507.

(56) References Cited

OTHER PUBLICATIONS

Herce H.D., et al., "Arginine-Rich Peptides Destabilize the Plasma Membrane, Consistent with a Pore Formation Translocation Mechanism of Cell-Penetrating Peptides," Biophysical Journal, Oct. 2009, vol. 97, No. 7, pp. 1917-1925.
Herce H.D., et al., "Molecular Dynamics Simulations Suggest a Mechanism for Translocation of the HIV-1 Tat Peptide Across Lipid Membranes," Proceedings of the National Academy of Sciences, Dec 26, 2007, vol. 104, No. 52, pp. 20805-20810.
Herndon T.M., et al., "U.S. Food and Drug Administration Approval: Carfilzomib for the Treatment of Multiple Myeloma," Clinical Cancer Research, Sep. 1, 2013, vol. 19, No. 17, pp. 4559-4563 (6 Pages).
Herrington FD., et al., "Modulation of NF-kB Signaling as a Therapeutic Target in Autoimmunity," Journal of Biomolecular Screening, 2016, vol. 21, No. 3, pp. 223-242.
Hicks A.N., et al., "A Novel EEV-Conjugated PMO, ENTR-701, Reduces Nuclear Foci and Corrects Aberrant Splicing in Myotonic Dystrophy Type 1 Preclinical Models," New Directions in Biology and Disease of Skeletal Muscle Conference, Jun. 20, 2022, 01 Page.
Hili R., et al., "Macrocyclization of Linear Peptides Enabled by Amphoteric Molecules," Journal of the American Chemical Society, 2010, vol. 132, No. 9, pp. 2889-2891.
Hintersteiner M., et al., "Single Bead Labeling Method for Combining Confocal Fluorescence on-bead Screening and Solution Validation of Tagged One-Bead One-Compound Libraries," Chemical Biology, Jul. 31, 2009, vol. 16, pp. 724-735.
Hirose H., et al., "Transient Focal Membrane Deformation Induced by Arginine-rich Peptides Leads to Their Direct Penetration Into Cells," Molecular Therapy, May 2012, vol. 20, No. 5, pp. 984-993.
Holub J.M., et al., "Improved Assays for Determining the Cytosolic Access of Peptides, Proteins, and Their Mimetics, " Biochemistry, Dec 2013, vol. 52, No. 50, pp. 9036-9046.
Hopp T.P., et al., "Prediction of Protein Antigenic Determinants from Amino Acid Sequences," Proceedings of the National Academy of Sciences, Jun. 1981, vol. 78, No. 6, pp. 3824-3828.
Horn M., et al., "Tuning the Properties of a Novel Short Cell-penetrating Peptide by Intramolecular Cyclization With a Triazole Bridge," Chemical Communications, 2016, vol. 52, No. 11, pp. 2261-2264.
Houghten R.A., et al., "Generation and Use of Synthetic Peptide Combinatorial Libraries for Basic Research and Drug Discovery," Nature, Nov. 7, 1991, vol. 354, pp. 84-86.
Hoyer J., et al., "Peptide Vectors for the Nonviral Delivery of Nucleic Acids," Accounts of Chemical Research, 2012, vol. 45, No. 7, pp. 1048-1056.
Hu B-H., et al., "Method for Screening and MALDI-TOF MS Sequencing of Encoded Combinatorial Libraries," Analytical Chemistry, Oct. 1, 2007, vol. 79, No. 19, pp. 7275-7285.
Huang H-C, et al., "Regulation of the Antioxidant Response Element by Protein Kinase C-Mediated Phosphorylation of NF-E2-Related Factor 2," Proceedings of the National Academy of Sciences, Nov. 7, 2000, vol. 97, No. 23, pp. 12475-12480 (7 Pages).
Illsley N.P., et al., "Membrane Chloride Transport Measured Using a Chloride-sensitive Fluorescent Probe," Biochemistry, 1987, vol. 26, No. 5, pp. 1215-1219.
Inoyama D., et al., "Optimization of Fluorescently Labeled Nrf2 Peptide Probes and the Development of a Fluorescence Polarization Assay for the Discovery of Inhibitors of keapl-Nrf2 Interaction," Journal of Biomolecular Screening, 2012, vol. 17, No. 4, pp. 435-447.
International Search Report and Written Opinion for International Application No. PCT/US2019/031522, dated Sep. 27, 2019, 14 Pages.
Ishii T., et al., "Transcription Factor Nrf2 Coordinately Regulates a Group of Oxidative Stress-inducible Genes in Macrophages," Journal of Biological Chemistry, May 26, 2000, vol. 275, No. 21, pp. 16023-16029 (8 Pages).
Jang S., et al., "Cell-Penetrating, Dimeric (Alpha)-Helical Peptides: Nanomolar Inhibitors of HIV-1 Transcription," Angewandte Chemie International Edition, 2014, vol. 53, pp. 10086-10089.
Janin J., "Surface and Inside vols. in Globular Proteins," Nature, Feb. 8, 1979, vol. 277, No. 5696, pp. 491-492 (3 Pages).
Jeong J.H., et al., "siRNA Conjugate Delivery Systems," Bioconjugate Chemistry, 2009, vol. 20, No. 1, pp. 5-14.
Jha D., et al., "CyLoP-1: A Novel Cysteine-Rich Cell-Penetrating Peptide for Cytosolic Delivery of Cargoes," Bioconjugate Chemistry, Feb. 14, 2011, vol. 22, No. 3, pp. 319-328.
Jiang B., et al., "A Selective, Cell-permeable Nonphosphorylated Bicyclic Peptidy1 Inhibitor Against Peptidyl-proly1 Isomerase Pin1," Journal of Medicinal Chemistry, 2015, vol. 58, No. 15, pp. 6306-6312 (8 Pages).
Jimi E., et al., "Selective Inhibition of NF-(Kappa)B Blocks Osteoclastogenesis and Prevents Inflammatory Bone Destruction in Vivo," Nature Medicine, Jun. 2004, vol. 10, No. 6, pp. 617-624.
Jin, Jinmei, et al. "The peptide PROTAC modality: a novel strategy for targeted protein ubiquitination." Theranostics 10.22 (2020): 10141.
Jirka, Silvana MG, et al. "Cyclic peptides to improve delivery and exon skipping of antisense oligonucleotides in a mouse model for duchenne muscular dystrophy." Molecular Therapy 26.1 (2018):132-147.
Joo S.H., "Cyclic Peptides as Therapeutic Agents and Biochemical Tools," Biomolecules & Therapeutics, 2012, vol. 20, No. 1, pp. 19-26.
Joo S.H., et al., "High-Throughput Sequence Determination of Cyclic Peptide Library Members by Partial Edman Degradation/Mass Spectrometry," Journal of the American Chemical Society, 2006, vol. 128, No. 39, pp. 13000-13009.
Josephson L., et al., "High-Efficiency Intracellular Magnetic Labeling with Novel Superparamagnetic-Tat Peptide Conjugates," Bioconjugate Chemistry, 1999, vol. 10, No. 2, pp. 186-191.
Junkes C., et al., "Cyclic Antimicrobial R-, W-rich Peptides: the Role of Peptide Structure and *E. Coli* Outer and Inner Membranes in Activity and the Mode of Action," European Biophysics Journal, 2011, vol. 40, No. 4, pp. 515-528.
Kalafatovic, Daniela, and Ernest Giralt. "Cell-penetrating peptides: Design strategies beyond primary structure and amphipathicity." Molecules 22.11 (2017): 1929.
Kansanen E., et al., "The Keap1-Nrf2 Pathway: Mechanisms of Activation and Dysregulation in Cancer," Redox Biology, 2013, vol. 1, No. 1, pp. 45-49.
Kaplan I.M., et al., "Cationic TAT Peptide Transduction Domain Enters Cells by Macropinocytosis," Journal of Controlled Release, 2005, vol. 102, No. 1, pp. 247-253.
Kawakami M., et al., "Studies of Endotoxin-induced Decrease in Lipoprotein-lipase Activity," The Journal of Experimental Medicine, Sep. 1, 1981, vol. 154, pp. 631-639.
Kawakami T., et al., "In Vitro Selection of Multiple Libraries Created by Genetic Code Reprogramming to Discover Macrocyclic Peptides That Antagonize VEGFR2 Activity in Living Cells," ACS Chemical Biology, Apr. 2013, vol. 8, No. 6, pp. 1205-1214 (46 Pages).
Kerem B-S., et al., "Identification of the Cystic Fibrosis Gene: Genetic Analysis," Science, Sep. 8, 1989, vol. 245, No. 4922, pp. 1073-1080.
Kessler, Horst. "Conformation and biological activity of cyclic peptides." Angewandte Chemie International Edition in English 21.7 (1982): 512-523.
Khabar K.S.A., et al., "WEHI-13VAR: A Stable and Sensitive Variant of WEHI 164 Clone 13 Fibrosarcoma for Tumor Necrosis Factor Bioassay," Immunology Letters, 1995, vol. 46, pp. 107-110.
Khakshoor O., et al., "Artificial P-Sheets: Chemical Models of (Beta)-Sheets," Current Opinion in Chemical Biology, 2008, vol. 12, No. 6, pp. 722-729.
Kimber M.S., et al., "Structural Basis for Specificity Switching of the Src SH2 Domain," Molecular Cell, Jun. 2000, vol. 5, No. 6, pp. 1043-1049.
Kodadek T., et al., "Optimized Protocols for the Isolation of Specific Protein-Binding Peptides or Peptoids from Combinatorial Libraries Displayed on Beads," Molecular Omics, 2006, vol. 2, pp. 25-35.

(56) References Cited

OTHER PUBLICATIONS

Kohli R.M., et al., "Biomimetic Synthesis and Optimization of Cyclic Peptide Antibiotics," Nature, Aug. 8, 2002, vol. 418, No. 6898, pp. 658-661.
Koide A., et al., "The Fibronectin Type III Domain as a Scaffold for Novel Binding Proteins," Journal of Molecular Biology, 1998, vol. 284, pp. 1141-1151.
Kornegay J.N., et al., "NBD Delivery Improves the Disease Phenotype of the Golden Retriever Model of Duchenne Muscular Dystrophy," Skeletal Muscle, 2014, vol. 4, No. 1, 18, 17 Pages.
Kriegler M., et al., "A Novel Form of TNF/Cachectin Is a Cell Surface Cytotoxic Transmembrane Protein: Ramifications for the Complex Physiology of TNF," Cell, Apr. 8, 1988, vol. 53, pp. 45-53.
Kritzer J.A., "Rapid Selection of Cyclic Peptides That Reduce (Alpha)-synuclein Toxicity in Yeast and Animal Models," Nature Chemical Biology, Sep. 2009, vol. 5, No. 9, pp. 655-663.
Kwon Y-U., et al., "Quantitative Comparison of the Relative Cell Permeability of Cyclic and Linear Peptides," Chemistry and Biology, Jun. 2007, vol. 14, No. 6, pp. 671-677.
Kyte J., et al., "A Simple Method for Displaying the Hydropathic Character of a Protein," Journal of Molecular Biology, 1982, vol. 157, No. 1, pp. 105-132.
Lai J.R., et al., "Design of Non-Cysteine-Containing Antimicrobial (Beta)-Hairpins: Structure-Activity Relationship Studies with Linear Protegrin-1 Analogues," Biochemistry, 2002, vol. 41, No. 42, pp. 12835-12842.
Lalonde M.S., et al., "Inhibition of Both HIV-1 Reverse Transcription and Gene Expression by a Cyclic Peptide that Binds the Tat-Transactivating Response Element (TAR) RNA," Plos Pathogenes, May 2011, vol. 7, No. 5, e1002038, pp. 1-17.
Lam K.S., et al., "A New Type of Synthetic Peptide Library for Identifying Ligand-binding Activity," Nature, Nov. 7, 1991, vol. 354, No. 6348, pp. 82-84.
Langham A.A., et al., "Comparison of Interactions Between Beta-Hairpin Decapeptides and SDS/DPC Micelles from Experimental and Simulation Data," BMC Biochemistry, 2007, vol. 8, No. 11, pp. 1-13.
Larochelle J.R., et al., "Fluorescence Correlation Spectroscopy Reveals Highly Efficient Cytosolic Delivery of Certain Penta-Arg Proteins and Stapled Peptides," Journal of the American Chemical Society, 2015, vol. 137, No. 7, pp. 2536-2541.
Lattig-Tunnemann G., et al., "Backbone Rigidity and Static Presentation of Guanidinium Groups Increases Cellular Uptake of Arginine-Rich Cell-Penetrating Peptides," Nature Communications, 2011, vol. 2, No. 453, 6 Pages.
Leduc A-M., et al., "Helix-stabilized Cyclic Peptides as Selective Inhibitors of Steroid Receptor-coactivator Interactions," Proceedings of the National Academy of Sciences of the United States of America, Sep. 30, 2003, vol. 100, No. 20, pp. 11273-11278.
Lee D.L., et al., "Effects of Single d-Amino Acid Substitutions On Disruption of β-sheet Structure And Hydrophobicity in Cyclic 14-Residue Antimicrobial Peptide Analogs Related to Gramicidin S," The Journal of Peptide Research, Feb. 2004, vol. 63, No. 2, pp. 69-84 (27 Pages).
Lee H-J., et al., "PDZ Domains and Their Binding Partners: Structure, Specificity, and Modification," Cell Communication and Signaling, 2010, vol. 8, No. 8, pp. 1-18.
Lee J., et al., "Using Marine Natural Products to Discover a Protease That Catalyzes Peptide Macrocyclization of Diverse Substrates," Journal of the American Chemical Society, Feb. 2009, vol. 131, No. 6, pp. 2122-2124.
Lessard L., et al., "The Two Faces of PTPIB in Cancer," Biochimica et Biophysica Acta, Mar. 2010, vol. 1804, No. 3, pp. 613-619.
Leung C-H., et al., "Structure-based Repurposing of FDA-Approved Drugs as TNF(alpha) Inhibitors," ChemMedChem, 2011, vol. 6, pp. 765-768.
Lewis K.N., et al., "Nrf2, a Guardian of Healthspan and Gatekeeper of Species Longevity," Integrative and Comparative Biology, 2010, vol. 50, No. 5, pp. 829-843.
Li, Qian, et al. "Arginine-rich membrane-permeable peptides are seriously toxic" Pharmacology research & perspectives 5.5 (2017): e00334, 5 pgs.
Li S., et al., "Photolithographic Synthesis of Cyclic Peptide Arrays Using a Differential Deprotection Strategy," Chemical Communications, 2005, vol. 5, pp. 581-583.
Lian W., et al., "Cell-Permeable Bicyclic Peptide Inhibitors Against Intracellular Proteins," Journal of the American Chemical Society, Jun. 27, 2014, vol. 136, No. 28, pp. 9830-9833.
Lian W., et al., "Screening Bicyclic Peptide Libraries for Protein-Protein Interaction Inhibitors: Discovery of a Tumor Necrosis Factor—A Antagonist," Journal of the American Chemical Society, Aug. 14, 2013, vol. 135, No. 32, pp. 11990-11995 (12 Pages).
Liao H., et al., "Cell-permeable Bicyclic Peptidyl Inhibitors Against T-cell Protein Tyrosine Phosphates From a Combinatorial Library," Organic and Biomolecular Chemistry, 2017, vol. 15, No. 45, 9595-9598.
Lightfoot H.L., et al., "Endogenous Polyamine Function the RNA Perspective," Nucleic Acids Research, 2014, vol. 42, No. 18, pp. 11275-11290.
Lin, K-J., Z-H. Liu, and Q-D. You. "QSAR studies of antimicrobial alpha, beta-polypeptides." Pharmaceutical Biotechnology-Beijing-10.5 (2003): 299-303.
Lindgren M., et al., "Classes and Prediction of Cell-Penetrating Peptides," Chapter 1 In: Cell-Penetrating Peptides: Methods and Protocols, Methods in Molecular Biology, Springer Science+ Business Media, LLC, 2011, vol. 683, pp. 3-19.
Liu J., et al., "Nanostructured Materials Designed for Cell Binding and Transduction," Biomacromolecules, 2001, vol. 2, No. 2, pp. 362-368.
Liu R., et al., "A Novel Peptide-Based Encoding System for "One-Bead One-Compound" Peptidomimetic and Small Molecule Combinatorial Libraries," Journal of the American Chemical Society, 2002, vol. 124, No. 26, pp. 7678-7680.
Liu T., et al., "High-Throughput Screening of One-Bead-One Compound Libraries: Identification of Cyclic Peptidyl Inhibitors Against Calcineurin/NFAT Interaction," ACS Combinatorial Science Journal, 2011, vol. 13, pp. 537-546.
Liu T., et al., "Membrane Permeable Cyclic Peptidyl Inhibitors Against Human Peptidylprolyl Isomerase Pin1," Journal of Medicinal Chemistry, 2010, vol. 53, No. 6, pp. 2494-2501.
Liu T., et al., "Synthesis and Screening of a Cyclic Peptide Library: Discovery of Small-Molecule Ligands Against Human Prolactin Receptor," Bioorganic & Medicinal Chemistry, Feb. 1, 2009, vol. 17, No. 3, pp. 1026-1033 (14 Pages).
Liu X., et al., "Do We Need to Optimize Plasma Protein and Tissue Binding in Drug Discovery?," Current Topics in Medicinal Chemistry, 2011, vol. 11, No. 4, pp. 450-466.
Liu Y., et al., "Multifunctional Tandem Peptide Modified Paclitaxel-loaded Liposomes for the Treatment of Vasculogenic Mimicry and Cancer Stem Cells in Malignant Glioma," ACS Applied Materials & Interfaces, 2015, vol. 7, No. 30 pp. 16792-16801 (10 Pages).
Lo S-C., et al., "Structure of the Keap1:Nrf2 Interface Provides Mechanistic Insight Into Nrf2 Signaling," The EMBO Journal, 2006, vol. 25, No. 15, pp. 3605-3617.
Lu J., et al., "Linkers Having a Crucial Role in Antibody-Drug Conjugates," International Journal of Molecular Sciences, 2016, vol. 17, No. 561, pp. 1-22.
Luzi S., et al., "Subunit Disassembly and Inhibition of TNF(Alpha) by a Semi-Synthetic Bicyclic Peptide," Protein Engineering, Design and Selection, 2015, vol. 28, No. 2, pp. 45-52, XP055507589.
Ma B., et al., "Total Synthesis of the Antimitotic Bicyclic Peptide Celogentin C," Journal of the American Chemical Society, Jan. 27, 2010, vol. 132, No. 3, pp. 1159-1171 (37 Pages), XP055300884.
Ma L., et al., "A Novel Small-molecule Tumor Necrosis Factor Alpha Inhibitor Attenuates Inflammation in a Hepatitis Mouse Model," The Journal of Biological Chemistry, May 2, 2014, vol. 289, No. 18, pp. 12457-12466 (11 Pages).
Ma Y., et al., "Direct Cytosolic Delivery of Cargoes in Vivo by a Chimera Consisting of D- and L-Arginine Residues," Journal of Controlled Release, 2012, vol. 162, No. 2, pp. 286-294.
Magzoub M., et al., "Conformational States of the Cell-Penetrating Peptide Penetratin When Interacting With Phospholipid Vesicles:

(56) References Cited

OTHER PUBLICATIONS

Effects of Surface Charge and Peptide Concentration," Biochimica et Biophysica Acta, Jun. 2002, vol. 1563, No. 1-2, pp. 53-63.
Maiolo J.R., et al., "Effects of Cargo Molecules on the Cellular Uptake of Arginine-rich Cell-penetrating Peptides," Biochimica et Biophysica Acta (BBA)—Biomembranes, Jul. 2005, vol. 1712, No. 2, pp. 161-172.
Mancini F., et al., "Inhibition of Tumor Necrosis Factor-(Alpha) (TNF-Alpha)/ TNF-(Alpha) Receptor Binding by Structural Analogues of Suramin," Biochemical Pharmacology, 1999, vol. 58, No. 5, pp. 851-859.
Mandal D., et al., "Cell-Penetrating Homochiral Cyclic Peptides as Nuclear-Targeting Molecular Transporters," Angewandte Chemie International Edition, 2011, vol. 50, No. 41, pp. 9633-9637.
Marsault E., et al., "Macrocycles Are Great Cycles: Applications, Opportunities, and Challenges of Synthetic Macrocycles in Drug Discovery," Journal of Medicinal Chemistry, 2011, vol. 54, No. 7, pp. 1961-2004.
Martin T.L., et al., "The Light Side of Horseradish Peroxidase Histochemistry," Journal of Histochemistry and Cytochemistry, 1984, vol. 32, No. 7, p. 793.
Martinez-Rodriguez S., et al., "Natural Occurrence and Industrial Applications of D-Amino Acids: An Overview," Chemistry & Biodiversity, 2010, vol. 7, No. 6, pp. 1531-1548.
May M.J., et al., Selective Inhibition of NF-(Kappa)B Activation by a Peptide That Blocks the Interaction of NEMO With the I(Kappa)B Kinase Complex, Science, Sep. 1, 2000, vol. 289, No. 5484, pp. 1550-1554.
Meutermans W.D.F., et al., "Synthesis of Difficult Cyclic Peptides by Inclusion of a Novel Photolabile Auxiliary in a Ring Contraction Strategy," Journal of the American Chemical Society, 1999, vol. 121, No. 42, pp. 9790-9796, Published Online: Oct. 8, 1999.
Meyer D., et al., "Aromatic Interactions with Naphthylalanine in a (Beta)-Hairpin Peptide," Journal of Peptide Science, 2013, vol. 19, No. 5, pp. 277-282.
Millward S.W., et al., "A General Route for Post-translational Cyclization of mRNA Display Libraries," Journal of the American Chemical Society, 2005, vol. 127, No. 41, pp. 14142-14143, Published Online: Sep. 27, 2005.
Millward S.W., et al., "Design of Cyclic Peptides That Bind Protein Surfaces with Antibody-Like Affinity," ACS Chemical Biology, 2007, vol. 2, No. 9, pp. 625-634, Published Online on Sep. 21, 2007.
Ming Z., et al., "Synthesis of RGD Containing Peptides and Their Vasodilation Effect," Preparative Biochemistry Biotechnology, 2000, vol. 30, No. 3, pp. 247-256.
Miranda E., et al., "A Cyclic Peptide Inhibitor of HIF-1 Heterodimerization That Inhibits Hypoxia Signaling in Cancer Cells," Journal of the American Chemical Society, 2013, vol. 135, pp. 10418-10425.
Mishra A., et al., "Translocation of Hiv Tat Peptide and Analogues Induces by Multiplexed Membrane and Cytoskeletal Interactions," Proceedings of the National Academy of Sciences of the United States of America, Oct. 11, 2011, vol. 108, No. 41, pp. 16883-16888.
Mitra S., et al., "Highly Sensitive Peptide-Based Probes for Protein Tyrosine Phosphatase Activity Utilizing a Fluorogenic Mimic of Phosphotyrosine," Bioorganic and Medicinal Chemistry Letters, 2005, vol. 15, No. 23, pp. 5142-5145.
Mueller J., et al., "Comparison of Cellular Uptake Using 22 CPPs in 4 Different Cell Lines," Bioconjugate Chemistry, 2008, vol. 19, No. 12, pp. 2363-2374.
Muratovska A., et al., "Conjugate for Efficient Delivery of Short Interfering RNA (siRNA) into Mammalian Cells," FEBS Letters, 2004, vol. 558, No. 1-3, pp. 63-68.
Nakase I., et al., "Efficient Intracellular Delivery of Nucleic Acid Pharmaceuticals Using Cell-Penetrating Peptides," Accounts of Chemical Research, 2012, vol. 45, No. 7, pp. 1132-1139, E-Published Dec 30, 2011.
Nakase I., et al., "Interaction of Arginine-Rich Peptides with Membrane-Associated Proteoglycans is Crucial for Induction of Actin Organization and Macropinocytosis," Biochemistry, 2007, vol. 46, No. 2, pp. 492-501.
Ndikuyeze G.H., et al., "A Phase I Clinical Trial of Systemically Delivered NEMO Binding Domain Peptide in Dogs with Spontaneous Activated B-Cell Like Diffuse Large B-Cell Lymphoma, " PloS one, May 2014, vol. 9, Issue. 5, e95404, 10 Pages.
Nevola L., et al., "Modulating Protein-Protein Interactions: The Potential of Peptides," Chemical Communications, 2015, vol. 51, No. 16, pp. 3302-3315 (15 Pages).
Ngu-Schwemlein M., et al., "In Vitro Synergy Between Some Cationic Amphipathic Cyclooctapeptides and Antibiotics," Australian Journal of Chemistry, AU, 2015, vol. 68, No. 2, pp. 218-223, [X] 1-25 abstract, E.Publish: Oct. 8, 2014, XP093076700, Retrieved from URL: https://www.publish.csiro.au/ch/pdf/CH14427.
Nguyen L.T., et al., "Serum Stabilities of short Tryptophan-and Arginine-rich Antimicrobial Peptide Analogs," Plos One, Sep. 10, 2010, vol. 5, No. 9 (e12684), pp. 1-8.
Nischan N., et al., "Covalent Attachment of Cyclic TAT Peptides to GFP Results in Protein Delivery into Live Cells with Immediate Bioavailability," Angewandte Chemie International Edition in English, 2015, vol. 54, No. 6, pp. 1950-1953 (5 Pages), with Supporting Information pp. S1-S26.
Nori A., et al., "Tat-conjugated Synthetic Macromolecules Facilitate Cytoplasmic Drug Delivery to Human Ovarian Carcinoma Cells," Bioconjugate Chemistry, 2003, vol. 14, No. 1, pp. 44-50.
Ocampo-Garcia B.E., et al., "Design and Biological Evaluation of 99mTc- N2S2-Tat(49-57)-c(RGDyK): A Hybrid Radiopharmaceutical for Tumors Expressing (Alpha) (v) (Beta) (3) Integrins," Nuclear Medicine and Biology, 2013, vol. 40, No. 4, pp. 481-487.
Oeckinghaus A., et al., "The NF-kB Family of Transcription Factors and its Regulation," Cold Spring Harbor Perspectives in Biology, 2009, vol. 1, No. 4, a000034, 15 Pages.
Oh D., et al., "Amphiphilic Bicyclic Peptides as Cellular Delivery Agents," ChemMedChem, 2014, vol. 9, No. 11, pp. 2449-2453 (6 Pages).
Oh D., et al., "Antibacterial Activities of Amphiphilic Cyclic Cell-penetrating Peptides Against Multi Drug-resistant Pathogens," Molecular Pharmaceutics, 2014, vol. 11, No. 10, pp. 3528-3536.
Oh D., et al., "Enhanced Cellular Uptake of Short Polyarginine Peptides through Fatty Acylation and Cyclization," Molecular Pharmaceutics, 2014, vol. 11, No. 8, pp. 2845-2854.
Okamoto H., et al., "Conformational Transitions of Cyclic D,L-Peptides," Journal of Computational Chemistry, 2009, vol. 30, No. 6, pp. 962-973.
Orange J.S., et al., "Cell Penetrating Peptide Inhibitors of Nuclear Factor-kappa B," Cellular and Molecular Life Sciences, 2008, vol. 65, No. 22, pp. 3564-3591.
Palm-Apergi C., et al., "The Membrane Repair Response Masks Membrane Disturbances Caused by Cell-penetrating Peptide Uptake," The FASEB Journal, Jan. 2009, vol. 23, No. 1, pp. 214-223.
Pande S.V., et al., "Synthesis and Antibacterial Evaluation of Carboxamide Derivatives of Amino Acids," Pharmaceutical Chemistry Journal, Apr. 2014, vol. 48, No. 1, 5 Pages.
Pelay-Gimeno M., et al., "Structure-based Design of Inhibitors of Protein-protein Interactions: Mimicking Peptide Binding Epitopes," Angewandte Chemie International Edition, 2015, vol. 54, No. 31, pp. 8896-8927.
Pelay-Gimeno M., et al., "Structure-based Design of Protein-protein Interaction Inhibitors: Stabilization and Mimicking of Peptide Ligands," Angewandte Chemie, 2015, vol. 127, No. 31, pp. 9022-9054.
Pennica D., et al., "Human Tumour Necrosis Factor: Precursor Structure, Expression and Homology to Lymphotoxin," Nature, Dec. 20-27, 1984, vol. 312, pp. 724-729.
Peterson J.M., et al., "Peptide-based Inhibition of NF-(Kappa)B Rescues Diaphragm Muscle Contractile Dysfunction in a Murine Model of Duchenne Muscular Dystrophy," Molecular Medicine, May-Jun. 2011, vol. 17, No. 5-6, pp. 508-515.
Pham W., et al., "Enhancing Membrane Permeability by Fatty Acylation of Oligoarginine Peptides," ChemBioChem, 2004, vol. 5, No. 8, pp. 1148-1151.

(56) References Cited

OTHER PUBLICATIONS

Pomilio A.B., et al., "Naturally-Occurring Cyclopeptides: Structures and Bioactivity," Current Organic Chemistry, Nov. 2006, vol. 10, No. 16, pp. 2075-2121.
Pooga M., et al., "Cellular Translocation of Proteins by Transportan," The FASEB Journal, 2001, vol. 15, No. 8, pp. 1451-1453 (23 Pages).
Pritz S., et al., "Synthesis of Biologically Active Peptide Nucleic Acid-Peptide Conjugates by Sortase-Mediated Ligation," Journal of Organic Chemistry, 2007, vol. 72, No. 10, pp. 3909-3912.
Qian Z., et al., "Early Endosomal Escape of a Cyclic Cell-Penetrating Peptide Allows Effective Cytosolic Cargo Delivery," Biochemistry, 2014, vol. 53, No. 24, pp. 4034-4046, DOI: 10.1021/bi5004102.
Qian Z., et al., "Efficient Delivery of Cyclic Peptides into Mammalian Cells with Short Sequence Motifs," ACS Chemical Biology, 2013, vol. 8, No. 2, pp. 423-431.
Qian Z., et al., "Enhancing the Cell Permeability and Metabolic Stability of Peptidyl Drugs by Reversible Bicyclization," Angewandte Chemie International Edition, Feb. 1, 2017, vol. 56, No. 6, pp. 1525-1529 (11 Pages).
Qian Z., et al., "Intracellular Delivery of Peptidyl Ligands by Reversible Cyclization: Discovery of a PDZ Domain Inhibitor That Rescues CFTR Activity," Angewandte Chemie International Edition, May 11, 2015, vol. 54, No. 20, (127), (5972), pp. 5874-5878 (11 Pages).
Qian, Ziqing, et al. "Monitoring the cytosolic entry of cell-penetrating peptides using a pH-sensitive fluorophore." Chemical Communications 51.11 (2015): 2162-2165.
Qian Ziqing et al, "Discovery and Mechanism of Highly Efficient Cyclic Cell-Penetrating Peptides", BIOCHEMISTRY, vol. 55, No. 18, doi: 10.1021/acs.biochem.6b00226, ISSN 0006-2960, (May 10, 2016), pp. 2601-2612, URL: https://pubs.acs.org/doi/pdf/10.1021/acs.biochem.6b00226, XP055854712.
Qin C., et al., "Optimization of Antibacterial Cyclic Decapeptides," Journal of Combinatorial Chemistry, 2004, vol. 6, No. 3, pp. 398-406.
Rajendran P., et al., "Antioxidants and Human Diseases," Clinica Chimica Acta, 2014, vol. 436, pp. 332-347.
Reay D.P., et al., "Systemic Delivery of NEMO Binding Domain/IKKy Inhibitory Peptide to Young Max Mice Improves Dystrophic Skeletal Muscle Histopathology," Neurobiology of Disease, Sep. 2011, vol. 43, No. 3, pp. 598-608 (21 Pages).
Reissmann, Siegmund. "Cell penetration: scope and limitations by the application of cellpenetrating peptides." Journal of Peptide Science 20.10 (2014): 760-784.
Ren L., et al., "Substrate Specificity of Protein Tyrosine Phosphatases 1B, RPTP(Alpha), SHP-1, and SHP-2," Biochemistry, 2011, vol. 50, No. 12, pp. 2339-2356.
Rezai T., et al., "Conformational Flexibility, Internal Hydrogen Bonding, and Passive Membrane Permeability: Successful in Silico Prediction of the Relative Permeabilities of Cyclic Peptides," Journal of the American Chemical Society, 2006, vol. 128, No. 43, pp. 14073-14080.
Rezai T., et al., "Testing the Conformational Hypothesis of Passive Membrane Permeability Using Synthetic Cyclic Peptide Diastereomers," Journal of the American Chemical Society, 2006, vol. 128, No. 8, pp. 2510-2511.
Rhodes, Curran A., et al. "Cell-permeable bicyclic peptidyl inhibitors against NEMO-IkB kinase interaction directly from a combinatorial library." Journal of the American Chemical Society 140.38 (2018): 12102-12110.
Richard J.P., et al., "Cellular Uptake of Unconjugated TAT Peptide Involves Clathrin-dependent Endocytosis and Heparan Sulfate Receptors," Journal of Biological Chemistry, Apr. 15, 2005, vol. 280, No. 15, pp. 15300-15306.
Rizo J., et al., "Constrained Peptides: Models of Bioactive Peptides and Protein Substructures," Annual Review of Biochemistry, 1992, vol. 61, pp. 387-418.
Roberts K.D., et al., "Efficient Synthesis of Thioether-based Cyclic Peptide Libraries" Tetrahedron Letters, Nov. 1998, vol. 39, No. 45, pp. 8357-8360.
Robinson J.A., "(Beta)-Hairpin Peptidomimetics: Design, Structures and Biological Activities," Accounts of Chemical Research, Oct. 2008, vol. 41, No. 10, pp. 1278-1288.
Rothbard J.B., et al., "Conjugation of Arginine Oligomers to Cyclosporin A Facilitates Topical Delivery and Inhibition of Inflammation," Nature Medicine, Nov. 2000, vol. 6, No. 11, pp. 1253-1257.
Rothwarf D.M., et al., "IKK-(gamma) is an Essential Regulatory Subunit of the IkB Kinase Complex," Nature, Sep. 17, 1998, vol. 395, No. 6699, pp. 297-300.
Rotstein B.H., et al., "Solvatochromic Reagents for Multicomponent Reactions and their Utility in the Development of Cell-Permeable Macrocyclic Peptide Vectors," Chemistry—A European Journal, 2011, vol. 17, No. 44, pp. 12257-12261.
Rueping M., et al., "Cellular Uptake Studies With (Beta)-Peptides," ChemBioChem, Mar. 2002, vol. 3, No. 2-3, pp. 257-259.
Rushe M., et al., "Structure of a NEMO/IKK-Associating Domain Reveals Architecture of the Interaction Site," Structure, May 2008, vol. 16, No. 5, pp. 798-808.
Rutledge S.E., et al., "A. Molecular Recognition of Protein Surfaces: High Affinity Ligands for the Cbp Kix Domain," Journal of the American Chemical Society, 2003, vol. 125, No. 47, pp. 14336-14347.
Saar K., et al., "Cell-penetrating Peptides: A Comparative Membrane Toxicity Study," Analytical Biochemistry, 2005, vol. 345, No. 1, pp. 55-65.
Sahni A., et al., "Cell-Penetrating Peptides Escape the Endosome by Inducing Vesicle budding and Collapse," ACS Chemical Biology, Sep. 18, 2020, vol. 15, No. 9, pp. 2485-2492 (17 Pages).
Saito H., et al., "A Tumor Necrosis Factor Receptor Loop Peptide Mimic Inhibits Bone Destruction to the Same Extent as Anti-tumor Necrosis Factor Monoclonal Antibody in Murine Collagen-induced Arthritis," Arthritis & Rheumatism, Apr. 2007, vol. 56, No. 4, pp. 1164-1174.
Sajid, Muhammad Imran, et al. "Applications of amphipathic and cationic cyclic cell penetrating peptides: Significant therapeutic delivery tool." Peptides 141 (2021): 170542.
Sako Y., et al., "Ribosomal Synthesis of Bicyclic Peptides via Two Orthogonal Inter-Side-Chain Reactions," Journal of the American Chemical Society, 2008, vol. 130, No. 23, pp. 7232-7234.
Sandberg M., et al., "NRF2-regulation in Brain Health and Disease: Implication of Cerebral Inflammation," Neuropharmacology, Apr. 2014, vol. 79, pp. 298-306.
Schmidt N., et al., "Arginine-rich Cell-penetrating Peptides," FEBS Letters, 2010, vol. 584, No. 9, pp. 1806-1813.
Scholl M., et al., "Dendritic and Hyperbranched Polyamides," Progress in Polymer Science, 2009, vol. 34, No. 1, pp. 24-61.
Schwarze S.R., et al., "In Vivo Protein Transduction: Delivery of a Biologically Active Protein into the Mouse," Science, Sep. 3, 1999, vol. 285, No. 5433, pp. 1569-1572(5 Pages).
Scott C.P., et al., "Production of Cyclic Peptides and Proteins in Vivo," Proceedings of the National Academy of Sciences of the United States of America, Nov. 23, 1999, vol. 96, No. 24, pp. 13638-13643.
Seia, Michael, and Einat Zisman. "Different roles of D-amino acids in immune phenomena." The FASEB journal 11.6(1997): 449-456.
Shen Q., et al., "De Novo Design of Helical Peptides to Inhibit Tumor Necrosis Factor-(alpha) by Disrupting Its Trimer Formation," Medicinal Chemistry Communications, 2016, vol. 7, pp. 725-729 (7 Pages).
Shibata W., et al., "Cutting Edge: The IkB kinase (IKK) Inhibitor, NEMO-Binding Domain Peptide, Blocks Inflammatory Injury in Murine Colitis," The Journal of Immunology, 2007, vol. 179, No. 5, pp. 2681-2685 (6 Pages).
Shirazi A.N., et al., "Cyclic Peptide-capped Gold Nanoparticles as Drug Delivery Systems," Molecular Pharmaceutics, 2013, vol. 10, pp. 500-511.
Shirazi A.N., et al., "Cyclic Peptides Containing Tryptophan and Arginine as Src Kinase Inhibitors," Bioorganic and Medicinal Chemistry Letters, 2013, vol. 23, pp. 3230-3234.

(56) References Cited

OTHER PUBLICATIONS

Shirazi A.N., et al., "Cysteine and Arginine-rich Peptides as Molecular Carrier," Bioorganic & Medicinal Chemistry Letters, 2016, vol. 26, pp. 656-661.
Shirazi A.N., et al., "Design and Biological Evaluation of Cell-Penetrating Peptide-Doxorubicin Conjugates as Prodrugs," Molecular Pharmaceutics, 2013, vol. 10, pp. 488-499.
Shrake A., et al., "Environment and Exposure to Solvent of Protein Atoms. Lysozyme and Insulin," Journal of Molecular Biology, 1973, vol. 79, No. 2, pp. 351-371 (22 Pages).
Skelton N.J., et al., "(Beta)-Hairpin Polypeptides by Design and Selection," Journal of Spectroscopy, 2003, vol. 17, No. 2-3, pp. 213-230.
Slee E.A., et al., "Benzyloxycarbonyl-Val-Ala-Asp (OMe) Fluoromethylketone (Z-VAD.FMK) Inhibits Apoptosis by Blocking the Processing of CPP32," Biochemical Journal, Apr. 1996, vol. 315, No. 1, pp. 21-24.
Songyang Z., et al., "Recognition of Unique Carboxyl-terminal Motifs by Distinct PDZ Domains," Science, Jan. 3, 1997, vol. 275, No. 5296, pp. 73-77.
Srinivas N., et al., "Biaryl Amino Acid Templates in Place of D-Pro-L-Pro in Cyclic (Beta)-hairpin Cationic Antimicrobial Peptidemimetics," Organic and Biomolecular Chemistry, 2007, vol. 5, pp. 3100-3105.
Stanford S.M., et al., "High-Throughput Screen using a Single-Cell Tyrosine Phosphatase Assay Reveals Biologically Active Inhibitors of Tyrosine Phosphatase CD45," Proceedings of the National Academy of Sciences, Aug. 28, 2012, vol. 109, No. 35, pp. 13972-13977.
Steiner D., et al., "Efficient Selection of DARPins With Sub-nanomolar Affinities Using SRP Phage Display," Journal of Molecular Biology, 2008, vol. 382, pp. 1211-1227.
Stewart K.M., et al., "Cell-Penetrating Peptides as Delivery Vehicles for Biology and Medicine," Organic and Biomolecular Chemistry, 2008, vol. 6, No. 13, pp. 2242-2255.
Suhorutsenko J., et al., "Cell-penetrating Peptides, PepFects, Show No Evidence of Toxicity and Immunogenicity in Vitro and in Vivo," Bioconjugate Chemistry, Nov. 2011, vol. 22, No. 11, pp. 2255-2262.
Sun S-C., et al., "Regulation of Nuclear Factor-KB in Autoimmunity," Trends in Immunology, Jun. 2013, vol. 34, No. 6, pp. 282-289 (18 Pages).
Sun Y., et al., "A Thioester Ligation Approach to Amphipathic Bicyclic Peptide Library," Organic Letters, 2001, vol. 3, No. 11, pp. 1681-1684.
Sweeney M.C., et al., "Decoding Protein-protein Interactions Through Combinatorial Chemistry: Sequence Specificity of SHP-1, SHP-2, and Ship SH2 Domains," Biochemistry, 2005, vol. 44, No. 45, pp. 14932-14947.
Taguchi K., et al., "Molecular Mechanisms of the Keap1-Nrf2 Pathway in Stress Response and Cancer Evolution," Genes to Cells, 2011, vol. 16, No. 2, pp. 123-140.
Takada Y., et al., "Evodiamine Abolishes Constitutive and Inducible NF-kB Activation by Inhibiting IkBa Kinase Activation, Thereby Suppressing NF-KB- Regulated Antiapoptotic and Metastatic Gene Expression, Up-Regulating Apoptosis, and Inhibiting Invasion," Journal of Biological Chemistry, Apr. 29, 2005, vol. 280, No. 17, pp. 17203-17212.
Takasaki W., et al., "Structure-based Design and Characterization of Exocyclic Peptidomimetics That Inhibit TNF(Alpha) Binding to Its Receptor," Nature Biotechnology, Nov. 1997, vol. 15, pp. 1266-1270.
Tam J.P., et al., "Disulfide Bond Formation in Peptides by Dimethyl Sulfoxide. Scope and Applications," Journal of the American Chemical Society, 1991, vol. 113, No. 17, pp. 6657-6662.
Tang P., et al., "Human pro-Tumor Necrosis Factor Is a Homotrimer," Biochemistry (Mosc), 1996, vol. 35, No. 25, pp. 8216-8225.
Tavassoli A., et al., "Inhibition of HN Budding by a Genetically Selected Cyclic Peptide Targeting the Gag-TSG101 Interaction," ACS Chemical Biology, 2008, vol. 3, No. 12, pp. 757-764.
Thakkar A., et al., "Global Analysis of Peptide Cyclization Efficiency," ACS Combinatorial Science, Feb. 11, 2013, vol. 15, No. 2, pp. 120-129 (21 Pages).
Thakkar A., et al., "Traceless Capping Agent for Peptide Sequencing by Partial Edman Degradation and Mass Spectrometry," Analytical Chemistry, Aug. 15, 2006, vol. 78, No. 16, pp. 5935-5939.
Tian Y., et al., "Achieving Enhanced Cell Penetration of Short Conformationally Constrained Peptides through Amphiphilicity Tuning," Chemical Science, 2017, vol. 8, No. 11, pp. 7576-7581 (6 Pages).
Tien M.Z., et al., "Maximum Allowed Solvent Accessibilites of Residues in Proteins, " Public Library of Science ONE, Nov. 21, 2013, vol. 8, No. 11, e80635, pp. 1-8.
Timmerman P., et al., "A Combinatorial Approach for the Design of Complementarity Determining Region-Derived Peptidomimetics with in Vitro Anti-Tumoral Activity," Journal of Biological Chemistry, Dec. 4, 2009, vol. 284, No. 49, pp. 34126-34134.
Tong K.I., et al., "Different Electrostatic Potentials Define ETGE and DLG Motifs as Hinge and Latch in Oxidative Stress Response," Molecular and Cellular Biology, Nov. 2007, vol. 27, No. 21, pp. 7511-7521.
Tong K.I., et al., "Keapl Recruits Neh2 Through Binding to ETGE and DLG Motifs: Characterization of the Two-site Molecular Recognition Model," Molecular and Cellular Biology, Apr. 2006, vol. 26, No. 8, pp. 2887-2900.
Traboulsi H., et al., "Macrocyclic Cell Penetrating Peptides: A Study of Structure-Penetration Properties," Bioconjugate Chemistry, 2015, vol. 26, pp. 405-411 (10 Pages).
Trinh T.B., et al., "Discovery of a Direct Ras Inhibitor by Screening a Combinatorial Library of Cell-Permeable Bicyclic Peptides," ACS Combinational Science, American Chemical Society, Jan. 11, 2016, vol. 18, No. 1, pp. 75-85, XP055431276.
Tse B.N., et al., "Translation of DNA into a Library of 13 000 Synthetic Small Molecule Macrocycles Suitable for in Vitro Selection," Journal of the American Chemical Society, 2008, vol. 130, No. 46, pp. 15611-15626.
Turner R.A., et al., "Click Chemistry as a Macrocyclization Tool in the Solid-phase Synthesis of Small Cyclic Peptides," Organic Letters, Nov. 2007, vol. 9, No. 24, pp. 5011-5014, E-Published Oct. 23, 2007.
Tyagi M., et al., "Internalization of HIV-1 Tat Requires Cell Surface Heparan Sulfate Proteoglycans," The Journal of Biological Chemistry, Feb. 2, 2001, vol. 276, No. 5, pp. 3254-3261, E-Published Oct. 6, 2000.
Upadhyaya P., et al., "Direct Ras Inhibitors Identified From a Structurally Rigidified Bicyclic Peptide Library," Tetrahedron, Elsevier Sience Publishers, Amsterdam, NL, Oct. 21, 2014, vol. 70, No. 42, pp. 7714-7720 (15 Pages).
Upadhyaya P., et al., "Inhibition of Ras Signaling by Blocking Ras-effector Interactions With Cyclic Peptides," Angewandte Chemie, Int Ed, 2015, vol. 54, No. 26, (127), pp. 7602-7606 (6 Pages). pp. 7712-7716.
Varkouhi A.K., et al., "Endosomal Escape Pathways for Delivery of Biologicals," Journal of Controlled Release, May 2011, vol. 151, No. 3, pp. 220-228, Epublished on Nov. 1, 20103.
Verdurmen et al., "Preferential Uptake of L- versus D-Amino Acid Cell-Penetrating Peptides in a Cell Type-Dependent Manner," Chemistry & Biology, 2011, vol. 18, p. 1000-1010.
Virta P., et al., "Solid-Supported Synthesis of Cryptand-Like Macrobicyclic Peptides," The Journal of Organic Chemistry, 2003, vol. 68, No. 22, pp. 8534-8538.
Vriens K., et al., "Antifungal Plant Defensins: Mechanisms of Action and Production," Molecules, Aug. 14, 2014, vol. 19, No. 8, pp. 12280-12303.
Wadia J.S., et al., "Transmembrane Delivery of Protein and Peptide Drugs by TAT-mediated Transduction in the Treatment of Cancer," Advanced Drug Delivery Reviews, Feb. 2005, vol. 57, No. 4, pp. 579-596, Epublished on Dec 19, 2004.
Wajant H., et al., "Tumor Necrosis Factor Signaling," Cell Death and Differentiation, 2003, vol. 10, pp. 45-65.

(56) References Cited

OTHER PUBLICATIONS

Wallbrecher R., et al., "Exploration of the Design Principles of a Cell-Penetrating Bicyclic Peptide Scaffold," Bioconjugate Chemistry, 2014, vol. 25, No. 5, pp. 955-964, Published Online: Apr. 3, 2014.
Wells J.A., et al., "Reaching for High-hanging Fruit in Drug Discovery at Protein-protein Interfaces," Nature, Dec 13, 2007, vol. 450, No. 7172, pp. 1001-1009.
Wender P.A., et al., "The Design, Synthesis, and Evaluation Of Molecules That Enable or Enhance Cellular Uptake: Peptoid Molecular Transporters," Proceedings of the National Academy of Sciences, Nov. 21, 2000, vol. 97, No. 24, pp. 13003-13008.
White T.R., et al., "On-resin N-methylation of Cyclic Peptides for Discovery of Orally Bioavailable Scaffolds," Nature Chemical Biology, 2011, vol. 7, No. 11, pp. 810-817.
Wolde M., et al., "Targeting CAL as a Negative Regulator of (Delta)F508-CFTR Cell-surface Expression an RNA Interference and Structure-based Mutagenetic Approach," Journal of Biological Chemistry, Mar. 16, 2007, vol. 282, No. 11, pp. 8099-8109, Epublished Dec 11, 2006.
Wolfe, Justin M., et al. "Machine learning to predict cell-penetrating peptides for antisense delivery." ACS central science 4.4 (2018): 512-520.
Wolfe, Justin M., et al. "Perfluoroaryl bicyclic cell-penetrating peptides for delivery of antisense oligonucleotides." Angewandte Chemie 130.17 (2018): 4846-4849.
Wu B., et al., "Octa-Guanidine Morpholino Restores Dystrophin Expression in Cardiac and Skeletal Muscles and Ameliorates Pathology in Dystrophic mdx Mice," Molecular Therapy, May 2009, vol. 17, No. 5, pp. 864-871.
Wu G., et al., "Structural Basis of IAP Recognition by Smac/DIABLO," Nature, Dec. 21-28, 2000, vol. 408, No. 6815, pp. 1008-1012.
Wu X., et al., "Inhibition of Ras-effector Interactions by Cyclic Peptides," Medchemcomm, 2013, vol. 4, pp. 378-382.
Xie, Jing, et al. "Cell-penetrating peptides in diagnosis and treatment of human diseases: from preclinical research to clinical application." Frontiers in pharmacology 11 (2020): 697.
Xie L., et al., "Cellular Effects of Small Molecule PTP1B Inhibitors on Insulin Signaling," Biochemistry, 2003, vol. 42, No. 44, pp. 12792-12804.
Xu L., et al., "Directed Evolution of High-Affinity Antibody Mimics Using mRNA Display," Chemistry & Biology, Aug. 2002, vol. 9, pp. 933-942.
Yamagishi Y., et al., "Natural Product-Like Macrocyclic N-Methyl-Peptide Inhibitors Against a Ubiquitin Ligase Uncovered From a Ribosome-Expressed De Novo Library," Chemistry and Biology, Dec 23, 2011, vol. 18, pp. 1562-1570.
Yamaoka S., et al., "Complementation Cloning of NEMO, a Component of the I(Kappa)B Kinase Complex Essential for NF-(Kappa)B Activation," Cell, Jun. 26, 1998, vol. 93, No. 7, pp. 1231-1240.
Yampolsky L.Y., et al., "The Exchangeability of Amino Acids in Proteins," Genetics, Aug. 2005, vol. 170, pp. 1459-1472.
Yin J., et al., "Genetically Encoded Short Peptide Tag for Versatile Protein Labeling by Sfp Phosphopantetheinyl Transferase," Proceedings of the National Academy of Sciences of the United States of America, Nov. 1, 2005, vol. 102, No. 44, pp. 15815-15820.
Yoo J., et al., "Bioreducible Branched Poly(Modified Nona-arginine) Cell-penetrating Peptide as a Novel Gene Delivery Platform," Journal of Controlled Release, 2017, vol. 246, pp. 142-154.
Zabolotny J.M., et al., "PTP1B Regulates Leptin Signal Transduction in Vivo," Developmental Cell, Apr. 2002, vol. 2, No. 4, pp. 489-495.
Zhang D.D., et al., "Distinct Cysteine Residues in Keapl Are Required for Keap1- Dependent Ubiquitination of Nrf2 and for Stabilization of Nrf2 by Chemopreventive Agents and Oxidative Stress," Molecular and Cellular Biology, Nov. 2003, vol. 23, No. 22, pp. 8137-8151.
Zhang M., et al., "Emerging Roles of Nrf2 and Phase II Antioxidant Enzymes in Neuroprotection," Progress in Neurobiology, 2013, vol. 100, pp. 30-47.
Zhao B., et al., "A Thioether-Stabilized D-Proline-L-Proline Induced [Beta]-Hairpin Peptide of Defensin Segment Increases Its Anti-Candida Albicans Ability", ChemBioChem: A European Journal of Chemical Biology, 2016, vol. 17, No. 15, pp. 1416-1420, Published Online Jun. 20, 2016, XP055510467.
Zhao K., et al., "Enhanced Activity of Cyclic Transporter Sequences Driven by Phase Behavior of Peptide-lipid Complexes," Soft Matter, 2012, vol. 8, No. 24, pp. 6430-6433 (5 Pages).
Zhou H., et al., "Structure-Based Design of High-Affinity Macrocyclic Peptidomimetics to Block the Menin-Mixed Lineage Leukemia 1 (MLL1) Protein-Protein Interaction," Journal of Medicinal Chemistry, 2013, vol. 56, pp. 1113-1123.
Ziegler A., et al., "Interaction of the Protein Transduction Domain of HIV-1 TAT With Heparan Sulfate: Binding Mechanism and Thermodynamic Parameters," Biophysical Journal, Jan. 2004, vol. 86, No. 1, pp. 254-263.
Ziegler A., "Thermodynamic Studies and Binding Mechanisms of Cell-penetrating Peptides With Lipids and Glycosaminoglycans," Advanced Drug Delivery Reviews, Mar. 2008, vol. 60, No. 4-5, pp. 580-597, E-Published Oct. 22, 2007.
Reliance Medical Eye Wash, package insert, 2018.
Salim, Heba et al., "Development of a Cell-Permeable Cyclic Peptidyl Inhibitor against the Keap1-Nrf2 Interaction", Journal of Organic Chemistry, 85 pp. 1416-1424, 2020.
Thermo Fisher web page for amino acid properties, downloaded Mar. 2026.
Qian, Z., "Developments and Applications of Cyclic Cell Penetrating Peptides" Dissertation; Ohio State University Graduate Program in chemistry; Embargoed until Oct. 2016.
Bowie et al., "Deciphering the Message in Protein Sequences: Tolerance to Amino Acid Substitutions" Science, 247: 1306-1310, 1990.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" J. Cell Biol., 111:2129-2138, 1990.
Cardote, T.A.F. et al., "Cyclic and Macrocyclic Peptides as Chemical Tools to Recognize Protein Surfaces and Probe Protein-Protein Interactions," Chem Med Chem, vol. 11, No. 8, pp. 787-794, 2016.
Cascales, L. et al., "Identification and Characterization of a New Family of Cell-Penetrating Peptides," Journal of Biological Chemistry, vol. 286, No. 42, pp. 36932-36943 (13 Pages), Oct. 21, 2011.
Cerrato, C.P. et al., "Novel Cell-Penetrating Peptide Targeting Mitochondria," The FASEB Journal, vol. 29, No. 11, pp. 4589-4599 (11 Pages), Nov. 2015.
Kawczyÿski "Synthesis of conjugates of enzyme inhibitors with amino acid structure and penetrating peptides as potential compounds antifungal" Doctoral dissertation, pp. 1-119, 2016.
Lazar et al., "Transforming Growth Factor: Mutation of Aspartic Acid 47 and Leucine 48 Results in Different Biological Activities" Mol. Cell. Biol., 8: 1247-1252, 1988.
Noguchi, H. et al., "A New Cell-permeable Peptide Allows Successful Allogeneic Islet Transplantation in Mice," Nature Medicine, vol. 10, No. 3, pp. 305-309, Mar. 2004.
Qian, Z. et al., "Structure-based Optimization of a Peptidyl Inhibitor Against Calcineurin-nuclear Factor of Activated T Cell (NFAT) Interaction," Journal of Medicinal Chemistry, vol. 57, No. 18, pp. 7792-7797, 2014.
Rothbard et al., "Arginine-Rich Molecular Transporters for Drug Delivery: Role of Backbone Spacing in Cellular Uptake" J. Med Chem, pp. 3612-3618, 2002.
Verdine et al., "Stapled peptides for intracellular drug targets" Methods in Enzymology, vol. 503, 3-33, 2012.

* cited by examiner

X =

CPP1-1

1-2

1-3

1-4

Y = null 1-5

1-6

1-7

1-8

CYCLIC CELL-PENETRATING PEPTIDE COMPOUNDS

CROSS-REFERENCE TO RELATED APPLICATIONS

This application is a continuation of U.S. application Ser. No. 18/644,750, filed Apr. 24, 2024, which is a continuation of U.S. application Ser. No. 17/053,684, filed Nov. 6, 2020, which is a U.S. national stage application filed under 35 U.S.C. § 371 of International Application No. PCT/US2019/031522, filed May 9, 2019, which claims the benefit of priority to U.S. Provisional Application No. 62/669, 146, filed May 9, 2018. The entirety of each of these applications is hereby incorporated by reference for all purposes.

STATEMENT REGARDING FEDERALLY FUNDED RESEARCH

This invention was made with government support under grant no. GM122459 awarded by the National institutes of Health. The government has certain rights in the invention.

INCORPORATION BY REFERENCE

The Sequence Listing XML file named "25063-206US2_ST26" created on Sep. 15, 2025, and having a size of 143,360 bytes, is hereby incorporated by reference.

BACKGROUND

Traversing the plasma membrane presents a major challenge in drug discovery, especially for biologics such as peptides, proteins and nucleic acids. One potential strategy to subvert the membrane barrier and deliver the biologics into cells is to attach them to "cell-penetrating peptides (CPPs)". Despite three decades of investigation, the fundamental basis for CPP activity remains elusive. CPPs that enter cells via endocytosis must exit from endocytic vesicles in order to reach the cytosol. Unfortunately, the endosomal membrane has proven to be a significant barrier towards cytoplasmic delivery by these CPPs. What are thus needed are new cell penetrating peptides and compositions comprising such peptides that can be used to deliver agents to various cell types.

The compositions and methods disclosed herein address these and other needs.

SUMMARY

In various embodiments, the present disclosure provides a cyclic peptide according to one of Formula I-A to I-F:

I-A

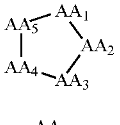

I-B

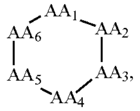

I-C

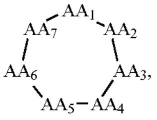

-continued

I-D

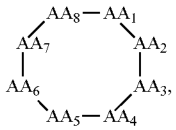

I-E

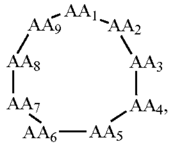

or

I-F

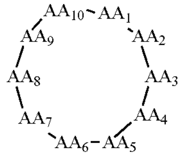

wherein each of $AA_1$, $AA_2$, $AA_3$, $AA_4$, $AA_5$, $AA_6$, $AA_7$, $AA_8$, $AA_9$, and $AA_{10}$, when present, are independently selected from an amino acid; and wherein:

at least two of the amino acids are arginine;

at least one of the amino acids is an amino acid having a non-aromatic hydrophobic side chain.

In various embodiments, the present disclosure provides a cyclic peptide according to one of Formula I-A to I-F:

I-A

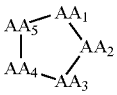

I-B

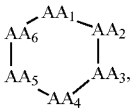

I-C

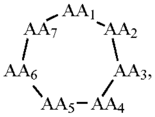

I-D

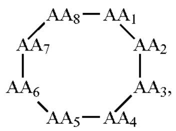

I-E

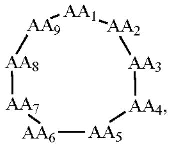

or

I-F

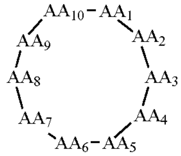

wherein each of $AA_1$, $AA_2$, $AA_3$, $AA_4$, $AA_5$, $AA_6$, $AA_7$, $AA_8$, $AA_9$, and $AA_{10}$, when present, are independently selected from an amino acid; and wherein:

at least two of the amino acids are arginine;

at least one of the amino acids is an amino acid having a non-aromatic hydrophobic side chain, provided that the cyclic peptide is not cyclo(GΦRRRRQ), cyclo(GΦRRR), cyclo(GΦRRRQ), or cyclo (GΦRRRR).

In various embodiments, the present disclosure provides a cyclic peptide according to one of Formula IV-A to IV-F:

IV-A

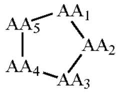

IV-B

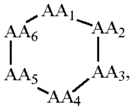

IV-C

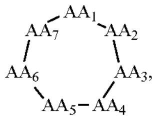

IV-D

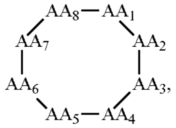

IV-E

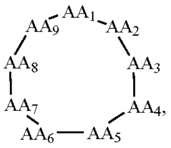

or

IV-F

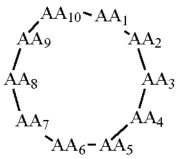

wherein each of $AA_1$, $AA_2$, $AA_3$, $AA_4$, $AA_5$, $AA_6$, $AA_7$, $AA_8$, $AA_9$, and $AA_{10}$, when present, are independently selected from an amino acid; and wherein:

at least two of the amino acids are arginine;

one of the amino acids is an amino acid having a hydrophobic side chain; and the remaining amino acids are amino acids having a non-hydrophobic side chain.

In various embodiments, the present disclosure provides a cyclic peptide according to one of Formula IV-A to IV-F:

IV-A

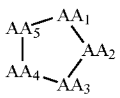

-continued

IV-B

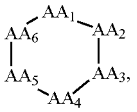

IV-C

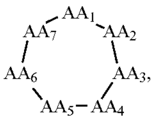

IV-D

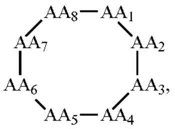

IV-E

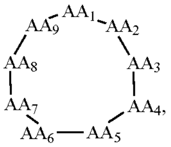

or

IV-F

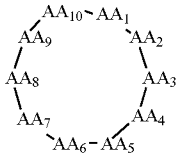

wherein each of $AA_1$, $AA_2$, $AA_3$, $AA_4$, $AA_5$, $AA_6$, $AA_7$, $AA_8$, $AA_9$, and $AA_{10}$, when present, are independently selected from an amino acid; and wherein:

at least two of the amino acids are arginine;

one of the amino acids is an amino acid having a hydrophobic side chain; and the remaining amino acids are amino acids having a non-hydrophobic side chain provided that the cyclic peptide is not cyclo(HΦRRRR), cyclo(YΦRRRR).

In various embodiments, the present disclosure provides a complex comprising a cargo moiety and the cyclic peptide disclosed herein, wherein at least one atom of the cyclic peptide disclosed herein, or at least one lone pair of the cyclic peptide disclosed herein, forms a bond to the cargo moiety.

DETAILED DESCRIPTION

Definitions

Figure 1:
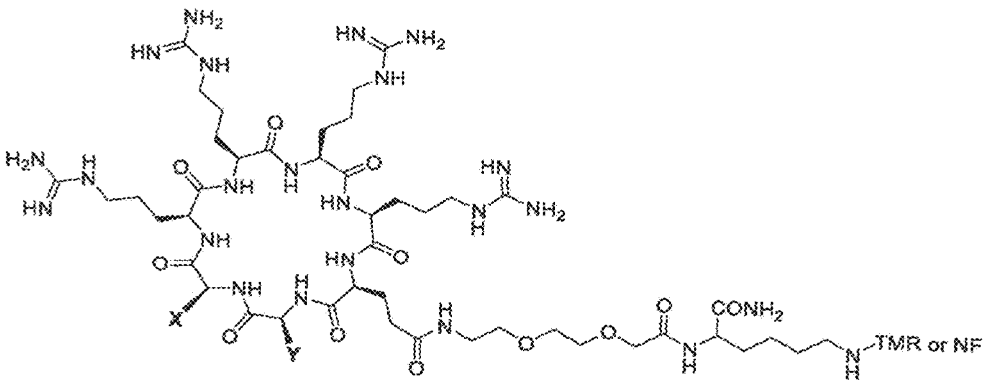
FIG. 1 shows the structures of cyclic CPP1-1 to CPP1-9.
Figure 1:
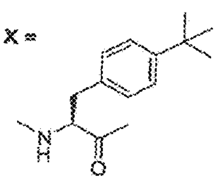
Figure 1:
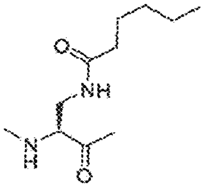
Figure 1:
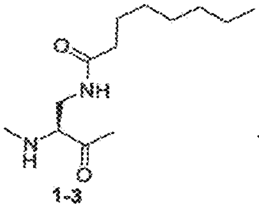
Figure 1:
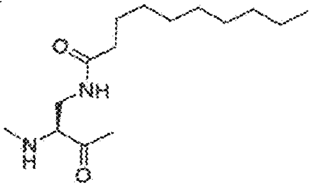
Figure 1:
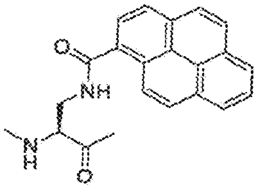
Figure 1:
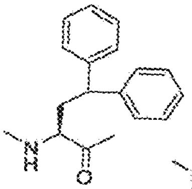
Figure 1:
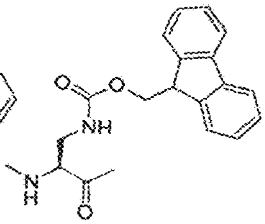
Figure 1:
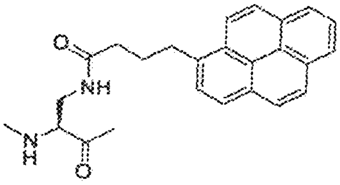

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It will also be understood that when a range is provided, said range encompasses each and every value and subrange within the range.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient" refers to a subject under the treatment of a clinician, e.g., physician.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control (e.g., an untreated tumor).

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly (orthoesters) and poly (anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

The terms "peptide," "protein," and "polypeptide" are used interchangeably to refer to a natural or synthetic molecule comprising two or more amino acids linked by the carboxyl group of one amino acid to the alpha amino group of another.

As used herein, the term "adjacent" refers to two contiguous amino acids, which are connected by a covalent bond. For example, in the context of a representative cyclic peptide such as

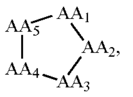

$AA_1/AA_2$, $AA_2/AA_3$, $AA_3/AA_4$, and $AA_5/AA_1$ exemplify pairs of adjacent amino acids. The term "adjacent" can also be applied to amino acids in a linear sequence, i.e, an acyclic peptide.

A residue of a chemical species, as used herein, refers to a derivative of a moiety that is present in a particular product. To form the product, at least one atom of the moiety is replaced by a bond to a second moiety, such that the product contains a derivative of a moiety. For example, in some embodiments, an aromatic residue in a product may refer to one or more $—(C_6H_5)_n$ units present in a cyclic peptide described herein. Similarly, an amino acid residue in a product may refer to cyclic peptide described herein having an amino acid incorporated therein through formation of one or more peptide bonds, and such residues may be referred to interchangeably herein as an amino acid or an amino acid residue.

As used herein, the term "chirality" refers to the "D" and "L" isomers of amino acids or amino acid residues.

As used herein, the term "non-aromatic hydrophobic" refers to a moiety that is not soluble in water and which does not comprise an aromatic ring. Generally, neutral moieties and/or non-polar moieties, or moieties that are predominately neutral and/or non-polar are hydrophobic. Hydrophobic can be measured by one of the methods disclosed herein below. Non-aromatic hydrophobic residues include saturated and unsaturated carbocyclyl and heterocyclyl groups which are not aromatic, as well as alkyl, alkenyl, and alkynyl. In some embodiments, the term "non-aromatic hydrophobic" can include groups in which a hydrophobic residue to attached to rest of the molecule through a bonding group which otherwise could be considered to be polar, such as acyl and alkylcarboxamidyl groups as defined below.

As used herein "aromatic" refers to an unsaturated cyclic molecule having 4n+2π electrons, wherein n is any integer. The term "non-aromatic" refers to any unsaturated cyclic molecule which does not fall within the definition of aromatic.

The term "acyl" refers to groups —C(O)R, where R is hydrogen, alkyl, alkenyl, alkynyl, carbocyclyl, or heterocyclyl, as defined herein. Unless stated otherwise specifically in the specification, acyl can be optionally substituted.

"Alkyl" or "alkyl group" refers to a fully saturated, straight or branched hydrocarbon chain radical having from one to forty carbon atoms, and which is attached to the rest of the molecule by a single bond. Alkyls comprising any number of carbon atoms from 1 to 20 are included. An alkyl comprising up to 40 carbon atoms is a $C_1$-$C_{40}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, 1-butyl, n-pentyl, 1-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. Unless stated otherwise specifically in the specification, an alkylene chain can be optionally substituted.

"Alkenyl" or "alkenyl group" refers to a straight or branched hydrocarbon chain radical having from two to forty carbon atoms, and having one or more carbon-carbon double bonds. Each alkenyl group is attached to the rest of the molecule by a single bond. Alkenyl group comprising any number of carbon atoms from 2 to 40 are included. An alkenyl group comprising up to 40 carbon atoms is a $C_2$-$C_{40}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethene, propene, butene, and the like. Unless stated otherwise specifically in the specification, an alkenylene chain can be optionally.

"Alkoxy" refers to the group —OR, where R is alkyl, alkenyl, alkynyl, cycloalkyl, or heterocyclyl as defined herein. Unless stated otherwise specifically in the specification, alkoxy can be optionally substituted.

"Alkylcarbamoyl" refers to the group —O—C(O)—$NR_aR_b$, where $R_a$ and $R_b$ are the same or different and independently an alkyl, alkenyl, alkynyl, aryl, heteroaryl, cycloalkyl, or heterocyclyl group, as defined herein, or $R_aR_b$ can be taken together to form a heterocyclyl group, as defined herein. Unless stated otherwise specifically in the specification, alkylcarbamoyl can be optionally substituted.

"Alkylcarboxamidyl" refers to the group —C(O)—$NR_aR_b$, where $R_a$ and $R_b$ are the same or different and independently an alkyl, alkenyl, alkynyl, aryl, heteroaryl, cycloalkyl, cycloalkenyl, cycloalkynyl, or heterocyclyl group, as defined herein, or $R_aR_b$ can be taken together to form a cycloalkyl group, as defined herein. Unless stated otherwise specifically in the specification, alkylcarboxamidyl can be optionally substituted.

"Alkoxycarbonyl" refers to the group —C(O)OR, where R is alkyl, alkenyl, alkynyl, aryl, heteroaryl, cycloalkyl, cycloalkenyl, cycloalkynyl, or heterocyclyl group, as defined herein. Unless stated otherwise specifically in the specification, alkoxycarbonyl can be optionally substituted.

"Alkylthio" refers to the —SR or —$S(O)_{n=1-2}$—R, where R is alkyl, alkenyl, alkynyl, cycloalkyl, cycloalkenyl, cycloalkynyl, or hetereocyclyl, as defined herein. Unless stated otherwise specifically in the specification, alkylthio can be optionally substituted.

"Arylthio" refers to the —SR or —$S(O)_{n=1-2}$—R, where R is aryl or hetereoaryl, as defined herein. Unless stated otherwise specifically in the specification, arylthio can be optionally substituted.

"Alkynyl" or "alkynyl group" refers to a straight or branched hydrocarbon chain radical having from two to forty carbon atoms, and having one or more carbon-carbon triple bonds. Each alkynyl group is attached to the rest of the molecule by a single bond. Alkynyl group comprising any number of carbon atoms from 2 to 40 are included. An alkynyl group comprising up to 40 carbon atoms is a $C_2$-$C_{40}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain, having from two to forty carbon atoms, and having one or more carbon-carbon triple bonds. Non-limiting examples of $C_2$-$C_{40}$ alkynylene include ethynylene, propargylene and the like. Unless stated otherwise specifically in the specification, an alkynylene chain can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Unless stated otherwise specifically in the specification, the carbocyclyl can be a monocyclic, bicyclic, tricyclic or tetracyclic ring system, which can include fused or bridged ring systems Carbocyclic rings include cycloalkyl, cycloalkenyl, and cycloalkynyl as defined herein. In some embodiments, the carbocyclyl is monovalent and is attached to the rest of molecule through a single bond. In some embodiments, the carbocyclyl is divalent and is independently attached to two moieties through single bonds. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Heterocyclyl," "heterocyclic ring" or "heterocycle" refers to a stable 3- to 20-membered non-aromatic ring radical, which consists of two to fourteen carbon atoms and from one to eight heteroatoms selected from the group consisting of nitrogen, oxygen and sulfur. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocyclyl is monovalent and is attached to the rest of molecule through a single bond. In some embodiments, the heterocyclyl is divalent and is independently attached to two moieties through single bonds. Unless stated otherwise specifically in the specification, a heterocyclyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aryloxy" refers to groups —OAr, where Ar is an aryl or heteroaryl group as defined herein. Unless otherwise stated specifically in the specification, the aryloxy group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"Aralkyl" refers to a radical of the formula $—R_b—R_c$ where $R_b$ is an alkylene, alkenylene or alkynylene group as defined above and $R_c$ is one or more aryl radicals as defined above, for example, benzyl, diphenylmethyl and the like. Unless stated otherwise specifically in the specification, an aralkyl group can be optionally substituted.

The term "substituted" used herein means any of the above groups (i.e., alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio) wherein at least one atom is replaced by a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more atoms are replaced with $—NR_gR_h$, $—NR_gC(=O)R_h$, $—NR_gC(=O)NR_gR_h$, $—NR_gC(=O)OR_h$, $—NR_gSO_2R_h$, $—OC(=O)NR_gR_h$, $—OR_g$, $—SR_g$, $—SOR_g$, $—SO_2R_g$, $—OSO_2R_g$, $—SO_2OR_g$, $=NSO_2R_g$, and $—SO_2NR_gR_h$. "Substituted also means any of the above groups in which one or more hydrogen atoms are replaced with $—C(=O)R_g$, $—C(=O)OR_g$, $—C(=O)NR_gR_h$, $—CH_2SO_2R_g$, $—CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more atoms are replaced by an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. "Substituted" can also mean an amino acid in which one or more atoms on the side chain are replaced by alkyl, alkenyl, alkynyl, acyl, alkylcarboxamidyl, alkoxycarbonyl, carbocyclyl, heterocyclyl, aryl, or heteroaryl. In addition, each of the foregoing substituents can also be optionally substituted with one or more of the above substituents.

Cell Penetrating Peptides

Disclosed herein are cyclic peptides having activity as cell penetrating peptides (cCPPs). In some embodiments, the cCPPs include any combination of at least two arginines and either at least one amino acid having a non-aromatic hydrophobic side chain or only one amino acid having a hydrophobic side chain, with a total number of amino acids in the cCPP in the range of from 4 to about 20 amino acids. In some embodiments, the cCPPs disclosed herein comprise about 4 to about to about 13 amino acids, e.g., about 5, about 6, about 7, about 8, about 9, about 10, or about 11 amino acids, or about 12 amino acids, inclusive of all ranges and subranges therebetween. In particular embodiments, the cCPPs disclosed herein comprise from about 5 to about 12 amino acids, from about 6 to about 10 amino acids, or from about 6 to about 8 amino acids.

Prior to the present invention, the presence of two hydrophobic aromatic side chains was believed to be critical to efficient cellular uptake. Suprisingly, the inventors discovered that a one of the hydrophobic aromatic side chains can be replaced with a non-aromatic hydrophobic side chain and produce cCPPs with high cytosolic delivery efficiency. In addition, the inventors surprisingly discovered that a cCPP can be synthesized with only one hydrophobic side chain (which may be aromatic or non-aromatic) and still achieve high cytosolic delivery efficency.

Each amino acid can be a natural or non-natural amino acid. The term “non-natural amino acid” refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Thus, as used herein, the term “amino acid” refers to natural and non-natural amino acids, and analogs and derivatives thereof. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, a derivative, or combinations thereof. Analogs of amino acids encompass that have a structural similar but not identical to an amino acid, e.g., due to a modification to the side chain or backbone on said amino acid. Such modifications may increase the hydrophobicity of the side chain, including elongation of the side chain by one or more hydrocarbons, or increasing the the solvent accessible surface area (SASA as described herein) of an amino acid having an aromatic ring on its side chain, e.g., by conjugating a second aromatic ring or increasing the size of the aromatic ring. Derivatives of amino acids encompass natural and non-natural amino acids that have been modified (e.g., by susbstitution) to include a hydrophobic group as described herein. For example, a derivative of lysine includes lysine whose side chain has been substituted with alkylcarboxamidyl. These, and others, are listed in the Table 1 along with their abbreviations used herein.

TABLE 1

Amino Acid Abbreviations

| Amino Acid | Abbreviations* L-amino acid | Abbreviations* D-amino acid |
|---|---|---|
| Alanine | Ala (A) | ala (a) |
| Allosoleucine | AIle | aile |
| Arginine | Arg (R) | arg (r) |
| Asparagine | Asn (N) | asn (n) |
| Aspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa (Σ) | pfa |
| Glutamic acid | Glu (E) | glu (e) |
| Glutamine | Gln (Q) | gln (q) |

TABLE 1-continued

Amino Acid Abbreviations

| Amino Acid | Abbreviations* L-amino acid | Abbreviations* D-amino acid |
|---|---|---|
| Glycine | Gly (G) | gly (g) |
| Gistidine | His (H) | his (h) |
| Homoproline (aka pipecolic acid) | Pip (Θ) | Pip (θ) |
| Isoleucine | Ile (I) | ile (i) |
| Leucine | Leu (L) | leu (l) |
| Lysine | Lys (K) | lys (k) |
| Methionine | Met (M) | met (m) |
| Napthylalanine | Nal (Φ) | nal (φ) |
| Norleucine | Nle (Ω) | nle |
| Phenylalanine | Phe (F) | phe (F) |
| Phenylglycine | Phg (ψ) | phg |
| 4-(phosphonodifluoromethyl) phenylalanine | $F_2$Pmp (Λ) | $f_2$pmp |
| Proline | Pro (P) | pro (p) |
| Sarcosine | Sar (Ξ) | sar |
| Selenocysteine | Sec (U) | sec (u) |
| Serine | Ser (S) | ser (s) |
| Threonine | Thr (T) | thr (y) |
| Tyrosine | Tyr (Y) | tyr (y) |
| Tryptophan | Trp (W) | trp (w) |
| Valine | Val (V) | val (v) |
| 3-(3-benzothienyl)-alanine | Bta | bta |

*single letter abbreviations: when shown in capital letters herein it indicates the L-amino acid form, when shown in lower case herein it indicates the D-amino acid form.

In some embodiments, the present disclosure provides for cyclic peptide having a structure according to Formula I:

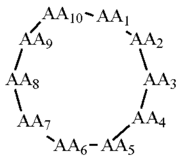

I wherein:

each of $AA_1$, $AA_2$, $AA_3$, $AA_4$, $AA_5$, and $AA_6$ are independently selected from an amino acid; and each of $AA_7$, $AA_8$, $AA_9$, and $AA_{10}$, are independently absent or selected from an amino acid; and wherein:

at least two of $AA_1$, $AA_2$, $AA_3$, $AA_4$, $AA_5$, $AA_6$, $AA_7$, $AA_8$, $AA_9$, or $AA_{10}$ are arginine; and either:

at least one of $AA_1$, $AA_2$, $AA_3$, $AA_4$, $AA_5$, $AA_6$, $AA_7$, $AA_8$ , $AA_9$, or $AA_{10}$ is an amino acid having a non-aromatic hydrophobic side chain, or one of $AA_1$, $AA_2$, $AA_3$, $AA_4$, $AA_5$, $AA_6$, $AA_7$, $AA_8$, $AA_9$, or $AA_{10}$ is an amino acid having a hydrophobic side chain (which may be aromatic or non-aromatic), and the remaining amino acids are amino acids having a non-hydrophobic side chain.

The amino acids, and arrangement thereof, of Formula I are described in detail below in Formulae I-A to I-F and Formulae IV-A to IV-F.

cCPPs With at Least One Amino Acid Having a Hydrophobic Non-Aromatic Side Chain In some embodiments, the cCPPs disclosed herein (i.e., the cyclic peptides of Formula I) have a structure according to any of Formula I-A to I-F:

I-A

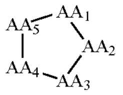

I-B

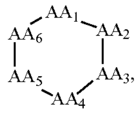

I-C

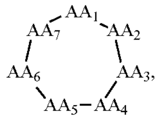

I-D

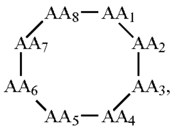

I-E

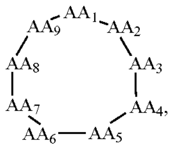

or

I-F

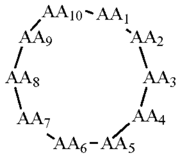

wherein each of $AA_1$, $AA_2$, $AA_3$, $AA_4$, $AA_5$, $AA_6$, $AA_7$, $AA_8$, $AA_9$, and $AA_{10}$, when present, are independently selected from an amino acid; and wherein:

at least two of the amino acids are arginine;

at least one of the amino acids is an amino acid having a non-aromatic hydrophobic side chain.

In some embodiments, the cCPPs disclosed herein (i.e., the cyclic peptides of Formula I) have a structure according to any of Formula I-A to I-F:

I-A

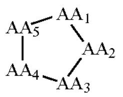

I-B

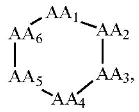

I-C

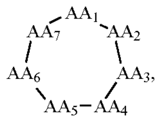

-continued

I-D

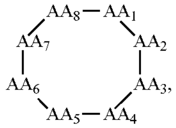

I-E

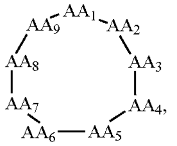

or

I-F

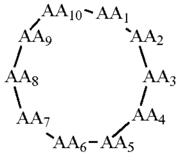

wherein each of $AA_1$, $AA_2$, $AA_3$, $AA_4$, $AA_5$, $AA_6$, $AA_7$, $AA_8$, $AA_9$, and $AA_{10}$, when present, are independently selected from an amino acid; and wherein:

at least two of the amino acids are arginine;

at least one of the amino acids is an amino acid having a non-aromatic hydrophobic side chain, provided that the cyclic peptide is not cyclo(GΦRRRRQ), cyclo (GΦRRR), cyclo(GΦRRRQ), or cyclo(GΦRRRR).

When the cyclic peptide has a structure according to Formula I-A, at least two of $AA_1$, $AA_2$, $AA_3$, $AA_4$, and $AA_5$ are arginine. When the cyclic peptide has a structure according to Formula I-B, at least two of $AA_1$, $AA_2$, $AA_3$, $AA_4$, $AA_5$, and $AA_6$ are arginine. When the cyclic peptide has a structure according to Formula I-C, at least two of $AA_1$, $AA_2$, $AA_3$, $AA_4$, $AA_5$, $AA_6$, and $AA_7$ are arginine. When the cyclic peptide has a structure according to Formula I-D, at least two of $AA_1$, $AA_2$, $AA_3$, $AA_4$, $AA_5$, $AA_6$, $AA_7$, and $AA_8$ are arginine. When the cyclic peptide has a structure according to Formula I-E, at least two of $AA_1$, $AA_2$, $AA_3$, $AA_4$, $AA_5$, $AA_6$, $AA_7$, $AA_8$, and $AA_9$ are arginine. When the cyclic peptide has a structure according to Formula I-F, at least two of $AA_1$, $AA_2$, $AA_3$, $AA_4$, $AA_5$, $AA_6$, $AA_7$, $AA_8$, $AA_9$, and $AA_{10}$ are arginine. Therefore, the cyclic peptide sequences according to Formula I, I-A, I-B, I-C, I-D, I-E, and I-F include at least two arginines.

cCPPs With at Only One Amino Acid Having a Hydrophobic Side Chain

In various embodiments, the cCPPs disclosed herein (i.e. the cyclic peptides of Formula I) have structure according to one of Formula IV-A to IV-F:

IV-A

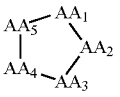

IV-B

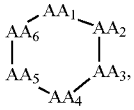

-continued

IV-C

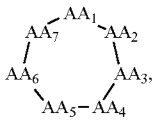

IV-D

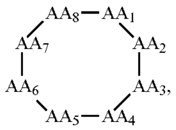

IV-E

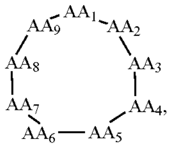 or

IV-F

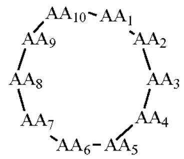

wherein each of $AA_1$, $AA_2$, $AA_3$, $AA_4$, $AA_5$, $AA_6$, $AA_7$, $AA_8$, $AA_9$, and $AA_{10}$, when present, are independently selected from an amino acid; and wherein:

at least two of the amino acids are arginine;

one of the amino acids is an amino acid having a hydrophobic side chain (which may be aromatic or non-aromatic); and the remaining amino acids are amino acids having a non-hydrophobic side chain.

In various embodiments, the present disclosure provides a cyclic peptide according to one of Formula IV-A to IV-F:

IV-A

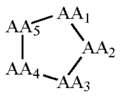

IV-B

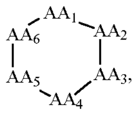

IV-C

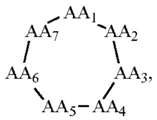

IV-D

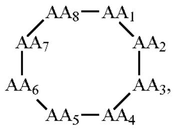

-continued

IV-E

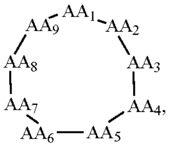 or

IV-F

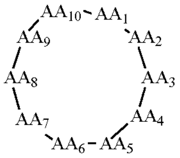

wherein each of $AA_1$, $AA_2$, $AA_3$, $AA_4$, $AA_5$, $AA_6$, $AA_7$, $AA_8$, $AA_9$, and $AA_{10}$, when present, are independently selected from an amino acid; and wherein:

at least two of the amino acids are arginine;

one of the amino acids is an amino acid having a hydrophobic side chain; and the remaining amino acids are amino acids having a non-hydrophobic side chain provided that the cyclic peptide is not cyclo(HΦRRRR) or cyclo(YΦRRRR).

In some embodiments, the cyclic peptide is not cyclo (HΦRRRRQ) or cyclo(YΦRRRRQ).

When the cyclic peptide has a structure according to Formula IV-A, at least two of $AA_1$, $AA_2$, $AA_3$, $AA_4$, and $AA_5$ are arginine. When the cyclic peptide has a structure according to Formula IV-B, at least two of $AA_1$, $AA_2$, $AA_3$, $AA_4$, $AA_5$, and $AA_6$ are arginine. When the cyclic peptide has a structure according to Formula IV-C, at least two of $AA_1$, $AA_2$, $AA_3$, $AA_4$, $AA_5$, $AA_6$, and $AA_7$ are arginine. When the cyclic peptide has a structure according to Formula IV-D, at least two of $AA_1$, $AA_2$, $AA_3$, $AA_4$, $AA_5$, $AA_6$, $AA_7$, and $AA_8$ are arginine. When the cyclic peptide has a structure according to Formula IV-E, at least two of $AA_1$, $AA_2$, $AA_3$, $AA_4$, $AA_5$, $AA_6$, $AA_7$, $AA_8$, and $AA_9$ are arginine. When the cyclic peptide has a structure according to Formula IV-F, at least two of $AA_1$, $AA_2$, $AA_3$, $AA_4$, $AA_5$, $AA_6$, $AA_7$, $AA_8$, $AA_9$, and $AA_{10}$ are arginine. Therefore, the cyclic peptide sequences according to Formula I, IV-A, IV-B, IV-C, IV-D, IV-E, and IV-F include at least two arginines.

Hydrophobic Amino Acids

In some embodiments, each amino acid having a hydrophobic side chain is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylate, 3-(3-benzothienyl)-alanine, or norleucine, each of which is optionally substituted with one or more substituents.

In some embodiments, the amino acid having a hydrophobic side chain is independently an amino acid having a hydrophobic non-aromatic side chain. In some embodiments, an amino acid having a hydrophobic non-aromatic side chain is glycine, alanine, valine, leucine, isoleucine, methionine, or proline. In other embodiments, the amino acid having a hydrophobic non-aromatic side chain has a side chain comprising a C5-C40 alkyl, alkenyl, alkynyl, acyl, alkylcarboxamidyl, alkoxycarbonyl, carbocyclyl, or heterocyclyl.

In some embodiments, the amino acid having a hydrophobic side chain is independently an amino acid having a hydrophobic aromatic side chain. In some embodiments, an amino acid having a hydrophobic aromatic side chain is naphthylalanine, phenylglycine, homophenylalanine, phenylalanine, tryptophan, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1,1'-biphenyl-4-yl)-alanine, 3-(3-benzothienyl)-alanine or tyrosine, each of which is optionally substituted with one or more substituents. The structures of a few of these non-natural aromatic hydrophobic amino acids (prior to incorporation into the peptides disclosed herein) are provided below. In particular embodiments, the hydrophobic amino acid is piperidine-2-carboxylate, naphthylalanine, tryptophan, 3-(3-benzothienyl)-alanine, or phenylalanine, each of which is optionally substituted with one or more substituents.

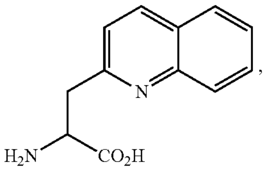

3-(2-quinolyl)-alanine

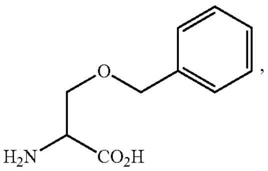

O-benzylserine

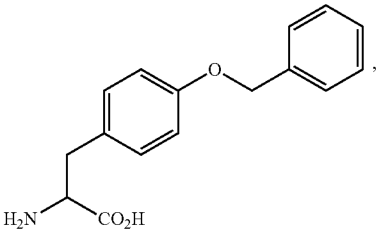

3-(4-(benzyloxy)phenyl)-alanine

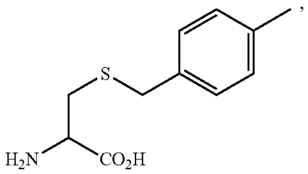

S-(4-methylbenzyl)cysteine

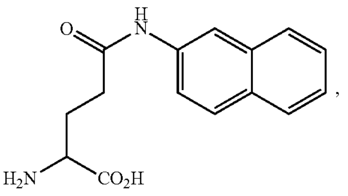

$N^5$-(naphthalen-2-yl)glutamine

-continued

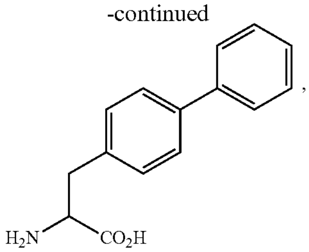

3-(1,1′-biphenyl-4-yl)-alanine

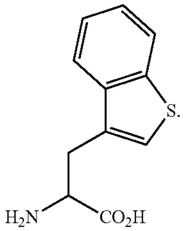

3-(3-benzothienyl)-alanine

Those skilled in the art will appreciate that the N- and/or C-termini of the above non-natural aromatic hydrophobic amino acids, upon incorporation into the peptides disclosed herein, form amide bonds.

The optional substituent can be any atom or group which does not significantly reduce the cytosolic delivery efficiency of the cCPP, e.g., a substituent that does not reduce the relative cytosolic delivery efficiency to less than that of c(FΦRRRRQ). In some embodiments, the optional substituent can be a hydrophobic substituent or a hydrophilic substituent. In certain embodiments, the optional substituent is a hydrophobic substituent. In some embodiments, the substituent increases the solvent-accessible surface area (as defined herein below) of the hydrophobic amino acid. In some embodiments, the substituent can be a halogen, alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio. In some embodiments, the substituent is a halogen.

Amino acids having higher hydrophobicity values can be selected to improve cytosolic delivery efficiency of a cCPP relative to amino acids having a lower hydrophobicity value. In some embodiments, each hydrophobic amino acid independently has a hydrophobicity value which is greater than that of glycine. In other embodiments, each hydrophobic amino acid independently is a hydrophobic amino acid having a hydrophobicity value which is greater than that of alanine. In still other embodiments, each hydrophobic amino acid independently has a hydrophobicity value which is greater or equal to that of phenylalanine. Hydrophobicity may be measured using hydrophobicity scales known in the art. Table 2 below lists hydrophobicity values for various amino acids as reported by Eisenberg and Weiss (Proc. Natl. Acad. Sci. U. S. A. 1984; 81(1):140-144), Engleman, et al. (Ann. Rev. of Biophys. Biophys. Chem. 1986; 1986(15): 321-53), Kyte and Doolittle (J. Mol. Biol. 1982; 157(1): 105-132), Hoop and Woods (Proc. Natl. Acad. Sci. U. S. A. 1981; 78(6):3824-3828), and Janin (Nature. 1979; 277 (5696):491-492), the entirety of each of which is herein incorporated by reference in its entirety. In particular embodiments, hydrophobicity is measured using the hydrophobicity scale reported in Engleman, et al.

TABLE 2

| Amino Acid | Group | Eisenberg and Weiss | Engleman et al. | Kyrie and Doolittle | Hoop and Woods | Janin |
|---|---|---|---|---|---|---|
| Ile | Nonpolar | 0.73 | 3.1 | 4.5 | −1.8 | 0.7 |
| Phe | Nonpolar | 0.61 | 3.7 | 2.8 | −2.5 | 0.5 |
| Val | Nonpolar | 0.54 | 2.6 | 4.2 | −1.5 | 0.6 |
| Leu | Nonpolar | 0.53 | 2.8 | 3.8 | −1.8 | 0.5 |
| Trp | Nonpolar | 0.37 | 1.9 | −0.9 | −3.4 | 0.3 |
| Met | Nonpolar | 0.26 | 3.4 | 1.9 | −1.3 | 0.4 |
| Ala | Nonpolar | 0.25 | 1.6 | 1.8 | −0.5 | 0.3 |
| Gly | Nonpolar | 0.16 | 1.0 | −0.4 | 0.0 | 0.3 |
| Cys | Unch/Polar | 0.04 | 2.0 | 2.5 | −1.0 | 0.9 |
| Tyr | Unch/Polar | 0.02 | −0.7 | −1.3 | −2.3 | −0.4 |
| Pro | Nonpolar | −0.07 | −0.2 | −1.6 | 0.0 | −0.3 |
| Thr | Unch/Polar | −0.18 | 1.2 | −0.7 | −0.4 | −0.2 |
| Ser | Unch/Polar | −0.26 | 0.6 | −0.8 | 0.3 | −0.1 |
| His | Charged | −0.40 | −3.0 | −3.2 | −0.5 | −0.1 |
| Glu | Charged | −0.62 | −8.2 | −3.5 | 3.0 | −0.7 |
| Asn | Unch/Polar | −0.64 | −4.8 | −3.5 | 0.2 | −0.5 |
| Gln | Unch/Polar | −0.69 | −4.1 | −3.5 | 0.2 | −0.7 |
| Asp | Charged | −0.72 | −9.2 | −3.5 | 3.0 | −0.6 |
| Lys | Charged | −1.10 | −8.8 | −3.9 | 3.0 | −1.8 |
| Arg | Charged | −1.80 | −12.3 | −4.5 | 3.0 | −1.4 |

In some embodiments, an arginine is adjacent to a hydrophobic amino acid. In some embodiments, the arginine has the same chirality as the hydrophobic amino acid. In some embodiments, at least two arginines are adjacent to each other. In other embodiments, three arginines are adjacent to each other. In some embodiments, at least two hydrophobic amino acids are adjacent to each other. In other embodiments, at least three hydrophobic amino acids are adjacent to each other. In other embodiments, the CPPs described herein comprise at least two consecutive hydrophobic amino acids and at least two adjacent arginines. In further embodiments, one hydrophobic amino acid is adjacent to one of the arginines. In still other embodiments, the CPPs described herein comprise at least three adjacent hydrophobic amino acids and at least three adjacent arginines. In further embodiments, one hydrophobic amino acid is adjacent to one of the arginines. These various combinations of amino acids can have any arrangement of D and L amino acids, e.g., any of the sequences described in the preceding paragraph.

In some embodiments, any four adjacent amino acids in the cCPPs described herein (e.g., cCPPs of Formulae IA-IF and IVA-IVF) can have one of the following sequences: $AA_{H1}$-R—R—R or R—R—R-$AA_{H1}$, wherein each $AA_{H1}$ is independently an amino acid having a hydrophobic side chain.

Accordingly, in some embodiments, the cCPPs herein (e.g., cCPPs of Formulae IA-IF and IVA-IVF) can have a structure according any of Formula III-A to III-L:

III-A

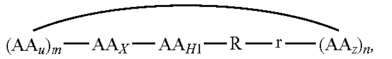

III-B

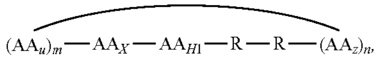

III-C

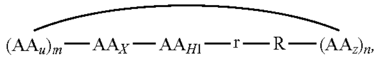

III-D

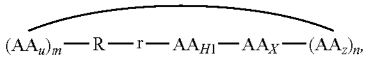

III-E

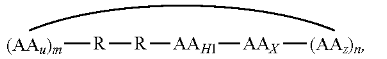

-continued

III-F

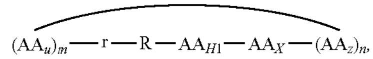

III-G

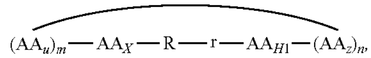

III-H

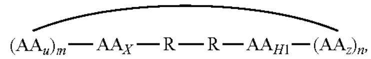

III-I

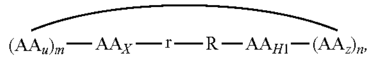

III-J

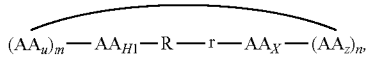

III-K

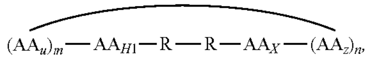

and

III-L

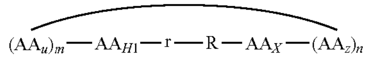

wherein:

AAmi is an amino acid having a non-aromatic hydrophobic side chain;

at each instance $AA_u$, $AA_x$, and AAz are independently any amino acid;

wherein:

each of m and n are independently a number from 0 to 6, provided that at least one of m or n is not 0 and the total number of amino acids is from 5 to 10.

In embodiments in which the cCCP has only one hydrophobic side chain (cCPPs according to Formulae IVA-IVF), none of $AA_u$, $AA_x$, and AAz are amino acids having a hydrophobic side chain.

In certain embodiments, the cCPPs herein (e.g., cCPPs of Formulae IA-IF and IVA-IVF) is:

III-B

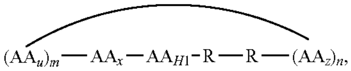

III-E

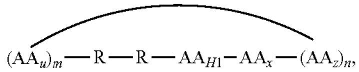

III-H

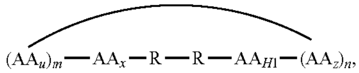

or

III-K

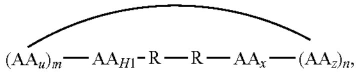

wherein AAH1, AAu, AAx, AAz, m, and n are as defined above.

In some embodiments, the total number of amino acids (including r, R, $AA_{H1}$, $AA_u$, $AA_x$, and $AA_z$), in the cCPPs of Formula III-A to III-L is in the range of 5 to 10. In some embodiments, the total number of amino acids is 5. In some embodiments, the total number of amino acids is 6. In some embodiments, the total number of amino acids is 7. In some embodiments, the total number of amino acids is 8. In some embodiments, the total number of amino acids is 9. In some embodiments, the total number of amino acids is 10.

In some embodiments, the sum of m and n is from 2 to 6. In some embodiments, the sum of m and n is 2. In some embodiments, the sum of m and n is 3. In some embodiments, the sum of m and n is 4. In some embodiments, the sum of m and nis 5. In some embodiments, the sum of m and n is 6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, each hydrophobic amino acid is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylate, or norleucine, each of which is optionally substituted with one or more substituents.

In some embodiments, the amino acid having a hydrophobic side chain is independently an amino acid having a hydrophobic non-aromatic side chain. In some embodiments, an amino acid having a hydrophobic non-aromatic side chain is glycine, alanine, valine, leucine, isoleucine, methionine, or proline. In other embodiments, the amino acid having a hydrophobic non-aromatic side chain is a non-natural amino acid and has a side chain comprising a C5-C40 alkyl, alkenyl, alkynyl, acyl, alkylcarboxamidyl, alkoxycarbonyl, carbocyclyl, or heterocyclyl.

In some embodiments, the amino acid having a hydrophobic side chain is independently an amino acid having a hydrophobic aromatic side chain. In some embodiments, an amino acid having a hydrophobic aromatic side chain is naphthylalanine, phenylglycine, homophenylalanine, phenylalanine, tryptophan, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1,1'-biphenyl-4-yl)-alanine, 3-(3-benzothienyl)-alanine or tyrosine, each of which is optionally substituted with one or more substituents. The structures of a few of these non-natural aromatic hydrophobic amino acids (prior to incorporation into the peptides disclosed herein) are provided below. In particular embodiments, the hydrophobic amino acid is piperidine-2-carboxylate, naphthylalanine, tryptophan, 3-(3-benzothienyl)-alanine, or phenylalanine, each of which is optionally substituted with one or more substituents.

In some embodiments, $AAH_1$ is a hydrophobic amino acid having a hydrophobicity value which is greater than that of glycine. In other embodiments, $AAH_1$ is a hydrophobic amino acid having a hydrophobicity value which is greater than that of alanine. In still other embodiments, each $AAH_1$ is a hydrophobic amino acid having a hydrophobicity value which is greater than that of phenylalanine, e.g., as measured using the hydrophobicity scales described above, including Eisenberg and Weiss (Proc. Natl. Acad. Sci. U. S. A. 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U. S. A. 1981; 78(6):3824-3828), and Janin (Nature. 1979; 277(5696):491-492), (see Table 1 above). In particular embodiments, hydrophobicity is measured using the hydrophobicity scale reported in Engleman, et al.

The presence of a hydrophobic amino acid on the N- or C-terminus of a D-Arg or L-Arg, or a combination thereof, has also been found to improve the cytosolic uptake of the CPP (and the attached cargo). For example, in some embodiments, the CPPs disclosed herein may include $AA_{H1}$-D-Arg or D-Arg-$AA_{H1}$. In other embodiments, the CPPs disclosed herein may include $AA_{H1}$-L-Arg or L-Arg-$AA_{H1}$. In some embodiments, the presence of the hydrophobic amino acid on the N- or C-terminus of the D-Arg or L-Arg, or a combination thereof, in the CPP improves the cytosolic delivery efficiency by about 1.1 fold to about 30 fold, compared to an otherwise identical sequence, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold, inclusive of all values and subranges therebetween. In some embodiments, the presence of the hydrophobic amino acid on the N- and/or C-terminus of the D-Arg and/or L-Arg in the CPP improves the cytosolic uptake efficiency by about 20 fold.

The size of the hydrophobic amino acid on the N- or C-terminus of the D-Arg or an L-Arg, or a combination thereof (i.e., $AA_{H1}$), may be selected to improve cytosolic delivery efficiency of the CPP. For example, a larger hydrophobic amino acid on the N- or C-terminus of a D-Arg or L-Arg, or a combination thereof, improves cytosolic delivery efficiency compared to an otherwise identical sequence having a smaller hydrophobic amino acid. The size of the hydrophobic amino acid can be measured in terms of molecular weight of the hydrophobic amino acid, the steric effects of the hydrophobic amino acid, the solvent-accessible surface area (SASA) of the side chain, or combinations thereof. In some embodiments, the size of the hydrophobic amino acid is measured in terms of the molecular weight of the hydrophobic amino acid, and the larger hydrophobic amino acid has a side chain with a molecular weight of at least about 90 g/mol, or at least about 130 g/mol, or at least about 141 g/mol. In particular embodiments, the size of the amino acid is measured in terms of the SASA of the hydrophobic side chain, and the larger hydrophobic amino acid has a side chain with a SASA greater than that of alanine, or greater than that of glycine. In other embodiments, $AA_{H1}$ has a hydrophobic side chain with a SASA greater than or equal to about piperidine-2-carboxylate, greater than or equal to about tryptophan, greater than or equal to about phenylalanine, or equal to or greater than about naphthylalanine. In some embodiments, $AA_{H1}$ and $AA_{H2}$ independently have a side with a SASA in the range of from about 200 Å$^2$ to about 1000 Å$^2$, e.g, about 250 Å$^2$, 300 Å$^2$, 350 Å$^2$, 400 Å$^2$, 450 Å$^2$, 500 Å$^2$, 550 Å$^2$, 650 Å$^2$, 700 Å$^2$, 750 Å$^2$, 800 Å$^2$, 850 Å$^2$, 900 Å$^2$, and about 950 Å$^2$, inclusive of all values and subranges therebetween.

In some embodiments, $AA_{H1}$ has a side chain with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, $AA_{H2}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the side chains of $AA_{H1}$ and $AA_{H2}$ have a combined SASA of at least about 350 Å$^2$, at least about 360 Å$^2$, at least about 370 Å$^2$, at least about 380 Å$^2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å$^2$, at least about 510 Å$^2$, at least about 520 Å$^2$, at least about 530 Å$^2$, at least about 540 Å$^2$, at least about 550 Å$^2$, at least about 560 Å$^2$, at least about 570 Å$^2$, at least about 580 Å$^2$, at least about 590 Å$^2$, at least about 600 Å$^2$, at least about 610 Å$^2$, at least about 620 Å$^2$, at least about 630 Å$^2$, at least about 640 Å$^2$, greater than about 650 Å$^2$, at least about 660 Å$^2$, at least about 670 Å$^2$, at least about 680 Å$^2$, at least about 690 Å$^2$, or at least about 700 Å$^2$. In some embodiments, $AA_{H2}$ is a hydrophobic amino acid with a side chain having a SASA that is less than or equal to the SASA of the hydrophobic side chain of $AAH_1$. By way of example, and not by limitation, a CPP having a Nal-Arg motif exhibits improved cytosolic delivery efficiency compared to an otherwise identical CPP having a Phe-Arg motif; a CPP having a Phe-Nal-Arg motif exhibits improved cytosolic delivery efficiency compared to an otherwise identical CPP having a Nal-Phe-Arg motif; and a phe-Nal-Arg motif exhibits improved cytosolic delivery efficiency compared to an otherwise identical CPP having a nal-Phe-Arg motif. In some embodiments, the presence of the larger hydrophobic amino acid on the N- or C-terminus of the D-Arg or L-Arg, or a combination thereof, in the CPP improves cytosolic delivery efficiency by about 1.1 fold to about 30 fold, compared to an otherwise identical sequence, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold, inclusive of all values and subranges therebetween. In particular embodiments, the presence of the larger hydrophobic amino acid on the N- and/or C-terminus of the D-Arg and/or L-Arg in the CPP improves the cytosolic uptake efficiency by about 20 fold.

As used herein, "hydrophobic surface area" or "SASA" refers to the surface area (reported as square Ångstroms; Å$^2$) of an amino acid side chain that is accessible to a solvent. In particular embodiments, SASA is calculated using the 'rolling ball' algorithm developed by Shrake & Rupley (*J Mol Biol.* 79 (2): 351-71), which is herein incorporated by reference in its entirety for all purposes. This algorithm uses a "sphere" of solvent of a particular radius to probe the surface of the molecule. A typical value of the sphere is 1.4 Å, which approximates to the radius of a water molecule.

SASA values for certain side chains are shown below in Table 3. In certain embodiments, the SASA values described herein are based on the theoretical values listed in Table 3 below, as reported by Tien, et al. (PLOS ONE 8(11): e80635. https://doi.org/10.1371/journal.pone.0080635), which is herein incorporated by reference in its entirety for all purposes.

TABLE 3

| Residue | Theoretical | Empirical | Miller et al. (1987) | Rose et al. (1985) |
|---|---|---|---|---|
| Alanine | 129.0 | 121.0 | 113.0 | 118.1 |
| Arginine | 274.0 | 265.0 | 241.0 | 256.0 |
| Asparagine | 195.0 | 187.0 | 158.0 | 165.5 |
| Aspartate | 193.0 | 187.0 | 151.0 | 158.7 |
| Cysteine | 167.0 | 148.0 | 140.0 | 146.1 |
| Glutamate | 223.0 | 214.0 | 183.0 | 186.2 |
| Glutamine | 225.0 | 214.0 | 189.0 | 193.2 |
| Glycine | 104.0 | 97.0 | 85.0 | 88.1 |
| Histidine | 224.0 | 216.0 | 194.0 | 202.5 |
| Isoleucine | 197.0 | 195.0 | 182.0 | 181.0 |
| Leucine | 201.0 | 191.0 | 180.0 | 193.1 |
| Lysine | 236.0 | 230.0 | 211.0 | 225.8 |
| Methionine | 224.0 | 203.0 | 204.0 | 203.4 |
| Phenylalanine | 240.0 | 228.0 | 218.0 | 222.8 |
| Proline | 159.0 | 154.0 | 143.0 | 146.8 |
| Serine | 155.0 | 143.0 | 122.0 | 129.8 |
| Threonine | 172.0 | 163.0 | 146.0 | 152.5 |
| Tryptophan | 285.0 | 264.0 | 259.0 | 266.3 |
| Tyrosine | 263.0 | 255.0 | 229.0 | 236.8 |
| Valine | 174.0 | 165.0 | 160.0 | 164.5 |

The chirality of the amino acids (i.e., D or L amino acids) can be selected to improve cytosolic delivery efficiency of the CPP (and the attached cargo as described below). In some embodiments, the hydrophobic amino acid on the N- or C-terminus of an arginine (e.g., $AA_{H1}$, $AA_u$ or $AA_z$) has the same or opposite chirality as the adjacent arginine. In some embodiments, $AA_{H1}$ has the same chirality as the adjacent arginine. For example, when the arginine is D-arg (i.e. "r"), $AA_{H1}$ is a D-$AA_{H1}$, and when the arginine is L-Arg (i.e., "R"), $AA_{H1}$ is a L-$AA_{H1}$. Accordingly, in some embodiments, the CPPs disclosed herein may include at least one of the following motifs: D-$AA_{H1}$-D-arg, D-arg-D-$AA_{H1}$, L-$AA_{H1}$-L-Arg, or L-Arg-L$AA_{H1}$. In some embodiments, the presence of the hydrophobic amino acid having the same chirality as the adjacent arginine improves cytosolic delivery efficiency by about 1.1 fold to about 30 fold, compared to an otherwise identical sequence, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold inclusive of all values and subranges therebetween. In some embodiments, the presence of the hydrophobic amino acid having the same chirality as the adjacent arginine improves the cytosolic uptake efficiency by about 2.5 fold.

As discussed above, the disclosure provides for various modifications to a cyclic peptide sequence which may improve cytosolic delivery efficiency. In some embodiments, improved cytosolic uptake efficiency can be measured by comparing the cytosolic delivery efficiency of the CPP having the modified sequence to a proper control sequence. In some embodiments, the control sequence does not include a particular modification (e.g., matching chirality of R and $AA_{H1}$) but is otherwise identical to the modified sequence. In other embodiments, the control has the following sequence: cyclic(FΦRRRRQ)

As used herein cytosolic delivery efficiency refers to the ability of a CPP to traverse a cell membrane and enter the cytosol. In some embodiments, cytosolic delivery efficiency of the CPP is not dependent on a receptor or a cell type. Cytosolic delivery efficiency can refer to absolute cytosolic delivery efficiency or relative cytosolic delivery efficiency.

Absolute cytosolic delivery efficiency is the ratio of cytosolic concentration of a cCPP (or a cCPP-cargo conjugate) over the concentration of the cCPP (or the cCPP-cargo conjugate) in the growth medium. Relative cytosolic delivery efficiency refers to the concentration of a cCPP in the cytosol compared to the concentration of a control cCPP in the cytosol. Quantification can be achieved by fluorescently labeling the cCPP (e.g., with a FTIC dye) and measuring the fluorescence intensity using techniques well-known in the art.

In particular embodiments, relative cytosolic delivery efficiency is determined by comparing (i) the amount of a cCPP of the invention internalized by a cell type (e.g., HeLa cells) to (ii) the amount of the control cCPP internalized by the same cell type. To measure relative cytosolic delivery efficiency, the cell type may be incubated in the presence of a cCPP of the invention for a specified period of time (e.g., 30 minutes, 1 hour, 2 hours, etc.) after which the amount of the cCPP internalized by the cell is quantified using methods known in the art, e.g., fluorescence microscopy. Separately, the same concentration of the control cCPP is incubated in the presence of the cell type over the same period of time, and the amount of the control cCPP internalized by the cell is quantified.

In other embodiments, relative cytosolic delivery efficiency can be determined by measuring the $IC_{50}$ of a cCPP having a modified sequence for an intracellular target, and comparing the $IC_{50}$ of the cCPP having the modified sequence to a proper control sequence (as described herein).

In some embodiments, the relative cytosolic delivery efficiency of the CPPs described herein is in the range of from about 50% to about 450% compared to cyclo (FΦRRRRQ), e.g., about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 510%, about 520%, about 530%, about 540%, about 550%, about 560%, about 570%, about 580%, or about 590%, inclusive of all values and subranges therebetween. In other embodiments, the relative cytosolic delivery efficiency of the CPPs described herein is improved by greater than about 600% compared to cyclo(FΦRRRRQ).

In other embodiments, the absolute cytosolic delivery efficacy of from about 40% to about 100%, e.g., about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, inclusive of all values and subranges therebetween.

In some embodiments, the cCPPs disclosed herein (e.g., Formulae I, I-A to I-F, and Formula IV-A to IV-F) are selected from the sequences provided in Table 4 below.

TABLE 4

| | | | | | Cellular Entry Efficiency[b] | |
|---|---|---|---|---|---|---|
| | | SEQ. ID. | Molecular Mass | | In 10% | In 1% |
| Peptide | Sequence[a] | NO. | Calcd | Obsd | FBS | FBS |
| CPP1 | cyclo(FΦRRRRQ) | 58 | 1827.86 | 1828.837 | 21 | |
| CPP9 | cyclo(fΦRrRrQ) | 59 | 1827.86 | 1828.778 | 94 ± 7 | 32 ± 6 |
| CPP12 | cyclo(FfΦRrRrQ) | 60 | 1974.93 | 1975.839 | 100 | 100 |
| CPP1-1 | cyclo($F^{tBU}$RRRRQ) | 61 | 1686.84 | 1687.868 | 6.7 ± 0.4 | |
| CPP1-2 | cyclo($Dap^{Hexan}$RRRRQ) | 62 | 1667.83 | 1668.816 | 2.9 ± 0.2 | |
| CPP1-3 | cyclo($Dap^{Octan}$RRRRQ) | 63 | 1696.86 | 1696.889 | 5.7 ± 0.6 | |
| CPP1-4 | cyclo($Dap^{Deca}$RRRRQ) | 64 | 1723.89 | 1746.906 | 57 ± 19 | |
| CPP1-5 | cyclo($Dap^{1\text{-}Pyren}$RRRRQ) | 65 | 1797.82 | 1798.836 | 10 ± 20 | |
| CPP1-6 | cyclo($Dap^{3,3\text{-}diphenyl}$RRRRQ) | 66 | 1706.81 | 1707.834 | 3.9 ± 0.4 | |
| CPP1-7 | cyclo($Dap^{Fmoc}$RRRRQ) | 67 | 1791.83 | 1792.861 | 17 ± 1 | |
| CPP1-8 | cyclo($Dap^{1\text{-}Pyreneb}$RRRRQ) | 68 | 1839.86 | 1840.907 | 24 ± 1 | |
| CPP1-9 | Not synthesized | | | | | |
| CPP1-10 | cyclo($Dap^{Deca}$RrRrQ) | 69 | 1723.89 | 1724.923 | 21 ± 9 | 24 |
| CPP1-11 | cyclo($Dap^{Deca}$rRrRQ) | 70 | 1723.89 | 1724.895 | 20 ± 6 | 29 |

TABLE 4-continued

| Peptide | Sequence[a] | SEQ. ID. NO. | Molecular Mass Calcd | Molecular Mass Obsd | Cellular Entry Efficiency[b] In 10% FBS | Cellular Entry Efficiency[b] In 1% FBS |
|---|---|---|---|---|---|---|
| CPP1-12 | cyclo(Dap$^{Deca}$ARRRQ) | 71 | 1638.83 | 1639.834 | 26 ± 4 | 34 |
| CPP1-13 | cyclo(Dap$^{Deca}$RRRAQ) | 72 | 1638.83 | 1639.824 | 32 ± 2 | 33 |
| CPP1-14 | cyclo(Dap$^{Deca}$RRRRRQ) | 73 | 1880.00 | 1880.979 | 12 ± 1 | 21 |
| CPP1-15 | cyclo(Lys$^{Deca}$RRRRQ) | 74 | 1765.94 | 1767.638 | 76 ± 21 | 44 ± 11 |
| CPP1-16 | cyclo(Dap$^{Deca}$RRRQ) | 75 | 1567.79 | 1568.692 | 3.0 ± 0.1 | 25 |
| CPP1-17 | cyclo(Orn$^{Deca}$RRRRQ) | 76 | 1751.93 | 1752.832 | 115 ± 32 | 58 ± 22 |
| CPP1-18 | cyclo(Lys$^{Deca}$RrRrQ) | 77 | 1765.94 | 1766.908 | 31 | |
| CPP1-19 | cyclo(Lys$^{Deca}$rRrRQ) | 78 | 1765.94 | 1766.880 | 12 | |
| CPP1-20 | cyclo(Asp$^{Decy}$RRRRQ) | 79 | 1737.91 | 1738.830 | 281 ± 59 | 94 ± 41 |
| CPP1-22 | cyclo(Asp$^{Decy}$RrRrQ) | 80 | 1737.91 | 1738.844 | 11 | |
| CPP1-23 | cyclo(Glu$^{Decy}$RrRrQ) | 81 | 1751.93 | 1752.833 | 1.4 | |
| CPP1-24 | cyclo(Asp$^{Decy}$rRrRQ) | 82 | 1737.91 | 1738.854 | 8.6 | |
| CPP1-25 | cyclo(Glu$^{Decy}$rRrRQ) | 83 | 1751.93 | 1752.837 | 34 | |

[a]Single-letter codes for amino acids. Φ, 2-naphthylalanine. tBu = tert-butanoyl, hexan = hexanoyl, octan = octanoyl, deca = decanoyl, 1-pyren = pyrenoyl, 3,3-diphenyl = 3,3-diphenoyl, Fmoc = fluorenylmethyloxycarbonoyl, 1-pyreneb = 1-pyrenylbutanoyl, decy =decynoyl
[b]All values are relative to that of CPP12 (100%).

In particular embodiments, the cCCPs disclosed herein have the following structure:

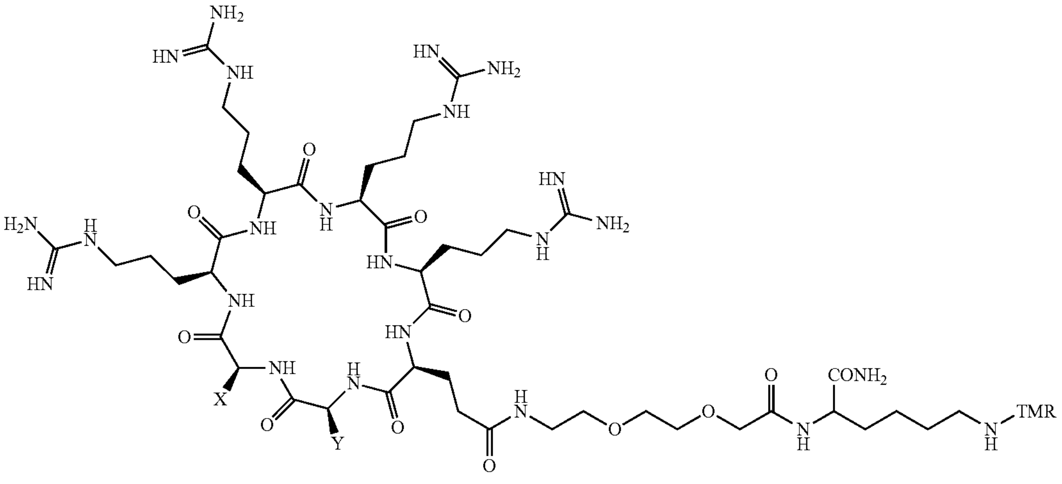

or NF wherein X is selected from:
CPP1-1
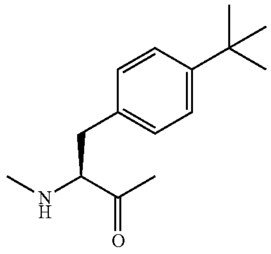
1-2
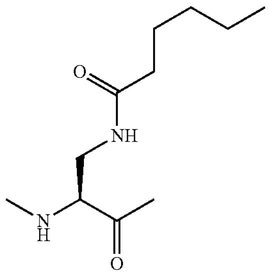
1-3
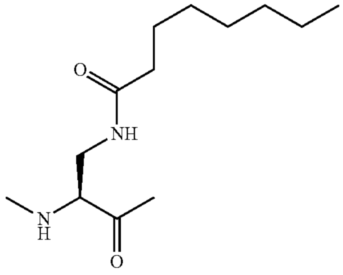
1-4
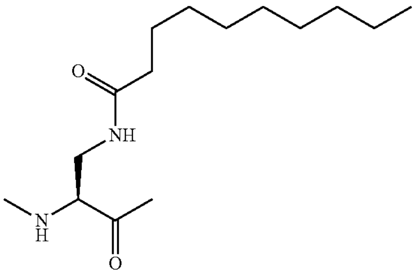
-continued
1-5
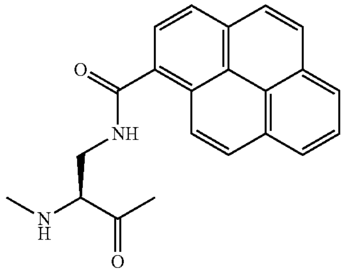
1-6
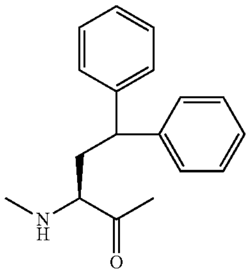
1-7
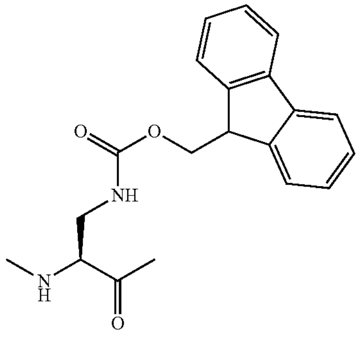
1-8
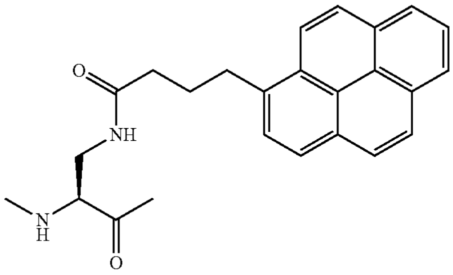,
wherein the amino acid bearing Y is absent.

In some embodiments, the cCPPs disclosed herein (e.g., Formulae I, I-A to I-F, IV-A to IV-F) are selected from:
CPP1-10
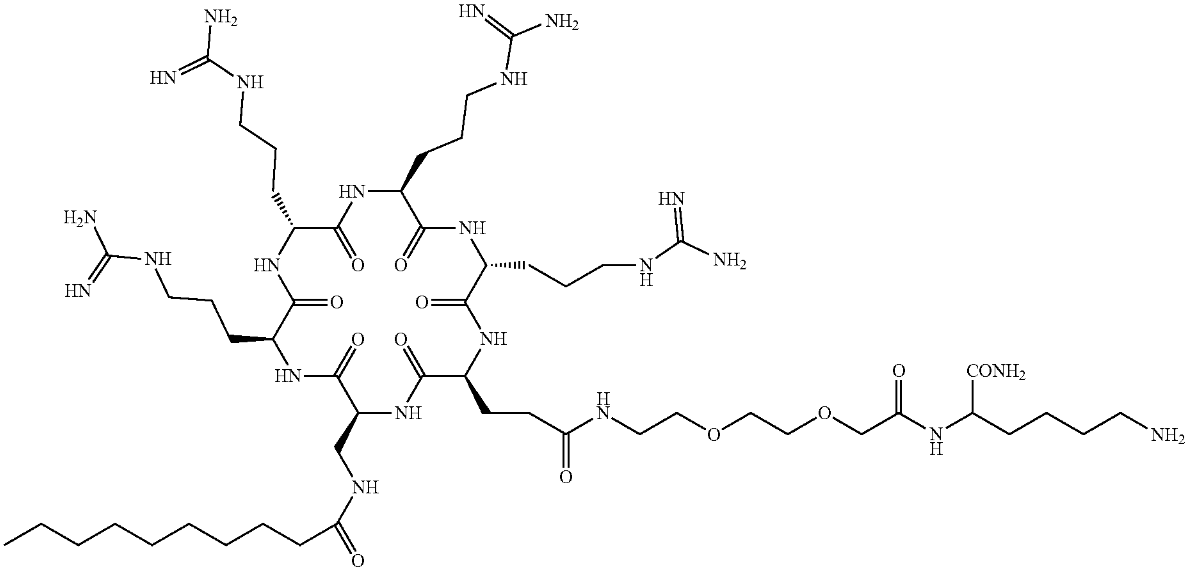
1265.82
CPP1-11
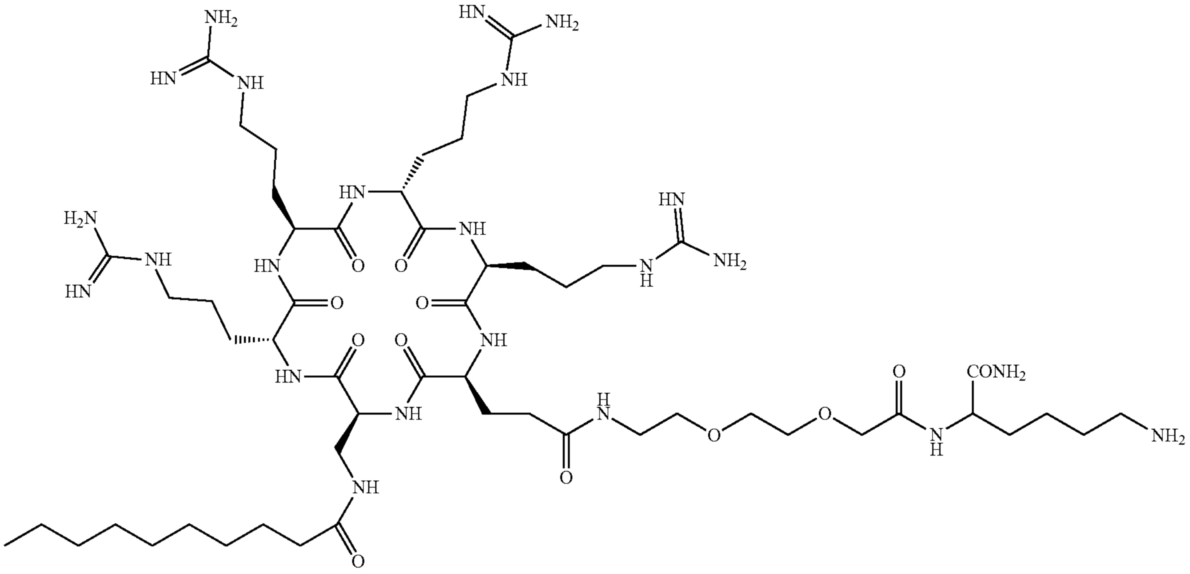
1265.82

-continued
CPP1-13
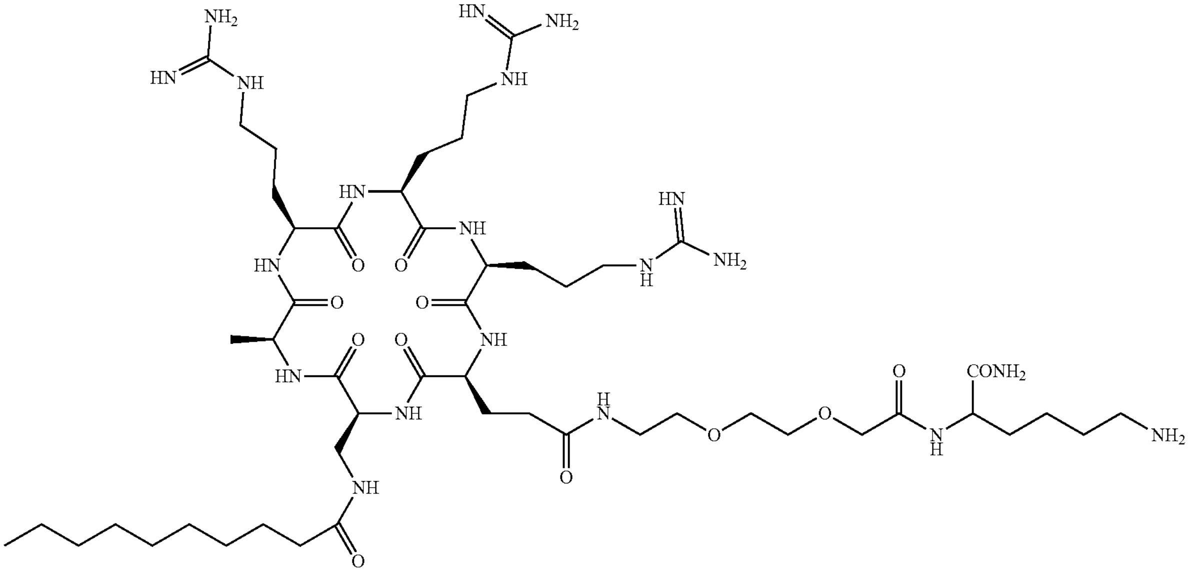
1180.75
CPP1-12
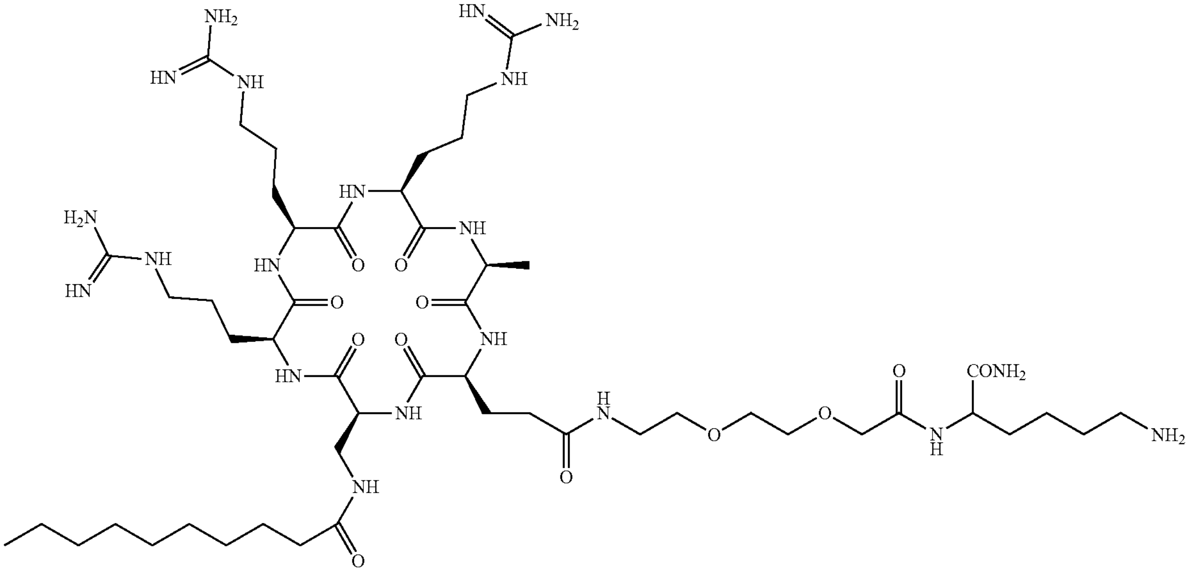
1180.75

-continued
CPP1-14
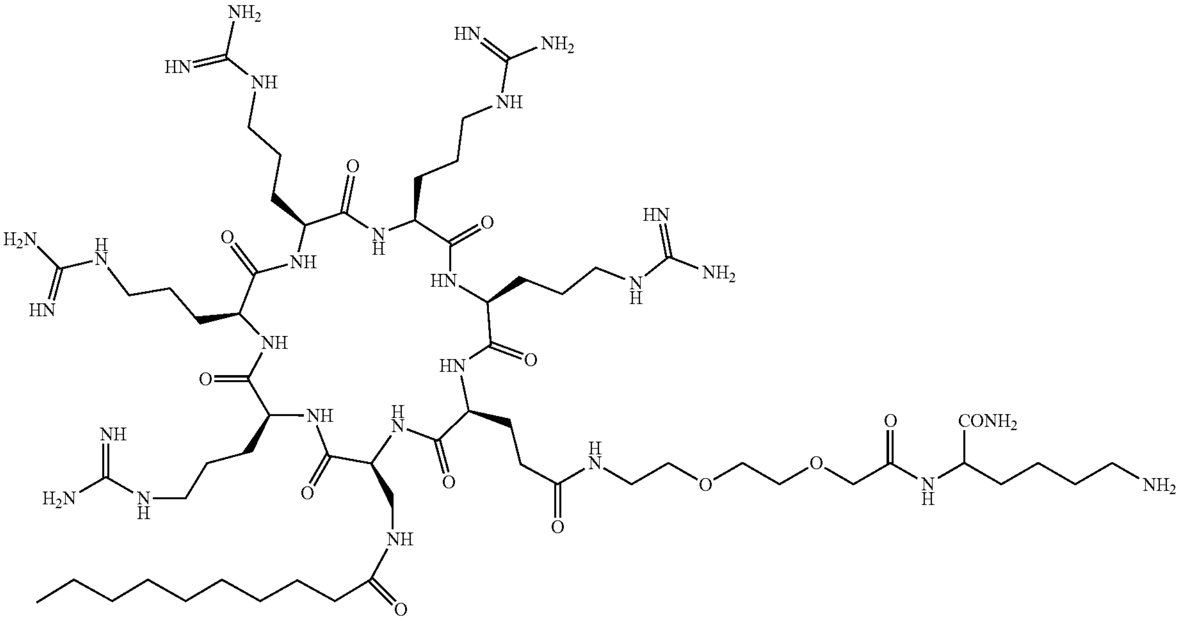
1421.92
CPP1-15
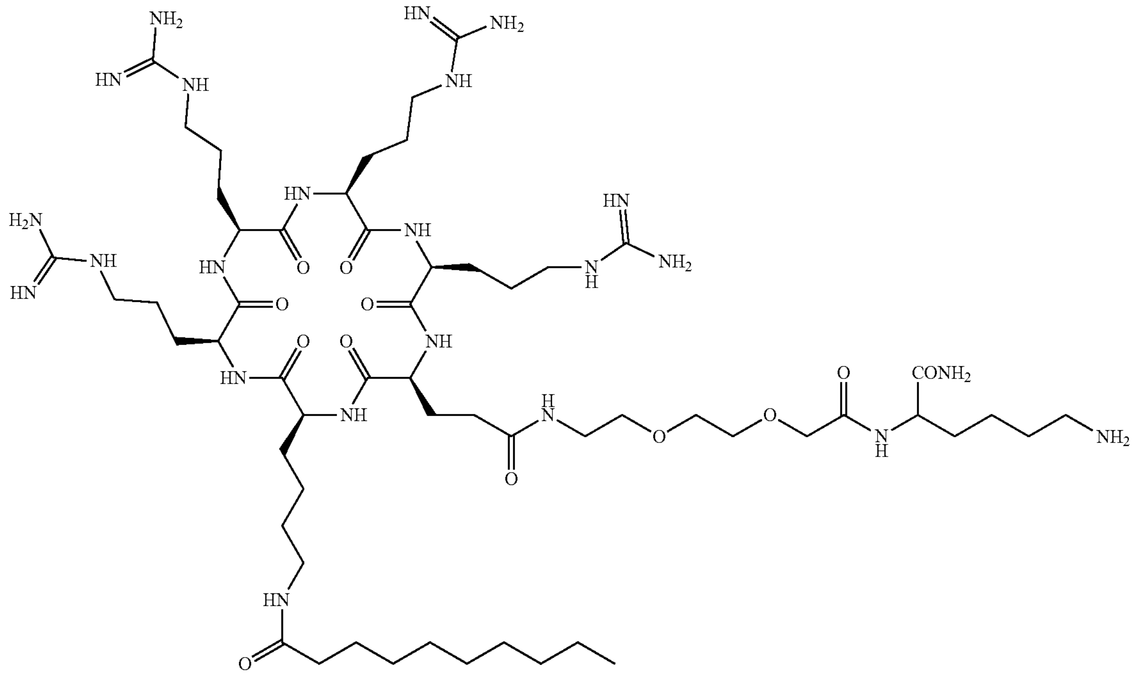
1307.96

-continued
CPP1-16
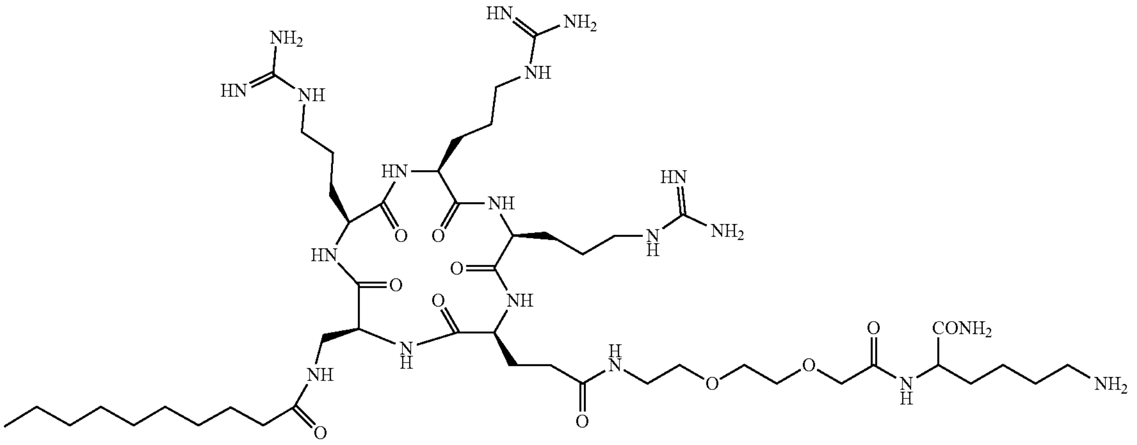
1109.71
CPP1-17
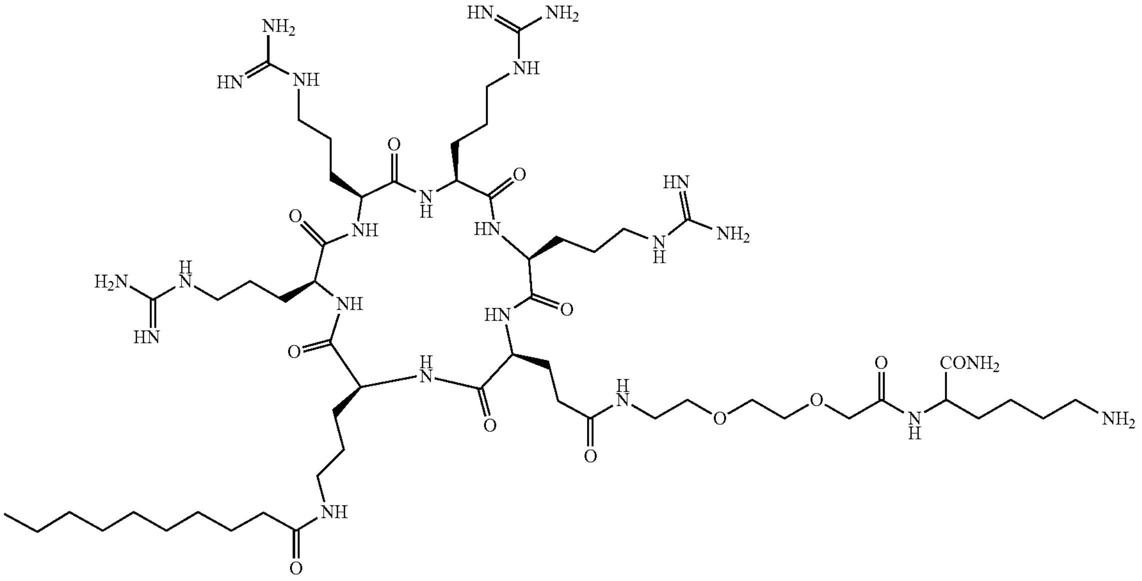
1293.85

-continued
CPP1-18
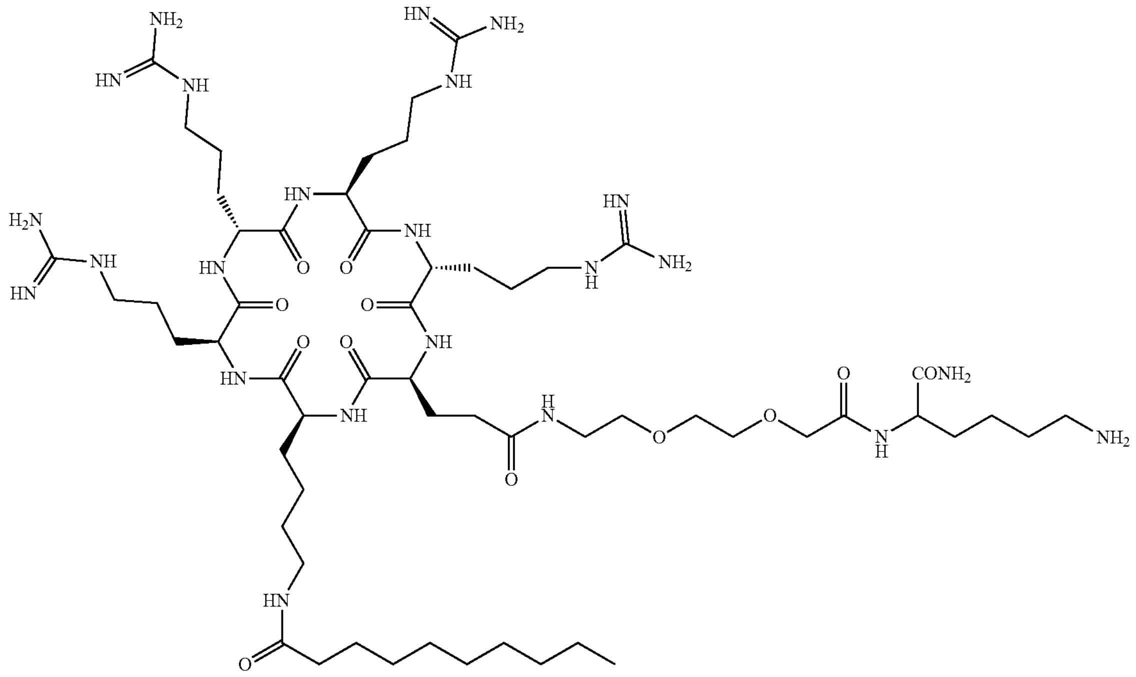
1307.86
CPP1-19
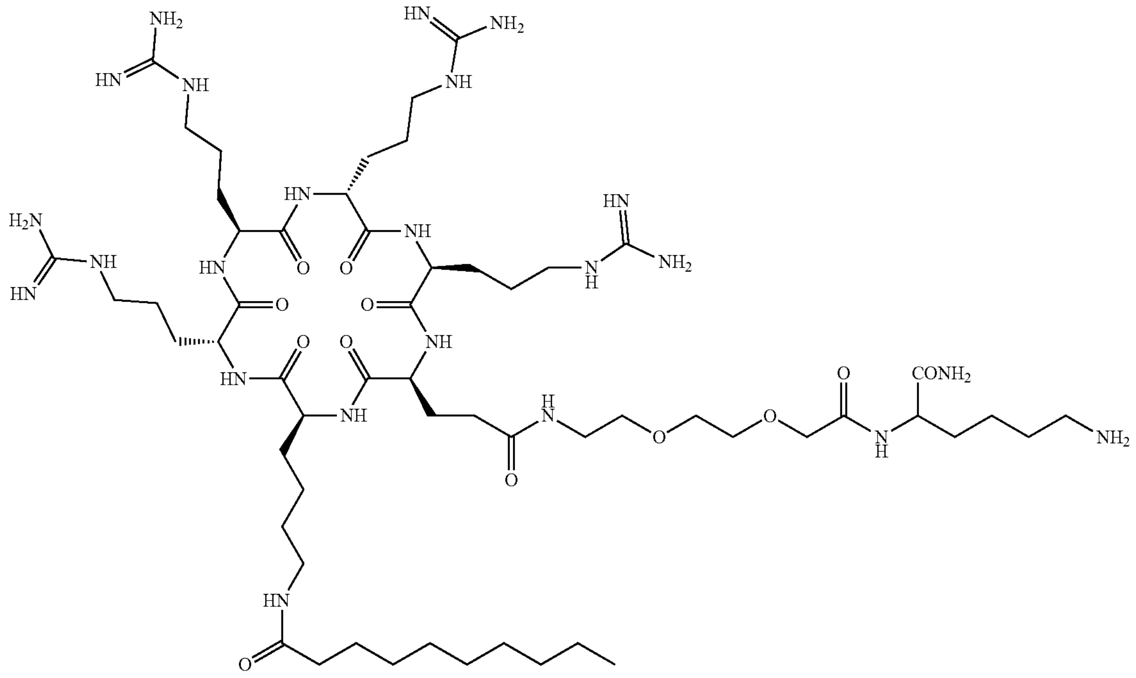
1307.86

-continued
CPP1-20
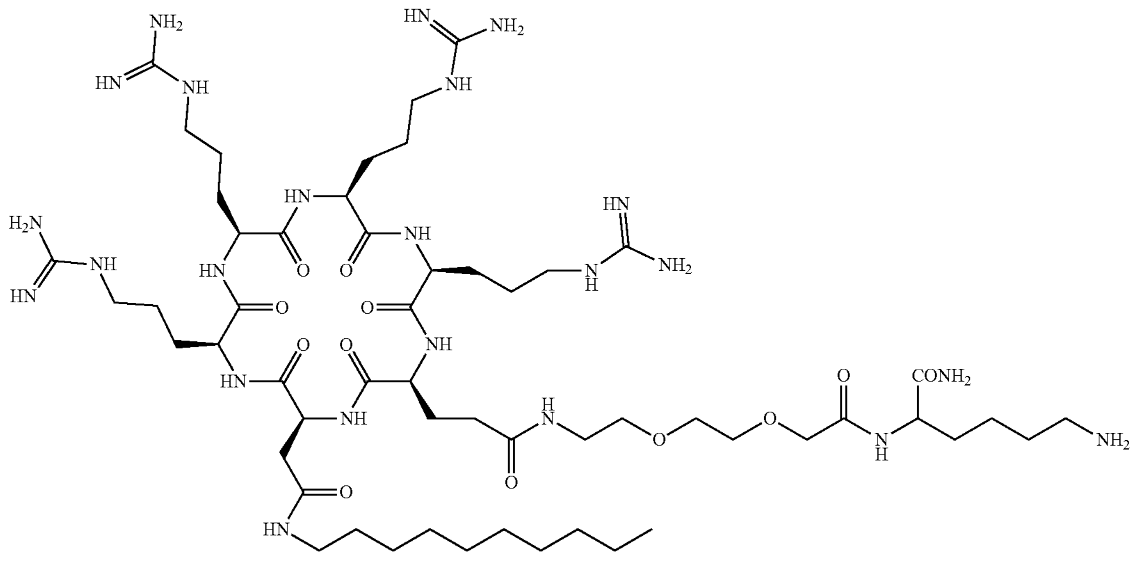
1279.83
CPP1-21
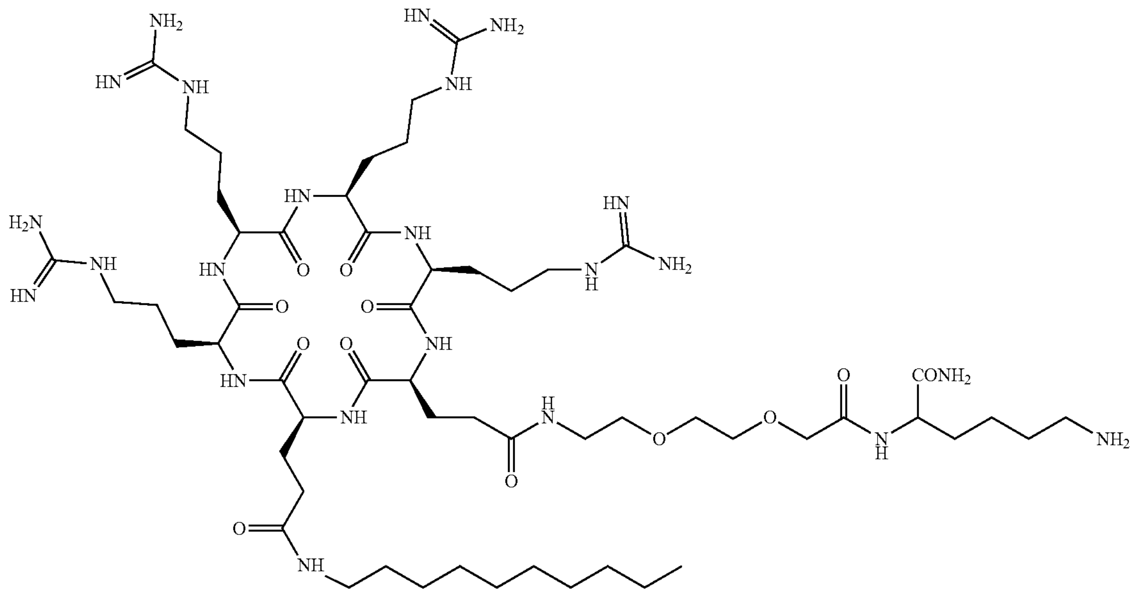
1293.85

CPP1-22
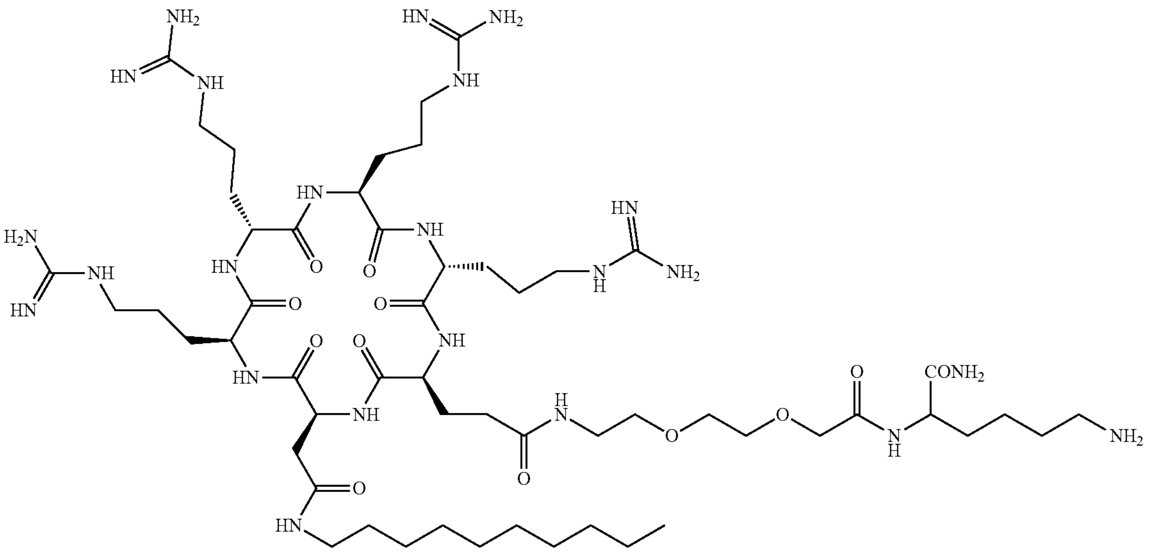
1279.83
CPP1-23
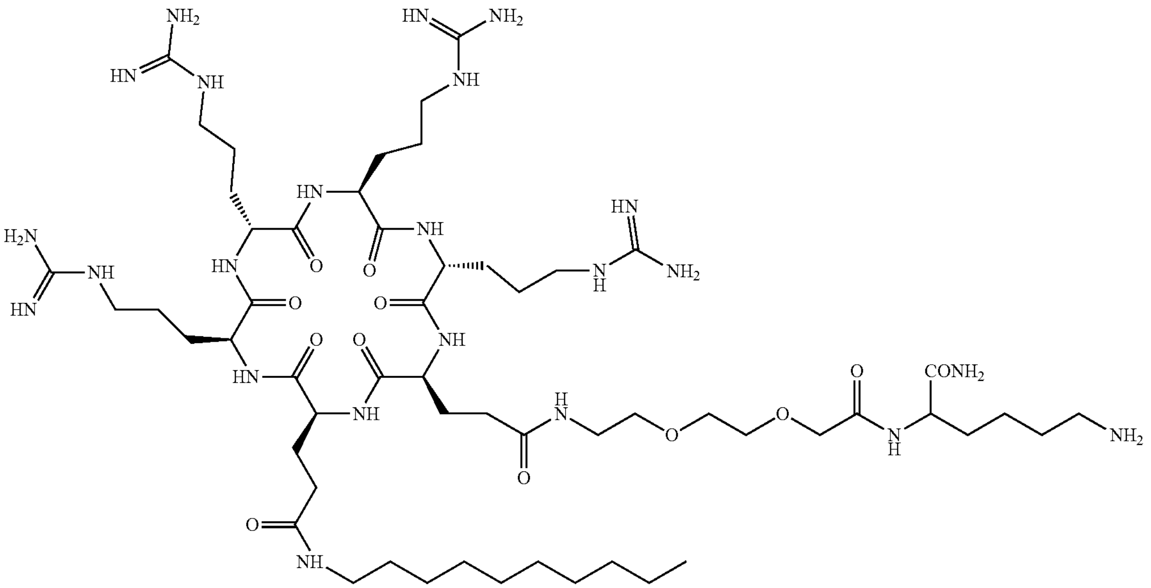
1293.85

-continued

CPP1-24

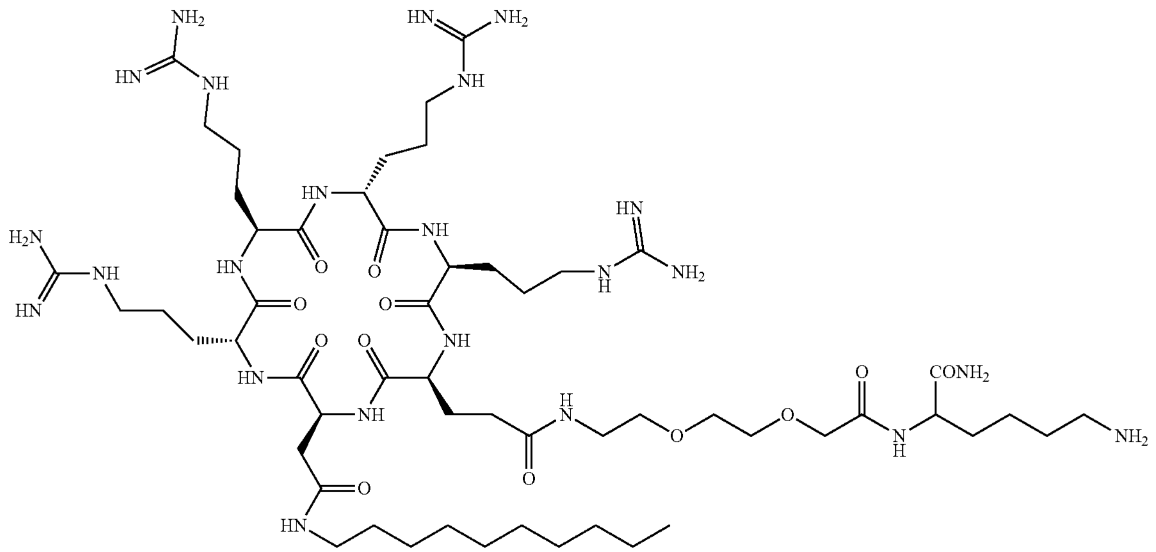

1279.83

CPP1-25

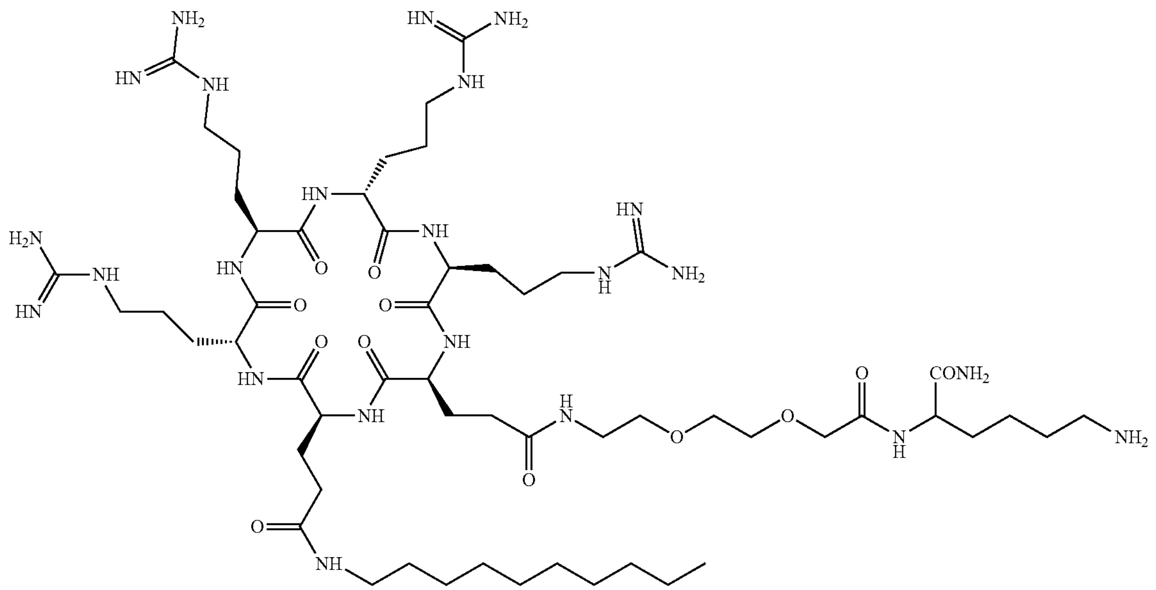

1293.85

Cargo

In some embodiments, the CPPs disclosed herein can further include a cargo moiety, which may comprise a peptide. The cargo moiety can comprise one or more detectable moieties, one or more therapeutic moieties, one or more targeting moieties, or any combination thereof. In some embodiments, the cargo moiety may be a peptide sequence or a non-peptidyl therapeutic agent. In some embodiments, the cargo moiety can be coupled to an amino group (e.g., N-terminus), a carboxylate group (e.g., C-terminus), or a side chain of one or more amino acids in the cCPP. In some embodiments, the cCPP and the cargo moiety together are cyclic (referred to herein as "endocyclic"). In the endocyclic system, the cargo moiety may be located between amino acids of the cCPP. In some embodiments, the cargo moiety independently forms a peptide bond with each of the adjacent amino acids. In some embodiments, the cCPP is cyclic and the cargo moiety is appended to the cyclic cell penetrating peptide moiety structure (referred to herein as "exocyclic"). In some embodiments, the cargo moiety is cyclic and the cCPP is cyclic, and together they form a bicyclic system (referred to herein as "bicyclic").

In some embodiments, the cCPP further comprises a linker group ("L"), and the cargo is attached to the linker group, forming a bicyclic cCPP and cargo moiety. In certain embodiments, the cCPP further comprises a linker group ("L"), and cargo is attached to the linker group and a side chain of an amino acid of the CPP, forming a bicyclic cCPP and cargo moiety. Examples of linkers used to form a bicyclic include trimesic acid or nitrilotriacetic acid, as described in U.S. Patent App. Pub. 2016/0115202, which is herein incorporated by reference in its entirety for all purposes.

It is also disclosed herein that for the endocyclic structure, some amino acids in the CPP can also be part of the cargo moity. For example, a peptide pentrating moiety FNalRR can be formed from FNal and a cargo moiety comprising two Args. In this case, the two Arg residues perform dual functions. Thus, in some cases the sequence of the cargo moiety is taken into account when referring to the peptide penetrating moiety.

Cargo Moiety

The cargo moiety can comprise any cargo of interest, for example a linker moiety, a detectable moiety, a therapeutic moiety, a targeting moiety, and the like, or any combination thereof. In some examples, the cargo moiety can comprise one or more additional amino acids (e.g., K, UK, TRV); a linker (e.g., bifunctional linker LC-SMCC); coenzyme A; phosphocoumaryl amino propionic acid (pCAP); 8-amino-3,6-dioxaoctanoic acid (miniPEG); L-2,3-diaminopropionic acid (Dap or J); L-β-naphthylalanine; L-pipecolic acid (Pip); sarcosine; trimesic acid; 7-amino-4-methylcourmarin (Amc); fluorescein isothiocyanate (FITC); L-2-naphthylalanine; norleucine; 2-aminobutyric acid; Rhodamine B (Rho); Dexamethasone (DEX); or combinations thereof.

In some examples the cargo moiety can comprise any of those listed in Table 5, or derivatives or combinations thereof.

TABLE 5

Example cargo moieties

| SEQ ID NO | Abbreviation | Sequence* |
|---|---|---|
| 1 | $R_5$ | RRRRR |
| 2 | $A_5$ | AAAAA |
| 3 | $F_4$ | FFFF |
| 4 | PCP | DE(pCAP)LI |
| 5 | $A_7$ | AAAAAAA |
| 6 | | RARAR |
| 7 | | DADAD |
| 8 | | DΩUD |
| 9 | | UTRV |
| 10 | | D-pThr-Pip-Nal |

*pCAP, phosphocoumaryl amino propionic acid; Ω, norleucine; U, 2-aminobutyric acid; D-pThr is D-phosphothreonine, Pip is L-piperidine-2-carboxylate.

Detectable Moiety

The detectable moiety can comprise any detectable label. Examples of suitable detectable labels include, but are not limited to, a UV-Vis label, a near-infrared label, a luminescent group, a phosphorescent group, a magnetic spin resonance label, a photosensitizer, a photocleavable moiety, a chelating center, a heavy atom, a radioactive isotope, a isotope detectable spin resonance label, a paramagnetic moiety, a chromophore, or any combination thereof. In some embodiments, the label is detectable without the addition of further reagents.

In some embodiments, the detectable moiety is a biocompatible detectable moiety, such that the compounds can be suitable for use in a variety of biological applications. "Biocompatible" and "biologically compatible", as used herein, generally refer to compounds that are, along with any metabolites or degradation products thereof, generally nontoxic to cells and tissues, and which do not cause any significant adverse effects to cells and tissues when cells and tissues are incubated (e.g., cultured) in their presence.

The detectable moiety can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris (4,7-diphenyl-1,10-phenanthroline) (Ru $(dpp)_3$); Ru (II) tris (1,10-phenanthroline) (Ru$(phen)_3$), tris(2,2'-bipyridine) rutheniurn (II) chloride hexahydrate (Ru$(bpy)_3$); erythrosine B; fluorescein; fluorescein isothiocyanate (FITC); eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitirophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxy-fluorecsein; carboxynaphthofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; dioctadecylcycloxacarbocyanine; fluorenylmethyloxycarbonyl chloride; 7-amino-4-methylcourmarin (Amc); green fluorescent protein (GFP); and derivatives or combinations thereof.

In some examples, the detectable moiety can comprise Rhodamine B (Rho), fluorescein isothiocyanate (FITC), 7-amino-4-methylcourmarin (Amc), green fluorescent protein (GFP), or derivatives or combinations thereof.

The detectible moiety can be attached to the cell penetrating peptide moiety at the amino group, the carboxylate group, or the side chain of any of the amino acids of the cell penetrating peptide moiety (e.g., at the amino group, the carboxylate group, or the side chain of any amino acid in the CPP).

Therapeutic Moiety

The disclosed compounds can also comprise a therapeutic moiety. In some examples, the cargo moiety comprises a therapeutic moiety. The detectable moiety can be linked to a therapeutic moiety or the detectable moiety can also serve as the therapeutic moiety. Therapeutic moiety refers to a group that when administered to a subject will reduce one or more symptoms of a disease or disorder.

The therapeutic moiety can comprise a wide variety of drugs, including antagonists, for example enzyme inhibitors, and agonists, for example a transcription factor which results in an increase in the expression of a desirable gene product (although as will be appreciated by those in the art, antagonistic transcription factors can also be used), are all included. In addition, therapeutic moiety includes those agents capable of direct toxicity and/or capable of inducing toxicity towards healthy and/or unhealthy cells in the body. Also, the therapeutic moiety can be capable of inducing and/or priming the immune system against potential pathogens.

The therapeutic moiety can, for example, comprise an anticancer agent, antiviral agent, antimicrobial agent, anti-inflammatory agent, immunosuppressive agent, anesthetics, or any combination thereof.

The therapeutic moiety can comprise an anticancer agent. Example anticancer agents include 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The therapeutic moiety can also comprise a biopharmaceutical such as, for example, an antibody.

In some examples, the therapeutic moiety can comprise an antiviral agent, such as ganciclovir, azidothymidine (AZT), lamivudine (3TC), etc.

In some examples, the therapeutic moiety can comprise an antibacterial agent, such as acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; Lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin; oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillin G benzathine; penicillin G potassium; penicillin G procaine; penicillin G sodium; penicillin V; penicillin V benzathine; penicillin V hydrabamine; penicillin V potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin B sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; or zorbamycin.

In some examples, the therapeutic moiety can comprise an anti-inflammatory agent.

In some examples, the therapeutic moiety can comprise dexamethasone (Dex).

In other examples, the therapeutic moiety comprises a therapeutic protein. For example, some people have defects in certain enzymes (e.g., lysosomal storage disease). It is disclosed herein to deliver such enzymes/proteins to human cells by linking to the enzyme/protein to one of the disclosed cell penetrating peptides. The disclosed cell penetrating peptides have been tested with proteins (e.g., GFP, PTP1B, actin, calmodulin, troponin C) and shown to work.

In some examples, the therapeutic moiety comprises a targeting moiety. The targeting moiety can comprise, for example, a sequence of amino acids that can target one or more enzyme domains. In some examples, the targeting moiety can comprise an inhibitor against an enzyme that can play a role in a disease, such as cancer, cystic fibrosis, diabetes, obesity, or combinations thereof. For example, the targeting moiety can comprise any of the sequences listed in Table 6.

TABLE 6

Example targeting moieties

| SEQ ID NO | Abbreviation * | Sequence |
|---|---|---|
| 11 | PΘGΛYR | Pro-Pip-Gly-$F_2$Pmp-Tyr-Arg |
| 12 | SΘIΛΛR | Ser-Pip-Ile-$F_2$Pmp-$F_2$Pmp-Arg |
| 13 | IHIΛIR | Ile-His-Ile-$F_2$Pmp-Ile-Arg |

TABLE 6-continued

| Example targeting moieties | | |
|---|---|---|
| SEQ ID NO | Abbreviation * | Sequence |
| 14 | AaIΛΘR | Ala-(D-Ala)-Ile-$F_2$Pmp-Pip-Arg |
| 15 | ΣSΘΛvR | Fpa-Ser-Pip-$F_2$Pmp-(D-Val)-Arg |
| 16 | ΘnPΛAR | Pip-(D-Asn)-Pro-$F_2$Pmp-Ala-Arg |
| 17 | TΨAΛGR | Tyr-Phg-Ala-$F_2$Pmp-Gly-Arg |
| 18 | AHIΛaR | Ala-His-Ile-$F_2$Pmp-(D-Ala)-Arg |
| 19 | GnGΛpR | Gly-(D-Asn)-Gly-$F_2$Pmp-(D-Pro)-Arg |
| 20 | fQΘΛIR | (D-Phe)-Gln-Pip-$F_2$Pmp-Ile-Arg |
| 21 | SPGΛHR | Ser-Pro-Gly-$F_2$Pmp-His-Arg |
| 22 | ΘYIΛHR | Pip-Tyr-Ile-$F_2$Pmp-His-Arg |
| 23 | SvPΛHR | Ser-(D-Val)-Pro-$F_2$Pmp-His-Arg |
| 24 | AIPΛnR | Ala-Ile-Pro-$F_2$Pmp-(D-Asn)-Arg |
| 25 | ESIΛQF | Fpa-Ser-Ile-$F_2$Pmp-Gln-Arg |
| 26 | AaΨΛfR | Ala-(D-Ala)-Phg-$F_2$Pmp-(D-Phe)-Arg |
| 27 | ntΨΛΨR | (D-Asn)-(D-Thr)-Phg-$F_2$Pmp-Phg-Arg |
| 28 | IPΨΛΩN | Ile-Pro-Phg-$F_2$Pmp-Nle-Arg |
| 29 | QΘΣΛΘR | Gln-Pip-Fpa-$F_2$Pmp-Pip-Arg |
| 30 | nAΣΛGR | (D-Asn)-Ala-Fpa-$F_2$Pmp-Gly-Arg |
| 31 | ntYΛAR | (D-Asn)-(D-Thr)-Tyr-$F_2$Pmp-Ala-Arg |
| 32 | eAYΛvR | (D-Glu)-Ala-Phg-$F_2$Pmp-(D-Val)-Arg |
| 33 | IvΨ'AAR | Ile-(D-Val)-Phg-$F_2$Pmp-Ala-Arg |
| 34 | YtΨ'AAR | Tyr-(D-Thr)-Phg-$F_2$Pmp-Ala-Arg |
| 35 | nΘΨAIR | (D-Asn)-Pip-Phg-$F_2$Pmp-Ile-Arg |
| 36 | ΘnWAHR | Pip-(D-Asn)-Trp-$F_2$Pmp-His-Arg |
| 37 | YΘvΛIR | Tyr-Pip-(D-Val)-$F_2$Pmp-Ile-Arg |
| 38 | nSAΛGR | (D-Asn)-Ser-(D-Ala)-$F_2$Pmp-Gly-Arg |
| 39 | tnvΛaR | (D-Thr)-(D-Asn)-(D-Val)-$F_2$Pmp-(D-Ala)-Arg |
| 40 | ntvΛtR | (D-Asn)-(D-Thr)-(D-Val)-$F_2$Pmp-(D-Thr)-Arg |
| 41 | SItΛYR | Ser-Ile-(D-Thr)-$F_2$Pmp-Tyr-Arg |
| 42 | nΣnΛIR | (D-Asn)-Fpa-(D-Asn)-$F_2$Pmp-(D-Leu)-Arg |
| 43 | YnnΛΩR | Tyr-(D-Asn)-(D-Asn)-$F_2$Pmp-Nle-Arg |
| 44 | nYnΛGR | (D-Asn)-Tyr-(D-Asn)-$F_2$Pmp-Gly-Arg |
| 45 | AWnΛAR | Ala-Trp-(D-Asn)-$F_2$Pmp-Ala-Arg |
| 46 | vtHΛYR | (D-Val)-(D-Thr)-His-$F_2$Pmp-Tyr-Arg |
| 47 | PΨHΛΘR | Pro-Phg-His-$F_2$Pmp-Pip-Arg |
| 48 | nΨHΛGR | (D-Asn)-Phg-His-$F_2$Pmp-Gly-Arg |
| 49 | PAHΛGR | Pro-Ala-His-$F_2$Pmp-Gly-Arg |
| 50 | AYHΛIR | Ala-Tyr-His-$F_2$Pmp-Ile-Arg |
| 51 | nΘeΛYR | (D-Asn)-Pip-(D-Glu)-$F_2$Pmp-Tyr-Arg |

TABLE 6-continued

Example targeting moieties

| SEQ ID NO | Abbreviation * | Sequence |
|---|---|---|
| 52 | vSSΛtR | (D-Val)-Ser-Ser-$F_2$Pmp-(D-Thr)-Arg |
| 53 | aΞt' ϑΦ'YNK | ((D-Ala)-Sar-(D-pThr)-Pp-Nal-Tyr-Gln)-Lys |
| 54 | Tm(aΞt'ϑΦ'RA)Dap | Tm((D-Ala)-Sar-(D-pThr)-Pp-Nal-Arg-Ala)-Dap |
| 55 | Tm(aΞt'ϑΦ'RAa)Dap | Tm((D-Ala)-Sar-(D-pThr)-Pp-Nal-Arg-Ala-(D-Ala))-Dap |
| 56 | Tm(aΞtϑΦ'RAa)Dap | Tm((D-Ala)-Sar-(D-Thr)-Pp-Nal-Arg-Ala-(D-Ala))-Dap |
| 57 | Tm(aΞtaΦ'RAa)Dap | Tm((D-Ala)-Sar-(D-Thr)-(D-Ala)-Nal-Arg-Ala-(D-Ala))-Dap |

* Fpa, Σ: L-4-fluorophenylalanine; Pip, Θ: L-homoproline; Nle, Ω: L-norleucine; Phg, Ψ L-phenylglycine; F2Pmp, Λ: L-4-(phosphonodifluoromethyl)phenylalanine; Dap, L-2,3-diaminopropionic acid; Nal, Φ': L-β-naphthylalanine; Pp, ϑ: L-pipecolic acid; Sar, Ξ: sarcosine; Tm, trimesic acid.

The targeting moiety and cell penetrating peptide moiety can overlap. That is, the residues that form the cell penetrating peptide moiety can also be part of the sequence that forms the targeting moiety, and vice a versa.

The therapeutic moiety can be attached to the cell penetrating peptide moiety at the amino group, the carboxylate group, or the side chain of any of the amino acids of the cell penetrating peptide moiety (e.g., at the amino group, the carboxylate group, or the side chain or any of amino acid of the CPP). In some examples, the therapeutic moiety can be attached to the detectable moiety.

In some examples, the therapeutic moiety can comprise a targeting moiety that can act as an inhibitor against Ras (e.g., K-Ras), PTPIB, Pin1, Grb2 SH2, CAL PDZ, and the like, or combinations thereof.

Ras is a protein that in humans is encoded by the RAS gene. The normal Ras protein performs an essential function in normal tissue signaling, and the mutation of a Ras gene is implicated in the development of many cancers. Ras can act as a molecular on/off switch, once it is turned on Ras recruits and activates proteins necessary for the propagation of growth factor and other receptors' signal. Mutated forms of Ras have been implicated in various cancers, including lung cancer, colon cancer, pancreatic cancer, and various leukemias.

Protein-tyrosine phosphatase 1B (PTP1B) is a prototypical member of the PTP superfamily and plays numerous roles during eukaryotic cell signaling. PTPIB is a negative regulator of the insulin signaling pathway, and is considered a promising potential therapeutic target, in particular for the treatment of type II diabetes. PIP1B has also been implicated in the development of breast cancer.

Pin1 is an enzyme that binds to a subset of proteins and plays a role as a post phosphorylation control in regulating protein function. Pin1 activity can regulate the outcome of proline-directed kinase signaling and consequently can regulate cell proliferation and cell survival. Deregulation of Pin1 can play a role in various diseases. The up-regulation of Pin1 may be implicated in certain cancers, and the down-regulation of Pin1 may be implicated in Alzheimer's disease. Inhibitors of Pin1 can have therapeutic implications for cancer and immune disorders.

Grb2 is an adaptor protein involved in signal transduction and cell communication. The Grb2 protein contains one SH2 domain, which can bind tyrosine phosphorylated sequences. Grb2 is widely expressed and is essential for multiple cellular functions. Inhibition of Grb2 function can impair developmental processes and can block transformation and proliferation of various cell types.

It was recently reported that the activity of cystic fibrosis membrane conductance regulator (CFTR), a chloride ion channel protein mutated in cystic fibrosis (CF) patients, is negatively regulated by CFTR-associated ligand (CAL) through its PDZ domain (CAL-PDZ) (Wolde, M et al. *J. Biol. Chem.* 2007, 282, 8099). Inhibition of the CFTR/CAL-PDZ interaction was shown to improve the activity of ΔPhe508-CFTR, the most common form of CFTR mutation (Cheng, S H et al. *Cell* 1990, 63, 827; Kerem, BS et al. *Science* 1989, 245, 1073), by reducing its proteasome-mediated degradation (Cushing, P R et al. *Angew. Chem. Int. Ed.* 2010, 49, 9907). Thus, disclosed herein is a method for treating a subject having cystic fibrosis by administering an effective amount of a compound or composition disclosed herein. The compound or composition administered to the subject can comprise a therapeutic moiety that can comprise a targeting moiety that can act as an inhibitor against CAL PDZ. Also, the dcompositions or compositions disclosed herein can be administered with a molecule that corrects the CFTR function.

Also disclosed herein are compositions comprising the compounds described herein.

Also disclosed herein are pharmaceutically-acceptable salts and prodrugs of the disclosed compounds. Pharmaceutically-acceptable salts include salts of the disclosed compounds that are prepared with acids or bases, depending on the particular substituents found on the compounds. Under conditions where the compounds disclosed herein are sufficiently basic or acidic to form stable nontoxic acid or base salts, administration of the compounds as salts can be appropriate. Examples of pharmaceutically-acceptable base addition salts include sodium, potassium, calcium, ammonium, or magnesium salt. Examples of physiologically-acceptable acid addition salts include hydrochloric, hydrobromic, nitric, phosphoric, carbonic, sulfuric, and organic acids like acetic, propionic, benzoic, succinic, fumaric, mandelic, oxalic, citric, tartaric, malonic, ascorbic, alpha-ketoglutaric, alpha-glycophosphoric, maleic, tosyl acid, methanesulfonic, and the like. Thus, disclosed herein are the hydrochloride, nitrate, phosphate, carbonate, bicarbonate, sulfate, acetate, propionate, benzoate, succinate, fumarate, mandelate, oxalate, citrate, tartarate, malonate, ascorbate, alpha-ketoglutarate, alpha-glycophosphate, maleate, tosylate, and mesylate salts. Pharmaceutically acceptable salts of a compound can be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Methods of Making

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, WI), Acros Organics (Morris Plains, NJ), Fisher Scientific (Pittsburgh, PA), Sigma (St. Louis, MO), Pfizer (New York, NY), GlaxoSmithKline (Raleigh, NC), Merck (Whitehouse Station, NJ), Johnson & Johnson (New Brunswick, NJ), Aventis (Bridgewater, NJ), AstraZeneca (Wilmington, DE), Novartis (Basel, Switzerland), Wyeth (Madison, NJ), Bristol-Myers-Squibb (New York, NY), Roche (Basel, Switzerland), Lilly (Indianapolis, IN), Abbott (Abbott Park, IL), Schering Plough (Kenilworth, NJ), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminus is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl).

In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCI), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl) phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminus in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Methods of Use

Also provided herein are methods of use of the compounds or compositions described herein. Also provided herein are methods for treating a disease or pathology in a subject in need thereof comprising administering to the subject an effective amount of any of the compounds or compositions described herein.

Also provided herein are methods of treating cancer in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Further examples of cancers treatable by the compounds and compositions described herein include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

The methods of treatment or prevention of cancer described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts thereof as described herein can be combined into a pharmaceutical composition with an additional anti-cancer agent, such as 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine,-Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The additional anti-cancer agent can also include biopharmaceuticals such as, for example, antibodies.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease.

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation. As used herein, the term ionizing radiation refers to radiation comprising particles or photons that have sufficient energy or can produce sufficient energy via nuclear interactions to produce ionization. An example of ionizing radiation is x-radiation. An effective amount of ionizing radiation refers to a dose of ionizing radiation that produces an increase in cell damage or death when administered in combination with the compounds described herein. The ionizing radiation can be delivered according to methods as known in the art, including administering radiolabeled antibodies and radioisotopes.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

In some examples of the methods of treating of treating cancer or a tumor in a subject, the compound or composition administered to the subject can comprise a therapeutic moiety that can comprise a targeting moiety that can act as an inhibitor against Ras (e.g., K-Ras), PTP1B, Pin1, Grb2 SH2, or combinations thereof.

The disclosed subject matter also concerns methods for treating a subject having a metabolic disorder or condition. In one embodiment, an effective amount of one or more compounds or compositions disclosed herein is administered to a subject having a metabolic disorder and who is in need of treatment thereof. In some examples, the metabolic disorder can comprise type II diabetes. In some examples of the methods of treating of treating the metabolic disorder in a subject, the compound or composition administered to the subject can comprise a therapeutic moiety that can comprise a targeting moiety that can act as an inhibitor against PTP1B. In one particular example of this method the subject is obese and the method comprises treating the subject for obesity by administering a composition as disclosed herein.

The disclosed subject matter also concerns methods for treating a subject having an immune disorder or condition. In one embodiment, an effective amount of one or more compounds or compositions disclosed herein is administered to a subject having an immune disorder and who is in need of treatment thereof. In some examples of the methods of treating of treating the immune disorder in a subject, the compound or composition administered to the subject can comprise a therapeutic moiety that can comprise a targeting moiety that can act as an inhibitor against Pin1.

The disclosed subject matter also concerns methods for treating a subject having an inflammatory disorder or condition. In one embodiment, an effective amount of one or more compounds or compositions disclosed herein is administered to a subject having an inflammatory disorder and who is in need of treatment thereof.

The disclosed subject matter also concerns methods for treating a subject having cystic fibrosis. In one embodiment, an effective amount of one or more compounds or compositions disclosed herein is administered to a subject having cystic fibrosis and who is in need of treatment thereof. In some examples of the methods of treating the cystic fibrosis in a subject, the compound or composition administered to the subject can comprise a therapeutic moiety that can comprise a targeting moiety that can act as an inhibitor against CAL PDZ.

In some embodiments, the CPPs disclosed herein can be used for detecting or diagnosing a disease or condition in a subject. For example, a CPP can comprise a targeting moiety and/or a detectible moiety that can interact with a target, e.g., a tumor.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The disclosed compositions are bioavailable and can be delivered orally. Oral compositions can be tablets, troches, pills, capsules, and the like, and can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

Example 1. CPP Synthesis

Materials and General Methods. Reagents for peptide synthesis and Rink amide resin (100-200 mesh, 0.54 mmol/g) were purchased from Chem-Impex (Wood Dale, IL). The purity of the peptides was assessed by analytical HPLC and the identity was confirmed by MALDI-TOF mass spectrometric analyses on a Bruker UltrafleXtreme MALTI-TOF-TOF (Campus Chemical Instrument Center, The Ohio State University) instrument (unless noted otherwise).

Synthesis of CPP1, CPP9, CPP12, CPP1-1, CPP1-6. Peptides were manually synthesized on 100 mg of Rink amide resin (0.54 mmol/g) by standard Fmoc chemistry. For each cycle, the resin was swollen in DMF for 20 min and Fmoc group was then removed by treatment with 20% piperidine in DMF for 5 min (twice). The resin was washed with DMF/DCM/DMF (3 times) and the next amino acid was coupled in standard Fmoc/HATU chemistry by using Fmoc-amino acid/HATU/DIPEA (4, 4, 8 equiv) in DMF (2 h at RT). The coupling reactions were monitored by ninhydrin test after each position. After completion of the linear sequence, the allyl group on the α-carboxyl group of the C-terminal L-Glu was removed by treatment with tetrakis (triphenylphosphine) palladium/phenylsilane (0.3 and 10 equiv, respectively) in DCM for 15 min (3 times). The resin was washed by sodium dimethyldithiocarbamate dihydrate (SDDNa, 0.5 M in DMF) twice and the N-terminal Fmoc group was removed by treatment with 20% piperidine. The resin was washed with DMF, DCM, and DMF (3 times each) and incubated with 1 M HOBt for 5 min. The peptide was cyclized on the resin by treatment with PyBOP/HOBt/DIPEA (5, 5, and 10 equiv, respectively) for 2 h (twice). The resin was then washed with DMF and DCM (3 times each). The cyclic peptides were released from the resin and deprotected by treating the resin with 92.5% TFA, 2.5% triisopropylsilane (TIPS), 2.5% $H_2O$ and 2.5% dimethoxybenzene (DMB) for 3 h. After evaporation of the solvents, the crude peptides were triturated with cold diethylether 3 times and purified by reversed-phase HPLC on a semi-preparative C18 column. For labeling with naphthofluorescein, the purified peptide (~1 mg) was dissolved in 25 μL of DMF and the pH was adjusted to ~8 with the addition of 1 M $NaHCO_3$, and 1 mg of naphthofluorescein O-succinimidyl ester (NF-OSu) in 25 μL of DMF was added. The mixture was incubated for 2 h at RT. The labeled peptide was purified again by reversed-phase HPLC on a C18 column.

Synthesis of CPP1-3, CPP1-4, CPP1-5, CPP1-8, CPP1-10, CPP1-11, CPP1-12, CPP1-13, CPP1-14, CPP1-15, CPP-16, CPP1-17,CPP1-18, CPP1-19. Peptides were manually synthesized as described above but with the following modifications. After the coupling of Fmoc-L-Dap (methyltrityl["Mtt"])-OH, Fmoc-L-Lys (Mtt)-OH, or Fmoc-L-Orn (Mtt)-OH, the Mtt group was removed by treatment with 2% TFA and 2% triisopropylsilane in DCM (6×5 min). The exposed side-chain amino group was treated with the proper carboxylic acid/HATU/DIPEA (4, 4, 8 equiv) in DMF (2 h at RT). The resin was washed with DCM and DMF (3 times each). The allyl group on the α-carboxyl group of the C-terminal L-Glu was then removed by treatment with tetrakis (triphenylphosphine) palladium/phenylsilane (0.3 and 10 equiv, respectively) in DCM for 15 min (3 times). The peptide was then cyclized, deprotected, labeled, and purified as described above.

Synthesis of CPP1-7, CPP1-15. These two peptides were manually synthesized as described above but with the following modifications. Fmoc-L-Dap(Mtt)-OH or Fmoc-L-Lys(Mtt)-OH was used for the coupling of residue "X". After the cyclization of the peptide, the Mtt group was removed by treatment with 2% TFA and 2% triisopropylsilane in DCM (6×5 min). The exposed side-chain amino group was treated with Fmoc-OSu (for CPP1-7) or decanoic acid/HATU/DIPEA (4, 4, 8 equiv; for CPP1-15) in DMF (2 h at RT).

Synthesis of CPP1-20, CPP1-22, CPP1-23, CPP1-24, and CPP1-25. The peptides were manually synthesized as described above except for the following modifications. Fmoc-L-Asp-O-2-PhiPr or Fmoc-L-Glu-O-2-PhiPr (where 2-PhiPr is 2-phenylisopropyl) was used for the incorporation of residue "X". After that, the 2-PhiPr group was removed by treatment with 2% TFA and 2% triisopropylsilane in DCM (6×5 min). The exposed side-chain carboxyl group was then amidated by treatment with decylamine/PyBOP/HOBt/DIPEA (1, 5, 5, and 10 equiv) twice in DMF solution. The peptide was cyclized, deprotected, labeled, and purified as described above.

To generate fluorescently labelled peptides, an $N^e$-4-methoxytrityl-L-lysine was added to the C-terminus prior to peptide synthesis. After the solid-phase synthesis was complete but before cleavage, the lysine side chain was selectively deprotected using 1% (v/v) TFA in DCM. The resin was incubated with 5 equiv. of a reactive fluorescent labelling reagent (fluorescein isothiocyanate, Lissamine rhodamine B sulfonyl chloride, or naphthofluorescein succinimidyl ester) and 5 equiv. of DIPEA in DMF overnight. The labeled peptide was deprotected, triturated, purified, and analyzed by MALDI-TOF MS as described above.

Example 2. Cellular Uptake Efficiency

All of the peptides were labeled with naphthofluorescein (NF) at the Gln side chain through a long, flexible linker, miniPEG-Lys. HeLa cells were treated with 5 μM peptide for 2 h in the presence of 10% FBS and the cytosolic entry of the peptides was quantitated by flow cytometry analysis.

To determine cellular uptake efficiency of the CPPs disclosed herein, HeLa cells were cultured in 12-well plates ($1.5\times10^5$ cells per well) overnight. The cells were incubated for 2 h with 5 mM naphthofluorescein (NF)-labelled peptide in cellular media. At the end of incubation, the cells were washed with DPBS twice, detached from the plate with 0.25% trypsin, diluted into clear DMEM, pelleted at 250 g for 5 min, washed twice with DPBS, resuspended in DPBS, and analyzed on a BD FACS LSR II flow cytometer. For NF-labelled peptides, a 633-nm laser was used for excitation and the fluorescence emission was analyzed in the APC channel. Absolute cellular uptake efficiency was determined by comparing the concentration (via fluorescence intensity) of the CPP in the cytosol to the concentration in the extracellular medium. Relative cellular uptake efficiency was determined by comparing the cytosolic concentration of the CPP to that cytosolic concentration of the control CPP cyclo(FΦRRRRQ).

Figure 2:
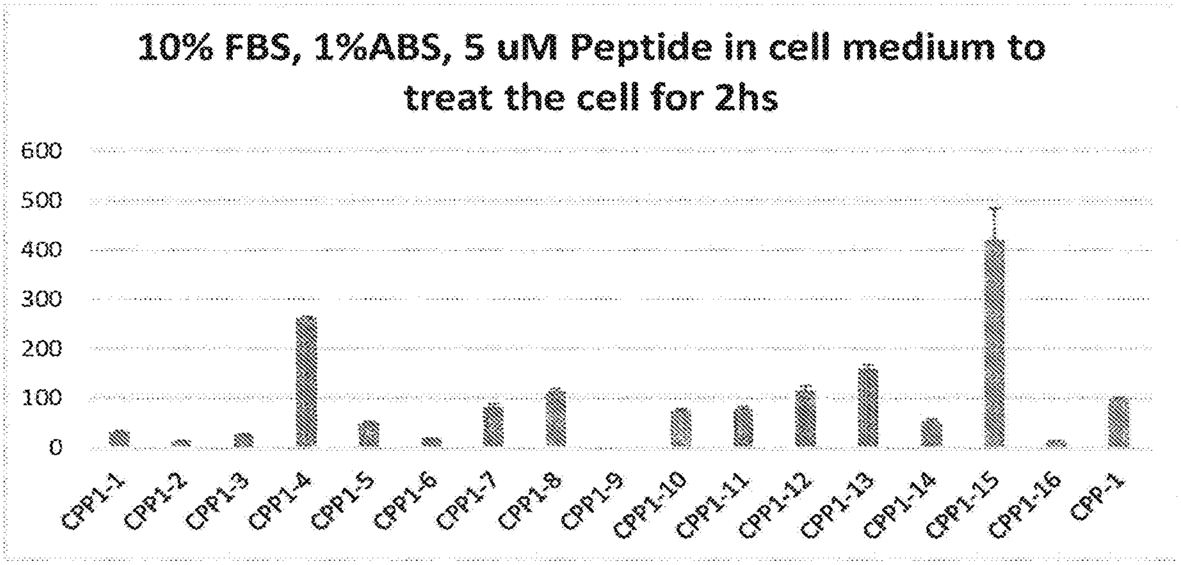
FIG. 2 is a graph showing the cytosolic entry efficiency of CPP1 and CPP1-1 to CPP1-9 as determined by flow cytometry analysis.

It is clear that the CPP activity increases with the size of the hydrophobic group (FIG. 2). CPP1-4, which contains a decanoyl group is substantially more active than CPP1-2 and CPP1-3, which have hexanoyl and octanoyl groups, respectively. Likewise, the CPP activity also generally increased with the size of the aromatic groups for CPP1-1 and CPP1-5 to CPP1-8. Remarkably, the most active CPP of this series, CPP1-4, showed 2.5-fold higher activity than CPP1, the first cyclic CPP discovered.

Stereochemical variation of CPP1-4 substantially decreased the CPP activity (FIGS. 2 and 3, CPP1-10 and CPP1-11). Replacement of an arginine with alanine also reduced the CPP activity (CPP1-12 and CPP1-13). Likewise, expansion (CPP1-14) or contraction of the ring size (CPP1-16) greatly decreased the CPP activity. Elongation of the hydrophobic side chain by replacing the Dap residue with lysine or ornithine slightly increased the CPP activity (CPP1-15 and CPP1-17, respectively) (FIGS. 2 and 3). Again, stereochemical variation of CPP1-15 reduced the CPP activity (CPP1-18 and CPP1-19).

Figure 3A:
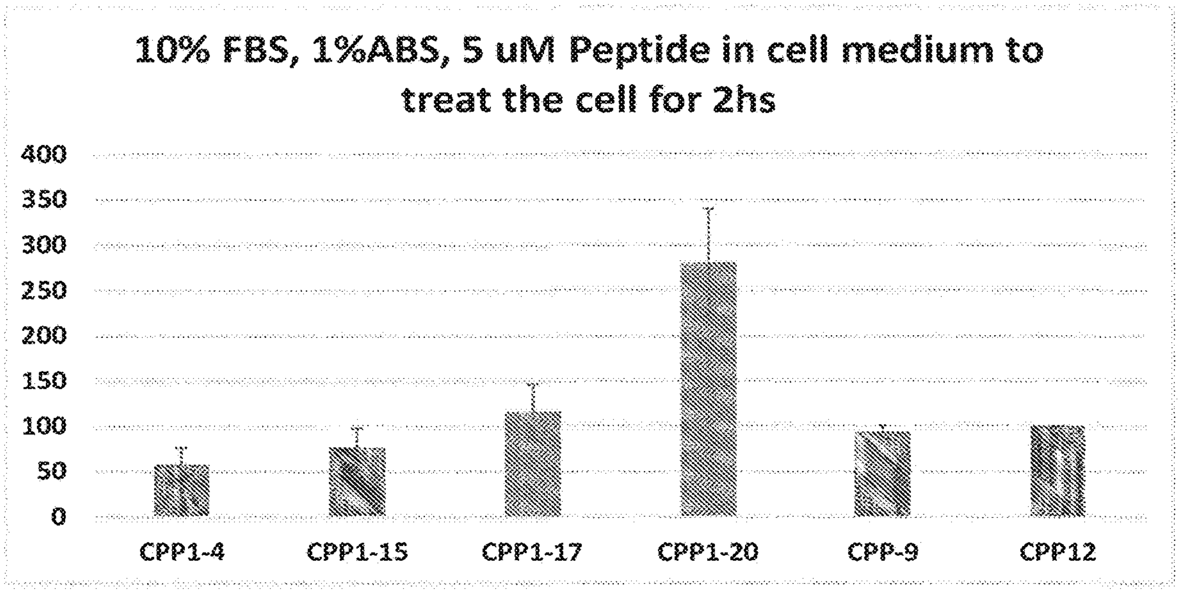
FIG. 3A compares the cytosolic entry efficiencies of CPP1-4, CPP1-15, CPP1-17, CPP1-20, CPP9, and CPP12 into HeLa cells in the presence of 10% FBS.

The Dap residue of CPP1-4 was replaced with an aspartic acid and the acid functionality was then amidated with decylamine to give CPP1-20 (FIG. 3A). Attempt to synthesize CPP1-21, which contains a glutamic acid in place of the aspartic acid, was not successful. Gratifyingly, CPP1-20 showed ~5-fold improvement in activity and is ~3-fold more active than CPP9 and CPP12 (in the presence of 10% FBS). This increase in CPP activity relative to CPP1-4 is likely due to elongation of the hydrocarbon length by one carbon atom (10 vs 9 atoms). Longer alkyl groups presumably insert more deeply into the lipid bilayer, increasing the membrane binding affinity and therefore the CPP activity. It is anticipated that still longer hydrocarbon chains (fatty acyl or alkylamine groups of ≥11 carbon atoms) may further increase the CPP activity. Variation of the stereochemistry of CPP1-20 reduced its CPP activity (CPP1-22 to CPP1-25).

Figure 3B:
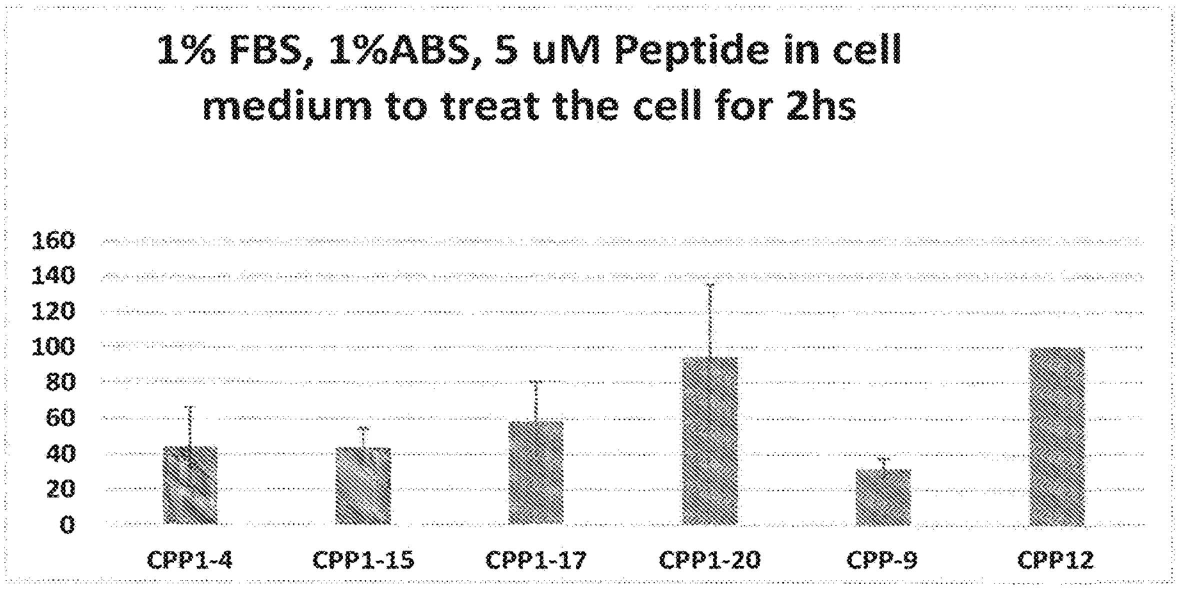
FIG. 3B compares the cytosolic entry efficiencies of CPP1-4, CPP1-15, CPP1-17, CPP1-20, CPP9, and CPP12 into HeLa cells in the presence of 1% FBS.

CPP1-4, CPP1-15, CPP1-17, and CPP1-20 show lower sensitivity to serum concentration than CPP9 or CPP12. The cytosolic entry efficiencies of these seven CPPs were tested again with Hela cells, but in the presence of reduced serum concentration (1% FBS). Under these conditions, CPP12 is the most active CPP, followed by CPP1-20 (94%), CPP1-17 (58%), CPP1-4 (44%), CPP1-15 (43%), and CPP9 (32%) (FIG. 3B). The mean fluorescence intensity (MFI) values of the treated cells were generally much higher than the corresponding values obtained in the presence of 10% FBS. In general, the cyclic CPPs with one hydrophobic group are less sensitive to the FBS concentration than CPP12, likely due to less protein binding by the former and therefore more available for membrane binding and cellular entry. This reduced sensitivity of the new CPPs to serum proteins should result in greater efficacy during in vivo applications.

TABLE 7

Sequences and Cytosolic Entry Efficiencies of Cyclic CPPs

| Peptide | Sequence[a] | SEQ. ID. NO. | Molecular Mass Calcd | Molecular Mass Obsd | Cellular Entry Efficiency[b] In 10% FBS | Cellular Entry Efficiency[b] In 1% FBS |
|---|---|---|---|---|---|---|
| CPP1 | cyclo(FΦRRRRQ) | 58 | 1827.86 | 1828.837 | 21 | |
| CPP9 | cyclo(fΦRrRrQ) | 59 | 1827.86 | 1828.778 | 94 ± 7 | 32 ± 6 |
| CPP12 | cyclo(FfΦRrRrQ) | 60 | 1974.93 | 1975.839 | 100 | 100 |
| CPP1-1 | cyclo(F$^{tBu}$RRRRQ) | 61 | 1686.84 | 1687.868 | 6.7 ± 0.4 | |
| CPP1-2 | cyclo(Dap$^{Hexan}$RRRRQ) | 62 | 1667.83 | 1668.816 | 2.9 ± 0.2 | |
| CPP1-3 | cyclo(Dap$^{Octan}$RRRRQ) | 63 | 1696.86 | 1696.889 | 5.7 ± 0.6 | |
| CPP1-4 | cyclo(Dap$^{Deca}$RRRRQ) | 64 | 1723.89 | 1746.906 | 57 ± 19 | |
| CPP1-5 | cyclo(Dap1-$^{Pyren}$RRRRQ) | 65 | 1797.82 | 1798.836 | 10 ± 20 | |
| CPP1-6 | cyclo(Dap3,3-$^{dipheny}$RRRRQ) | 66 | 1706.81 | 1707.834 | 3.9 ± 0.4 | |
| CPP1-7 | cyclo(Dap$^{Fmoc}$RRRRQ) | 67 | 1791.83 | 1792.861 | 17 ± 1 | |
| CPP1-8 | cyclo(Dap$^{1\text{-}Pyreneb}$RRRRQ) | 68 | 1839.86 | 1840.907 | 24 ± 1 | |
| CPP1-9 | Not synthesized | | | | | |

TABLE 7-continued

Sequences and Cytosolic Entry Efficiencies of Cyclic CPPs

| Peptide | Sequence[a] | SEQ. ID. NO. | Molecular Mass Calcd | Molecular Mass Obsd | Cellular Entry Efficiency[b] In 10% FBS | Cellular Entry Efficiency[b] In 1% FBS |
|---|---|---|---|---|---|---|
| CPP1-10 | cyclo(Dap$^{Deca}$RrRrQ) | 69 | 1723.89 | 1724.923 | 21 ± 9 | 24 |
| CPP1-11 | cyclo(Dap$^{Deca}$rRrRQ) | 70 | 1723.89 | 1724.895 | 20 ± 6 | 29 |
| CPP1-12 | cyclo(Dap$^{Deca}$ARRRQ) | 71 | 1638.83 | 1639.834 | 26 ± 4 | 34 |
| CPP1-13 | cyclo(Dap$^{Deca}$RRRAQ) | 72 | 1638.83 | 1639.824 | 32 ± 2 | 33 |
| CPP1-14 | cyclo(Dap$^{Deca}$RRRRRQ) | 73 | 1880.00 | 1880.979 | 12 ± 1 | 21 |
| CPP1-15 | cyclo(Lys$^{Deca}$RRRRQ) | 74 | 1765.94 | 1767.638 | 76 ± 21 | 44 ± 11 |
| CPP1-16 | cyclo(Dap$^{Deca}$RRRQ) | 75 | 1567.79 | 1568.692 | 3.0 ± 0.1 | 25 |
| CPP1-17 | cyclo(Orn$^{Deca}$RRRRQ) | 76 | 1751.93 | 1752.832 | 115 ± 32 | 58 ± 22 |
| CPP1-18 | cyclo(Lys$^{Deca}$RrRrQ) | 77 | 1765.94 | 1766.908 | 31 | |
| CPP1-19 | cyclo(Lys$^{Deca}$rRrRQ) | 78 | 1765.94 | 1766.880 | 12 | |
| CPP1-20 | cyclo(Asp$^{Decy}$RRRRQ) | 79 | 1737.91 | 1738.830 | 281 ± 59 | 94 ± 41 |
| CPP1-21 | Synthesis failed | | | | | |
| CPP1-22 | cyclo(Asp$^{Decy}$RrRrQ) | 80 | 1737.91 | 1738.844 | 11 | |
| CPP1-23 | cyclo(Glu$^{Decy}$RrRrQ) | 81 | 1751.93 | 1752.833 | 1.4 | |
| CPP1-24 | cyclo(Asp$^{Decy}$rRrRQ) | 82 | 1737.91 | 1738.854 | 8.6 | |
| CPP1-25 | cyclo(Glu$^{Decy}$rRrRQ) | 83 | 1751.93 | 1752.837 | 34 | |

[a]Single-letter codes for amino acids. Φ, 2-naphthylalanine. tBu = tert-butanoyl, hexan = hexanoyl, octan = octanoyl, deca = decanoyl, 1-pyren = pyrenoyl, 3,3-diphenyl = 3,3-diphenoyl, Fmoc = fluorenylmethyloxycarbonoyl, 1-pyreneb = 1-pyrenylbutanoyl, decy = decynoyl

[b]All values are relative to that of CPP12 (100%).

Example 4. Cytotoxicity

Figure 4:
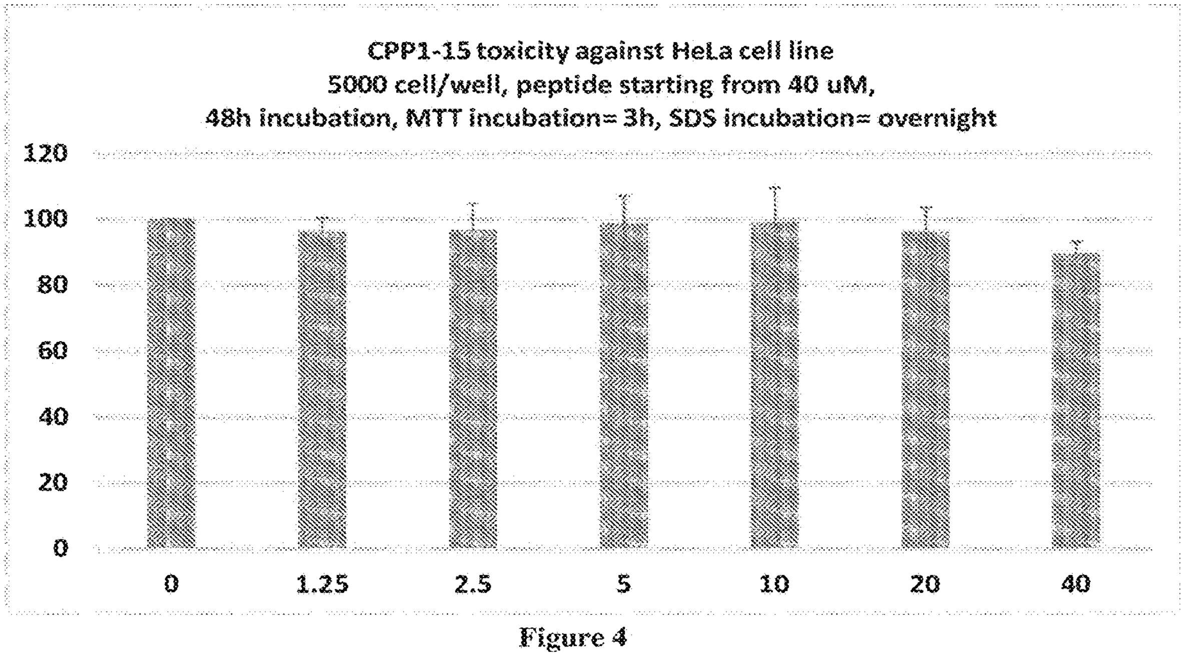
FIG. 4 illustrates that effect of CPP1-15 on the viability of HeLa cells.

CPP1-15 (no label) was used as a representative and tested against HeLa cells for potential cytotoxicity by the MTT assay. It did not show significant cytotoxicity up to 40 μM concentration (FIG. 4).

Example 5. Confirmation of Cellular Entry by Confocal Microscopy

Figures 5A, 5B:
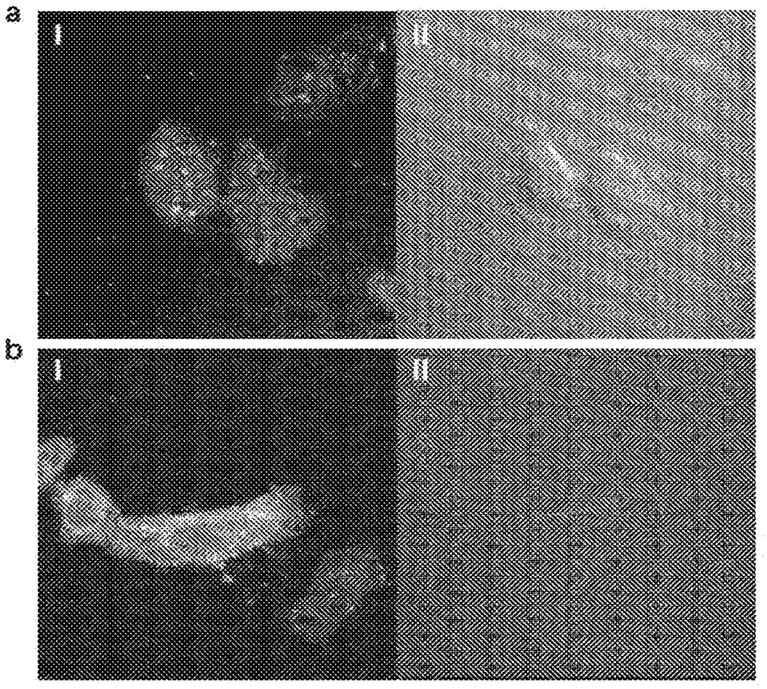
FIGS. 5A-5B shows live-cell confocal images of Hela cells after 2-h treatment of 5 μM FITC-CPP1-15 (FIG. 5A) or FITC-CPP1-20 (FIG. 5B) in the presence of 1% FBS. I, FITC fluorescence; II, DIC.

CPP1-15 and CPP1-20 were labeled with FITC via a miniPEG-Lys linker. HeLa cells were treated with 5 μM peptide for 2 h, washed, and imaged by live-cell confocal imaging. Both peptides entered HeLa cells efficiently and produced a combination of diffuse and punctate fluorescence, suggesting that they at least partially enter cells by endocytosis followed by endosomal escape (FIGS. 5A-5B). Flow cytometry analysis at different concentrations suggest that at ≥2 μM concentration, these CPPs start to enter cells by direct translocation. Additional experiments are ongoing to further examine their mechanism of cell entry.

The ability of CPP1-20 to directly translocate across the plasma membrane suggests that it may be able to deliver macromolecular cargoes such as proteins across the plasma membrane. Such transporters may have important in vitro and ex vivo applications. Ongoing studies include conjugation of CPP1-20 to EGFP and testing for entry into HeLa cells via direct translocation.

A number of embodiments of the invention have been described. Nevertheless, it will be understood that various modifications may be made without departing from the spirit and scope of the invention. Accordingly, other embodiments are within the scope of the following claims

SEQUENCE LISTING

```
Sequence total quantity: 83
SEQ ID NO: 1            moltype = AA  length = 5
FEATURE                 Location/Qualifiers
source                  1..5
                        mol_type = protein
                        organism = synthetic construct
SEQUENCE: 1
RRRRR                                                                5

SEQ ID NO: 2            moltype = AA  length = 5
FEATURE                 Location/Qualifiers
source                  1..5
                        mol_type = protein
                        organism = synthetic construct
SEQUENCE: 2
AAAAA                                                                5

SEQ ID NO: 3            moltype = AA  length = 4
FEATURE                 Location/Qualifiers
source                  1..4
                        mol_type = protein
                        organism = synthetic construct
SEQUENCE: 3
FFFF                                                                 4

SEQ ID NO: 4            moltype = AA  length = 5
FEATURE                 Location/Qualifiers
MOD_RES                 3
                        note = Phosphocoumaryl amino propionic acid
source                  1..5
                        mol_type = protein
                        organism = synthetic construct
SEQUENCE: 4
DEXLI                                                                5

SEQ ID NO: 5            moltype = AA  length = 7
FEATURE                 Location/Qualifiers
source                  1..7
                        mol_type = protein
                        organism = synthetic construct
SEQUENCE: 5
AAAAAAA                                                              7

SEQ ID NO: 6            moltype = AA  length = 5
FEATURE                 Location/Qualifiers
source                  1..5
                        mol_type = protein
                        organism = synthetic construct
SEQUENCE: 6
RARAR                                                                5

SEQ ID NO: 7            moltype = AA  length = 5
FEATURE                 Location/Qualifiers
source                  1..5
                        mol_type = protein
                        organism = synthetic construct
SEQUENCE: 7
DADAD                                                                5

SEQ ID NO: 8            moltype =   length =
SEQUENCE: 8
000

SEQ ID NO: 9            moltype =   length =
SEQUENCE: 9
000

SEQ ID NO: 10           moltype =   length =
SEQUENCE: 10
000
```

-continued

```
SEQ ID NO: 11           moltype = AA  length = 6
FEATURE                 Location/Qualifiers
MOD_RES                 2
                        note = L-homoproline
MOD_RES                 4
                        note = L-4-(phosphonodifluoromethyl)phenylalanine
source                  1..6
                        mol_type = protein
                        organism = synthetic construct
SEQUENCE: 11
PXGXYR                                                                   6

SEQ ID NO: 12           moltype =   length =
SEQUENCE: 12
000

SEQ ID NO: 13           moltype = AA  length = 6
FEATURE                 Location/Qualifiers
MOD_RES                 4
                        note = L-4-(phosphonodifluoromethyl)phenylalanine
source                  1..6
                        mol_type = protein
                        organism = synthetic construct
SEQUENCE: 13
IHIXIR                                                                   6

SEQ ID NO: 14           moltype = AA  length = 6
FEATURE                 Location/Qualifiers
source                  1..6
                        mol_type = protein
                        organism = synthetic construct
SITE                    2
                        note = D-alanine
MOD_RES                 4
                        note = L-4-(phosphonodifluoromethyl)phenylalanine
MOD_RES                 5
                        note = L-homoproline
SEQUENCE: 14
AAIXXR                                                                   6

SEQ ID NO: 15           moltype =   length =
SEQUENCE: 15
000

SEQ ID NO: 16           moltype = AA  length = 6
FEATURE                 Location/Qualifiers
source                  1..6
                        mol_type = protein
                        organism = synthetic construct
MOD_RES                 1
                        note = L-homoproline
SITE                    2
                        note = D-Asparagine
MOD_RES                 4
                        note = L-4-(phosphonodifluoromethyl)phenylalanine
SEQUENCE: 16
XNPXAR                                                                   6

SEQ ID NO: 17           moltype = AA  length = 6
FEATURE                 Location/Qualifiers
MOD_RES                 2
                        note = L-phenylglycine
MOD_RES                 4
                        note = L-4-(phosphonodifluoromethyl)phenylalanine
source                  1..6
                        mol_type = protein
                        organism = synthetic construct
SEQUENCE: 17
TXAXGR                                                                   6

SEQ ID NO: 18           moltype = AA  length = 6
FEATURE                 Location/Qualifiers
MOD_RES                 4
                        note = L-4-(phosphonodifluoromethyl)phenylalanine
SITE                    5
                        note = D-Alanine
source                  1..6
                        mol_type = protein
                        organism = synthetic construct
```

```
SEQUENCE: 18
AHIXAR                                                                   6

SEQ ID NO: 19          moltype = AA  length = 6
FEATURE                Location/Qualifiers
source                 1..6
                       mol_type = protein
                       organism = synthetic construct
SITE                   2
                       note = D-Asparagine
MOD_RES                4
                       note = L-4-(phosphonodifluoromethyl)phenylalanine
SITE                   5
                       note = D-Proline
SEQUENCE: 19
GNGXPR                                                                   6

SEQ ID NO: 20          moltype = AA  length = 6
FEATURE                Location/Qualifiers
source                 1..6
                       mol_type = protein
                       organism = synthetic construct
SITE                   1
                       note = D-Phenylalanine
MOD_RES                3
                       note = L-homoproline
MOD_RES                4
                       note = L-4-(phosphonodifluoromethyl)phenylalanine
SEQUENCE: 20
FQXXIR                                                                   6

SEQ ID NO: 21          moltype = AA  length = 6
FEATURE                Location/Qualifiers
MOD_RES                4
                       note = L-4-(phosphonodifluoromethyl)phenylalanine
source                 1..6
                       mol_type = protein
                       organism = synthetic construct
SEQUENCE: 21
SPGXHR                                                                   6

SEQ ID NO: 22          moltype = AA  length = 6
FEATURE                Location/Qualifiers
MOD_RES                1
                       note = L-homoproline
MOD_RES                4
                       note = L-4-(phosphonodifluoromethyl)phenylalanine
source                 1..6
                       mol_type = protein
                       organism = synthetic construct
SEQUENCE: 22
XYIXHR                                                                   6

SEQ ID NO: 23          moltype = AA  length = 6
FEATURE                Location/Qualifiers
SITE                   2
                       note = D-Valine
MOD_RES                4
                       note = L-4-(phosphonodifluoromethyl)phenylalanine
source                 1..6
                       mol_type = protein
                       organism = synthetic construct
SEQUENCE: 23
SVPXHR                                                                   6

SEQ ID NO: 24          moltype = AA  length = 6
FEATURE                Location/Qualifiers
MOD_RES                4
                       note = L-4-(phosphonodifluoromethyl)phenylalanine
SITE                   5
                       note = D-Asparagine
source                 1..6
                       mol_type = protein
                       organism = synthetic construct
SEQUENCE: 24
AIPXNR                                                                   6

SEQ ID NO: 25          moltype = AA  length = 6
FEATURE                Location/Qualifiers
```

-continued

```
MOD_RES                 1
                        note = L-4-fluorophenylalanine
MOD_RES                 4
                        note = L-4-(phosphonodifluoromethyl)phenylalanine
source                  1..6
                        mol_type = protein
                        organism = synthetic construct
SEQUENCE: 25
XSIXQF                                                                     6

SEQ ID NO: 26           moltype = AA  length = 6
FEATURE                 Location/Qualifiers
source                  1..6
                        mol_type = protein
                        organism = synthetic construct
SITE                    2
                        note = D-Alanine
MOD_RES                 3
                        note = L-phenylglycine
MOD_RES                 4
                        note = L-4-(phosphonodifluoromethyl)phenylalanine
SITE                    5
                        note = D-Phenylalanine
SEQUENCE: 26
AAXXFR                                                                     6

SEQ ID NO: 27           moltype =   length =
SEQUENCE: 27
000

SEQ ID NO: 28           moltype =   length =
SEQUENCE: 28
000

SEQ ID NO: 29           moltype =   length =
SEQUENCE: 29
000

SEQ ID NO: 30           moltype = AA  length = 6
FEATURE                 Location/Qualifiers
source                  1..6
                        mol_type = protein
                        organism = synthetic construct
SITE                    1
                        note = D-Asparagine
MOD_RES                 3
                        note = L-4-fluorophenylalanine
MOD_RES                 4
                        note = L-4-(phosphonodifluoromethyl)phenylalanine
SEQUENCE: 30
NAXXGR                                                                     6

SEQ ID NO: 31           moltype = AA  length = 6
FEATURE                 Location/Qualifiers
source                  1..6
                        mol_type = protein
                        organism = synthetic construct
SITE                    1
                        note = D-Asparagine
SITE                    2
                        note = D-Threonine
MOD_RES                 4
                        note = L-4-(phosphonodifluoromethyl)phenylalanine
SEQUENCE: 31
NTYXAR                                                                     6

SEQ ID NO: 32           moltype = AA  length = 6
FEATURE                 Location/Qualifiers
source                  1..6
                        mol_type = protein
                        organism = synthetic construct
SITE                    1
                        note = D-Glutamate
MOD_RES                 3
                        note = L-phenylglycine
MOD_RES                 4
                        note = L-4-(phosphonodifluoromethyl)phenylalanine
SITE                    5
                        note = D-Valine
```

```
SEQUENCE: 32
EAXXVR                                                          6

SEQ ID NO: 33          moltype = AA  length = 6
FEATURE                Location/Qualifiers
source                 1..6
                       mol_type = protein
                       organism = synthetic construct
SITE                   2
                       note = D-Valine
MOD_RES                3
                       note = L-phenylglycine
MOD_RES                4
                       note = L-4-(phosphonodifluoromethyl)phenylalanine
SEQUENCE: 33
IVXXAR                                                          6

SEQ ID NO: 34          moltype = AA  length = 6
FEATURE                Location/Qualifiers
source                 1..6
                       mol_type = protein
                       organism = synthetic construct
SITE                   2
                       note = D-Threonine
MOD_RES                3
                       note = L-phenylglycine
MOD_RES                4
                       note = L-4-(phosphonodifluoromethyl)phenylalanine
SEQUENCE: 34
YTXXAR                                                          6

SEQ ID NO: 35          moltype =   length =
SEQUENCE: 35
000

SEQ ID NO: 36          moltype = AA  length = 6
FEATURE                Location/Qualifiers
source                 1..6
                       mol_type = protein
                       organism = synthetic construct
MOD_RES                1
                       note = L-homoproline
SITE                   2
                       note = D-Asparagine
MOD_RES                4
                       note = L-4-(phosphonodifluoromethyl)phenylalanine
SEQUENCE: 36
XNWXHR                                                          6

SEQ ID NO: 37          moltype = AA  length = 6
FEATURE                Location/Qualifiers
source                 1..6
                       mol_type = protein
                       organism = synthetic construct
MOD_RES                2
                       note = L-homoproline
SITE                   3
                       note = D-Valine
MOD_RES                4
                       note = L-4-(phosphonodifluoromethyl)phenylalanine
SEQUENCE: 37
YXVXIR                                                          6

SEQ ID NO: 38          moltype = AA  length = 6
FEATURE                Location/Qualifiers
source                 1..6
                       mol_type = protein
                       organism = synthetic construct
SITE                   1
                       note = D-Asparagine
SITE                   3
                       note = D-Alanine
MOD_RES                4
                       note = L-4-(phosphonodifluoromethyl)phenylalanine
SEQUENCE: 38
NSAXGR                                                          6

SEQ ID NO: 39          moltype = AA  length = 6
FEATURE                Location/Qualifiers
```

-continued

```
source                  1..6
                        mol_type = protein
                        organism = synthetic construct
SITE                    1
                        note = D-Threonine
SITE                    2
                        note = D-Asparagine
SITE                    3
                        note = D-Valine
MOD_RES                 4
                        note = L-4-(phosphonodifluoromethyl)phenylalanine
SITE                    5
                        note = D-Alanine
SEQUENCE: 39
TNVXAR                                                                      6

SEQ ID NO: 40           moltype = AA  length = 6
FEATURE                 Location/Qualifiers
source                  1..6
                        mol_type = protein
                        organism = synthetic construct
SITE                    1
                        note = D-Asparagine
SITE                    2
                        note = D-Threonine
SITE                    3
                        note = D-Valine
MOD_RES                 4
                        note = L-4-(phosphonodifluoromethyl)phenylalanine
SITE                    5
                        note = D-Threonine
SEQUENCE: 40
NTVXTR                                                                      6

SEQ ID NO: 41           moltype = AA  length = 6
FEATURE                 Location/Qualifiers
SITE                    3
                        note = D-Threonine
MOD_RES                 4
                        note = L-4-(phosphonodifluoromethyl)phenylalanine
source                  1..6
                        mol_type = protein
                        organism = synthetic construct
SEQUENCE: 41
SITXYR                                                                      6

SEQ ID NO: 42           moltype = AA  length = 6
FEATURE                 Location/Qualifiers
source                  1..6
                        mol_type = protein
                        organism = synthetic construct
SITE                    1
                        note = D-Asparagine
MOD_RES                 2
                        note = L-4-fluorophenylalanine
SITE                    3
                        note = D-Asparagine
MOD_RES                 4
                        note = L-4-(phosphonodifluoromethyl)phenylalanine
SITE                    5
                        note = D-Leucine
SEQUENCE: 42
NXNXLR                                                                      6

SEQ ID NO: 43           moltype = AA  length = 6
FEATURE                 Location/Qualifiers
source                  1..6
                        mol_type = protein
                        organism = synthetic construct
SITE                    2..3
                        note = D-Asparagine
MOD_RES                 4
                        note = L-4-(phosphonodifluoromethyl)phenylalanine
SITE                    5
                        note = Nle
SEQUENCE: 43
YNNXXR                                                                      6

SEQ ID NO: 44           moltype = AA  length = 6
```

-continued

```
FEATURE                 Location/Qualifiers
source                  1..6
                        mol_type = protein
                        organism = synthetic construct
SITE                    1
                        note = D-Asparagine
SITE                    3
                        note = D-Asparagine
MOD_RES                 4
                        note = L-4-(phosphonodifluoromethyl)phenylalanine
SEQUENCE: 44
NYNXGR                                                                      6

SEQ ID NO: 45           moltype = AA  length = 6
FEATURE                 Location/Qualifiers
SITE                    3
                        note = D-Asparagine
MOD_RES                 4
                        note = L-4-(phosphonodifluoromethyl)phenylalanine
source                  1..6
                        mol_type = protein
                        organism = synthetic construct
SEQUENCE: 45
AWNXAR                                                                      6

SEQ ID NO: 46           moltype = AA  length = 6
FEATURE                 Location/Qualifiers
source                  1..6
                        mol_type = protein
                        organism = synthetic construct
SITE                    1
                        note = D-Valine
SITE                    2
                        note = D-Threonine
MOD_RES                 4
                        note = L-4-(phosphonodifluoromethyl)phenylalanine
SEQUENCE: 46
VTHXYR                                                                      6

SEQ ID NO: 47           moltype =   length =
SEQUENCE: 47
000

SEQ ID NO: 48           moltype = AA  length = 6
FEATURE                 Location/Qualifiers
source                  1..6
                        mol_type = protein
                        organism = synthetic construct
SITE                    1
                        note = D-Asparagine
MOD_RES                 2
                        note = L-phenylglycine
MOD_RES                 4
                        note = L-4-(phosphonodifluoromethyl)phenylalanine
SEQUENCE: 48
NXHXGR                                                                      6

SEQ ID NO: 49           moltype = AA  length = 6
FEATURE                 Location/Qualifiers
MOD_RES                 4
                        note = L-4-(phosphonodifluoromethyl)phenylalanine
source                  1..6
                        mol_type = protein
                        organism = synthetic construct
SEQUENCE: 49
PAHXGR                                                                      6

SEQ ID NO: 50           moltype = AA  length = 6
FEATURE                 Location/Qualifiers
MOD_RES                 4
                        note = L-4-(phosphonodifluoromethyl)phenylalanine
source                  1..6
                        mol_type = protein
                        organism = synthetic construct
SEQUENCE: 50
AYHXIR                                                                      6

SEQ ID NO: 51           moltype = AA  length = 6
FEATURE                 Location/Qualifiers
```

-continued

```
source                  1..6
                        mol_type = protein
                        organism = synthetic construct
SITE                    1
                        note = D-Asparagine
MOD_RES                 2
                        note = L-homoproline
SITE                    3
                        note = D-Glutamate
MOD_RES                 4
                        note = L-4-(phosphonodifluoromethyl)phenylalanine
SEQUENCE: 51
NXEXYR                                                                    6

SEQ ID NO: 52           moltype = AA  length = 6
FEATURE                 Location/Qualifiers
source                  1..6
                        mol_type = protein
                        organism = synthetic construct
SITE                    1
                        note = D-Valine
MOD_RES                 4
                        note = L-4-(phosphonodifluoromethyl)phenylalanine
SITE                    5
                        note = D-Threonine
SEQUENCE: 52
VSSXTR                                                                    6

SEQ ID NO: 53           moltype = AA  length = 8
FEATURE                 Location/Qualifiers
source                  1..8
                        mol_type = protein
                        organism = synthetic construct
SITE                    1
                        note = D-Alanine
MOD_RES                 2
                        note = MeGly
SITE                    3
                        note = D-Phosphothreonine
MOD_RES                 3
                        note = Phosphothreonine
MOD_RES                 4
                        note = L-L-homoprolineecolic acid
MOD_RES                 5
                        note = L-beta-naphthylalanine
SEQUENCE: 53
AXXXXYNK                                                                  8

SEQ ID NO: 54           moltype =   length =
SEQUENCE: 54
000

SEQ ID NO: 55           moltype = AA  length = 9
FEATURE                 Location/Qualifiers
source                  1..9
                        mol_type = protein
                        organism = synthetic construct
SITE                    1
                        note = Trimesic acid moiety attached
SITE                    1
                        note = D-Alanine
MOD_RES                 2
                        note = MeGly
MOD_RES                 3
                        note = Phosphothreonine
SITE                    3
                        note = D-Phosphothreonine
MOD_RES                 4
                        note = L-L-homoprolineecolic acid
MOD_RES                 5
                        note = L-beta-naphthylalanine
SITE                    8
                        note = D-Alanine
MOD_RES                 9
                        note = Dpr
SEQUENCE: 55
AXXXXRAAX                                                                 9

SEQ ID NO: 56           moltype = AA  length = 9
```

```
FEATURE                 Location/Qualifiers
source                  1..9
                        mol_type = protein
                        organism = synthetic construct
SITE                    1
                        note = Trimesic acid moiety attached
SITE                    1
                        note = D-Alanine
MOD_RES                 2
                        note = MeGly
MOD_RES                 3
                        note = D-Threonine
MOD_RES                 4
                        note = L-L-homoprolineecolic acid
MOD_RES                 5
                        note = L-beta-naphthylalanine
SITE                    8
                        note = D-Alanine
MOD_RES                 9
                        note = Dpr
SEQUENCE: 56
AXTXXRAAX                                                    9

SEQ ID NO: 57           moltype = AA  length = 9
FEATURE                 Location/Qualifiers
source                  1..9
                        mol_type = protein
                        organism = synthetic construct
SITE                    1
                        note = Trimesic acid moiety attached
SITE                    1
                        note = D-Alanine
MOD_RES                 2
                        note = MeGly
SITE                    3
                        note = D-Threonine
SITE                    4
                        note = D-Alanine
MOD_RES                 5
                        note = L-beta-naphthylalanine
SITE                    8
                        note = D-Alanine
MOD_RES                 9
                        note = Dpr
SEQUENCE: 57
AXTAXRAAX                                                    9

SEQ ID NO: 58           moltype = AA  length = 7
FEATURE                 Location/Qualifiers
MOD_RES                 2
                        note = 2-naphthylalanine
source                  1..7
                        mol_type = protein
                        organism = synthetic construct
REGION                  1..7
                        note = peptide is circular
SEQUENCE: 58
FXRRRRQ                                                      7

SEQ ID NO: 59           moltype = AA  length = 7
FEATURE                 Location/Qualifiers
source                  1..7
                        mol_type = protein
                        organism = synthetic construct
SITE                    1
                        note = D-Phenylalanine
MOD_RES                 2
                        note = 2-naphthylalanine
SITE                    4
                        note = D-Arginine
SITE                    6
                        note = D-Arginine
REGION                  1..7
                        note = peptide is circular
SEQUENCE: 59
FXRRRRQ                                                      7

SEQ ID NO: 60           moltype = AA  length = 8
FEATURE                 Location/Qualifiers
```

-continued

```
SITE                  2
                      note = D-Phenylalanine
MOD_RES               3
                      note = 2-naphthylalanine
SITE                  5
                      note = D-Arginine
SITE                  7
                      note = D-Arginine
source                1..8
                      mol_type = protein
                      organism = synthetic construct
REGION                1..8
                      note = peptide is circular
SEQUENCE: 60
FFXRRRRQ                                                      8

SEQ ID NO: 61         moltype = AA  length = 6
FEATURE               Location/Qualifiers
REGION                1..6
                      note = peptide is circular
MOD_RES               1
                      note = Phenylalanine with a tert-butanoyl substituent
source                1..6
                      mol_type = protein
                      organism = synthetic construct
SEQUENCE: 61
XRRRRQ                                                        6

SEQ ID NO: 62         moltype = AA  length = 6
FEATURE               Location/Qualifiers
REGION                1..6
                      note = peptide is circular
MOD_RES               1
                      note = 2,3-diaminopropionic acid with a hexanoyl substituent
source                1..6
                      mol_type = protein
                      organism = synthetic construct
SEQUENCE: 62
XRRRRQ                                                        6

SEQ ID NO: 63         moltype = AA  length = 6
FEATURE               Location/Qualifiers
REGION                1..6
                      note = peptide is circular
MOD_RES               1
                      note = 2,3-diaminopropionic acid with an octanoyl
                       substituent
source                1..6
                      mol_type = protein
                      organism = synthetic construct
SEQUENCE: 63
XRRRRQ                                                        6

SEQ ID NO: 64         moltype = AA  length = 6
FEATURE               Location/Qualifiers
REGION                1..6
                      note = peptide is circular
MOD_RES               1
                      note = 2,3-diaminopropionic acid with a decanoyl substituent
source                1..6
                      mol_type = protein
                      organism = synthetic construct
SEQUENCE: 64
XRRRRQ                                                        6

SEQ ID NO: 65         moltype = AA  length = 6
FEATURE               Location/Qualifiers
REGION                1..6
                      note = peptide is circular
MOD_RES               1
                      note = 2,3-diaminopropionic acid with a pyrenoyl substituent
source                1..6
                      mol_type = protein
                      organism = synthetic construct
SEQUENCE: 65
XRRRRQ                                                        6

SEQ ID NO: 66         moltype = AA  length = 6
FEATURE               Location/Qualifiers
```

-continued

```
REGION                 1..6
                       note = peptide is circular
MOD_RES                1
                       note = 2,3-diaminopropionic acid with a 3,3-diphenoyl
                        substituent
source                 1..6
                       mol_type = protein
                       organism = synthetic construct
SEQUENCE: 66
XRRRRQ                                                                 6

SEQ ID NO: 67          moltype = AA  length = 6
FEATURE                Location/Qualifiers
REGION                 1..6
                       note = peptide is circular
MOD_RES                1
                       note = 2,3-diaminopropionic acid with a
                        fluorenylmethyloxycarbonoyl substituent
source                 1..6
                       mol_type = protein
                       organism = synthetic construct
SEQUENCE: 67
XRRRRQ                                                                 6

SEQ ID NO: 68          moltype = AA  length = 6
FEATURE                Location/Qualifiers
REGION                 1..6
                       note = peptide is circular
MOD_RES                1
                       note = 2,3-diaminopropionic acid with a 1-pyrenylbutanoyl
                        substituent
source                 1..6
                       mol_type = protein
                       organism = synthetic construct
SEQUENCE: 68
XRRRRQ                                                                 6

SEQ ID NO: 69          moltype = AA  length = 6
FEATURE                Location/Qualifiers
source                 1..6
                       mol_type = protein
                       organism = synthetic construct
MOD_RES                1
                       note = 2,3-diaminopropionic acid with a decanoyl substituent
SITE                   3
                       note = D-Arginine
SITE                   5
                       note = D-Arginine
REGION                 1..6
                       note = peptide is circular
SEQUENCE: 69
XRRRRQ                                                                 6

SEQ ID NO: 70          moltype = AA  length = 6
FEATURE                Location/Qualifiers
source                 1..6
                       mol_type = protein
                       organism = synthetic construct
MOD_RES                1
                       note = 2,3-diaminopropionic acid with a decanoyl substituent
SITE                   2
                       note = D-Arginine
SITE                   4
                       note = D-Arginine
REGION                 1..6
                       note = peptide is circular
SEQUENCE: 70
XRRRRQ                                                                 6

SEQ ID NO: 71          moltype = AA  length = 6
FEATURE                Location/Qualifiers
REGION                 1..6
                       note = peptide is circular
MOD_RES                1
                       note = 2,3-diaminopropionic acid with a decanoyl substituent
source                 1..6
                       mol_type = protein
                       organism = synthetic construct
SEQUENCE: 71
```

-continued

```
XARRRQ                                                              6

SEQ ID NO: 72          moltype = AA  length = 6
FEATURE                Location/Qualifiers
REGION                 1..6
                       note = peptide is circular
MOD_RES                1
                       note = 2,3-diaminopropionic acid with a decanoyl substituent
source                 1..6
                       mol_type = protein
                       organism = synthetic construct
SEQUENCE: 72
XRRRAQ                                                              6

SEQ ID NO: 73          moltype = AA  length = 7
FEATURE                Location/Qualifiers
REGION                 1..7
                       note = peptide is circular
MOD_RES                1
                       note = 2,3-diaminopropionic acid with a decanoyl substituent
source                 1..7
                       mol_type = protein
                       organism = synthetic construct
SEQUENCE: 73
XRRRRRQ                                                             7

SEQ ID NO: 74          moltype = AA  length = 6
FEATURE                Location/Qualifiers
REGION                 1..6
                       note = peptide is circular
MOD_RES                1
                       note = Lysine with a decanoyl substituent
source                 1..6
                       mol_type = protein
                       organism = synthetic construct
SEQUENCE: 74
XRRRRQ                                                              6

SEQ ID NO: 75          moltype = AA  length = 5
FEATURE                Location/Qualifiers
REGION                 1..5
                       note = peptide is circular
MOD_RES                1
                       note = 2,3-diaminopropionic acid with a decanoyl substituent
source                 1..5
                       mol_type = protein
                       organism = synthetic construct
SEQUENCE: 75
XRRRQ                                                               5

SEQ ID NO: 76          moltype = AA  length = 6
FEATURE                Location/Qualifiers
REGION                 1..6
                       note = peptide is circular
SITE                   1
                       note = Orn with a decanoyl substituent
source                 1..6
                       mol_type = protein
                       organism = synthetic construct
SEQUENCE: 76
XRRRRQ                                                              6

SEQ ID NO: 77          moltype = AA  length = 6
FEATURE                Location/Qualifiers
source                 1..6
                       mol_type = protein
                       organism = synthetic construct
MOD_RES                1
                       note = Lysine with a decanoyl substituent
SITE                   3
                       note = D-Arginine
SITE                   5
                       note = D-Arginine
REGION                 1..6
                       note = peptide is circular
SEQUENCE: 77
XRRRRQ                                                              6

SEQ ID NO: 78          moltype = AA  length = 6
```

-continued

```
FEATURE              Location/Qualifiers
source               1..6
                     mol_type = protein
                     organism = synthetic construct
MOD_RES              1
                     note = Lysine with a decanoyl substituent
SITE                 2
                     note = D-Arginine
SITE                 4
                     note = D-Arginine
REGION               1..6
                     note = peptide is circular
SEQUENCE: 78
XRRRRQ                                                              6

SEQ ID NO: 79        moltype = AA  length = 6
FEATURE              Location/Qualifiers
REGION               1..6
                     note = synthetic construct
MOD_RES              1
                     note = Asparagine with a decynoyl substituent
source               1..6
                     mol_type = protein
                     organism = synthetic construct
REGION               1..6
                     note = peptide is circular
SEQUENCE: 79
XRRRRQ                                                              6

SEQ ID NO: 80        moltype = AA  length = 6
FEATURE              Location/Qualifiers
source               1..6
                     mol_type = protein
                     organism = synthetic construct
MOD_RES              1
                     note = Asparagine with a decynoyl substituent
SITE                 3
                     note = D-Arginine
SITE                 5
                     note = D-Arginine
REGION               1..6
                     note = peptide is circular
SEQUENCE: 80
XRRRRQ                                                              6

SEQ ID NO: 81        moltype = AA  length = 6
FEATURE              Location/Qualifiers
source               1..6
                     mol_type = protein
                     organism = synthetic construct
MOD_RES              1
                     note = Glutamate with a decynoyl substituent
SITE                 3
                     note = D-Arginine
SITE                 5
                     note = D-Arginine
REGION               1..6
                     note = peptide is circular
SEQUENCE: 81
XRRRRQ                                                              6

SEQ ID NO: 82        moltype = AA  length = 6
FEATURE              Location/Qualifiers
source               1..6
                     mol_type = protein
                     organism = synthetic construct
MOD_RES              1
                     note = Asparagine with a decynoyl substituent
SITE                 2
                     note = D-Arginine
SITE                 4
                     note = D-Arginine
REGION               1..6
                     note = peptide is circular
SEQUENCE: 82
XRRRRQ                                                              6

SEQ ID NO: 83        moltype = AA  length = 6
FEATURE              Location/Qualifiers
```

-continued

| | | |
|---|---|---|
| source | 1..6 | |
| | mol_type = protein | |
| | organism = synthetic construct | |
| MOD_RES | 1 | |
| | note = Glutamate with a decynoyl substituent | |
| SITE | 2 | |
| | note = D-Arginine | |
| SITE | 4 | |
| | note = D-Arginine | |
| REGION | 1..6 | |
| | note = peptide is circular | |
| SEQUENCE: 83 | | |
| XRRRRQ | | 6 |

I claim:

1. A cyclic peptide of structure

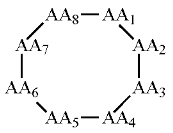

I-D or a pharmaceutically acceptable salt thereof;

wherein each of $AA_1$, $AA_2$, $AA_3$, $AA_4$, $AA_5$, $AA_6$, $AA_7$, and $AA_8$, are independently selected from an amino acid, and there is a cargo moiety coupled to a side chain of a glutamine selected from $AA_1$, $AA_2$, $AA_3$, $AA_4$, $AA_5$, $AA_6$, $AA_7$, and $AA_8$;

two of $AA_1$, $AA_2$, $AA_3$, $AA_4$, $AA_5$, $AA_6$, $AA_7$, and $AA_8$ are arginine;

at least one of $AA_1$, $AA_2$, $AA_3$, $AA_4$, $AA_5$, $AA_6$, $AA_7$, and $AA_8$ is an amino acid having a non-aromatic hydrophobic side chain;

at least one of $AA_1$, $AA_2$, $AA_3$, $AA_4$, $AA_5$, $AA_6$, $AA_7$, and $AA_8$ is an amino acid having an aromatic hydrophobic side chain;

all of the amino acids are in the natural stereoconfiguration;

an arginine residue is adjacent to a hydrophobic amino acid residue; and the cargo moiety comprises a linker moiety, a therapeutic moiety, and a targeting moiety.

2. The cyclic peptide of claim 1, wherein the at least one aromatic hydrophobic amino acid is napthylalanine.

3. The cyclic peptide of claim 1, wherein the at least one aromatic hydrophobic amino acid is phenylalanine.

4. The cyclic peptide of claim 1, comprising two aromatic hydrophobic amino acids.

5. The cyclic peptide of claim 4, wherein the two aromatic hydrophobic amino acids are naphthylalanine.

6. The cyclic peptide of claim 4, wherein the two aromatic hydrophobic amino acids are phenylalanine.

7. The cyclic peptide of claim 1, wherein two of $AA_1$, $AA_2$, $AA_3$, $AA_4$, $AA_5$, $AA_6$, $AA_7$, and $AA_8$ are non-aromatic hydrophobic amino acids.

8. The cyclic peptide of claim 7, wherein a non-aromatic hydrophobic amino acid is glycine.

9. The cyclic peptide of claim 1, wherein an arginine residue is adjacent to a non-aromatic hydrophobic amino acid residue.

10. The cyclic peptide of claim 9, wherein an arginine residue is adjacent to a glycine residue.

11. The cyclic peptide of claim 9, wherein both arginine residues are adjacent to glycine residues.

12. The cyclic peptide of claim 1, wherein the cargo moiety comprises an 8-amino -3,6-dioxaoctanoic acid.

13. The cyclic peptide of claim 1, comprising at least three adjacent hydrophobic amino acids.

14. The cyclic peptide of claim 13, wherein at least one of the adjacent hydrophobic amino acids are glycine.

15. The cyclic peptide of claim 13, wherein at least one of the hydrophobic amino acids are phenylalanine.

* * * * *